United States Patent
Arcangeli et al.

(10) Patent No.: US 11,572,406 B2
(45) Date of Patent: Feb. 7, 2023

(54) MONO AND BISPECIFIC ANTIBODY BINDING TO HERG1 AND HERG1/INTEGRIN BETA 1

(71) Applicants: UNIVERSITA' DEGLI STUDI DI FIRENZE, Florence (IT); DI. V.A.L. TOSCANA S.R.L., Sesto Fiorentino (IT)

(72) Inventors: Annarosa Arcangeli, Florence (IT); Claudia Duranti, Pontassieve (IT); Laura Carraresi, Florence (IT); Silvia Crescioli, Florence (IT)

(73) Assignee: UNIVERSITÀ DEGLI STUDI DI FIRENZE, Sesto Fiorentino (IT)

( * ) Notice: Subject to any disclaimer, the term of this patent is extended or adjusted under 35 U.S.C. 154(b) by 295 days.

(21) Appl. No.: 16/632,803

(22) PCT Filed: Jun. 29, 2018

(86) PCT No.: PCT/EP2018/067641
§ 371 (c)(1),
(2) Date: Jan. 21, 2020

(87) PCT Pub. No.: WO2019/015936
PCT Pub. Date: Jan. 24, 2019

(65) Prior Publication Data
US 2021/0147574 A1    May 20, 2021

(30) Foreign Application Priority Data
Jul. 21, 2017 (IT) .......................... 102017000083637

(51) Int. Cl.
C07K 16/28    (2006.01)
A61P 35/00    (2006.01)
A61K 39/00    (2006.01)

(52) U.S. Cl.
CPC .............. *C07K 16/28* (2013.01); *A61P 35/00* (2018.01); *C07K 16/2842* (2013.01); *A61K 2039/505* (2013.01); *C07K 2317/31* (2013.01); *C07K 2317/56* (2013.01); *C07K 2317/622* (2013.01); *C07K 2317/626* (2013.01)

(58) Field of Classification Search
CPC .............. A61K 2039/505; A61P 35/00; C07K 16/28; C07K 16/2842; C07K 2317/31; C07K 2317/56; C07K 2317/626
See application file for complete search history.

(56) References Cited

FOREIGN PATENT DOCUMENTS

WO    2016/020483 A1    2/2016

OTHER PUBLICATIONS

Paul, William, Fundamental Immunology, 3rd Edition, Raven Press, New York, 1993, pp. 292-295.*
Vajdos et al., Comprehensive functional maps of the antigen-binding site of an anti-ErbB2 antibody obtained with shotgun scanning mutagenesis. J. Mol. Biol. 320:415-428, 2002.*
Rudikoff et al., Single amino acid substitution altering antigen-binding specificity. Proc. Natl. Acad. Sci. USA 79:1979-1983, 1982.*
Brown et al., Tolerance of single, but not multiple, amino acid replacements in antibody VH CDR 2: a means of minimizing B cell wastage from somatic hypermutation? J. Immunology 156: 3285-3291, 1996.*
International Search Report and Written Opinion for PCT/EP2018/067641, dated Sep. 17, 2018.
Becchetti, et al., "The Conformational State of hERG1 Channels Determines Integrin Association, Downstream Signaling, and Cancer Progression," Sci. Signal., 10 (473):eaaf3236 (2017).
Duranti, et al., A Novel Bispecific Antibody to Harness the hERG1-[beta]1 Macromolecular Complex for Cancer Therapy, ESMO Open, 3(Suppl. 2), A352 (2018).
HERG1 Monoclonal Antibody [A12] product listing, Epigenetek Catalog (retrieved on Apr. 15, 2015).
Zanieri, et al., "[Beta]1 Integrin/hERG1 Complex as a Novel Molecular Target for Antineoplastic Therapy," ABCD 2011 Congress Abstracts, p. 58 (Sep. 8, 2011).

* cited by examiner

*Primary Examiner* — Ruixiang Li
(74) *Attorney, Agent, or Firm* — Troutman Pepper Hamilton Sanders LLP (Rochester)

(57) ABSTRACT

The present invention describes a bispecfic antibody composed of the variable domains (VH and VL) of two antibodies, hERG1 mAb (which binds the extracellular domain S5-P of hERG1) and of β1 integrin mAb TS2/16 or BV7, which bind the extracellular domain of β1 integrin. The present invention relates also to a novel anti-hERG1 molecule bearing a Cys in position 95 of the VH domain. The invention describes also their application for diagnostic and therapeutic purposes in oncology and other fields of medical sciences.

22 Claims, 23 Drawing Sheets
Specification includes a Sequence Listing.

A
FIG. 3
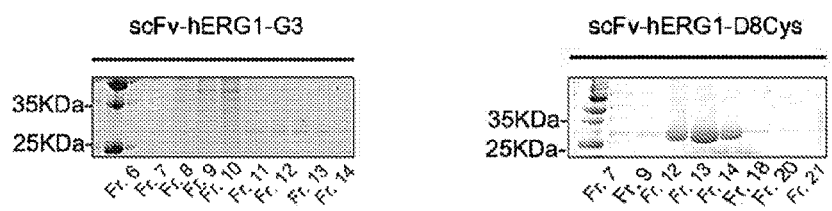
B
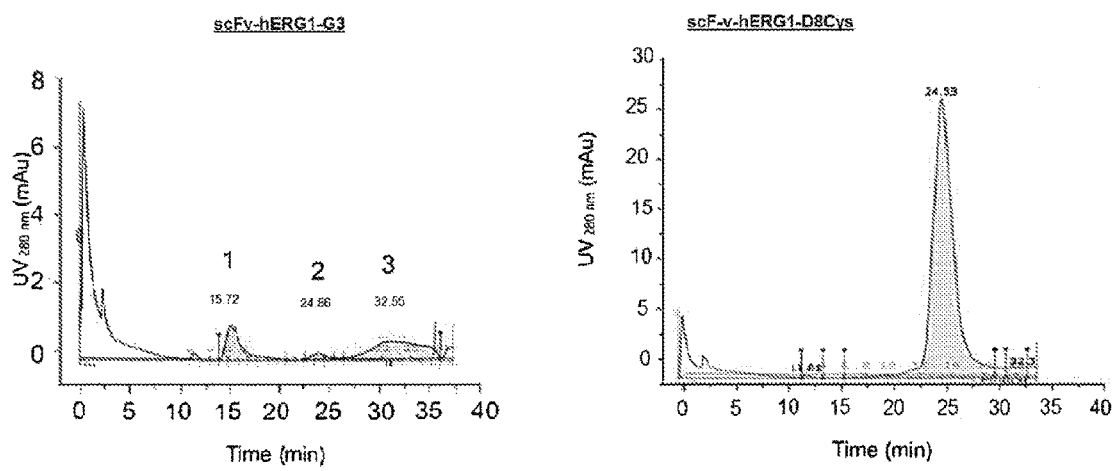
C
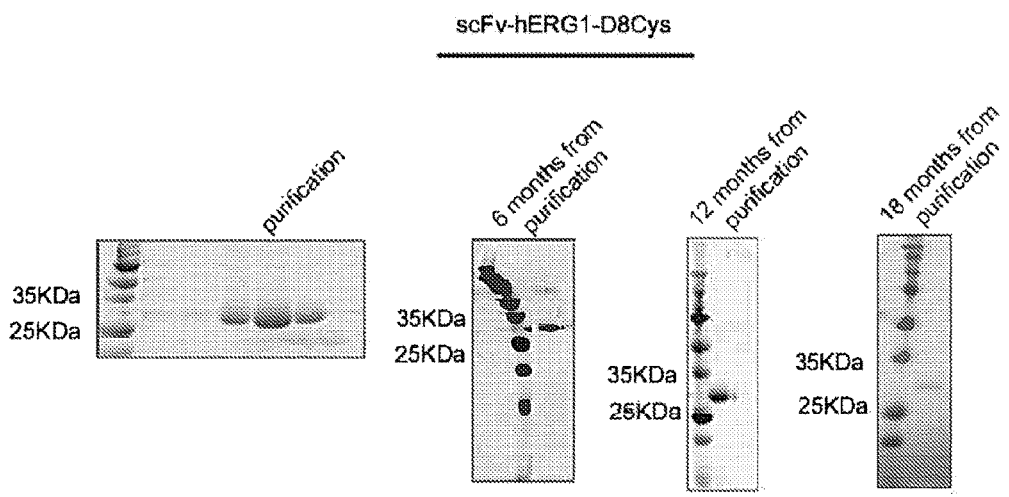

FIG. 4
A
scFv-hERG1-G3
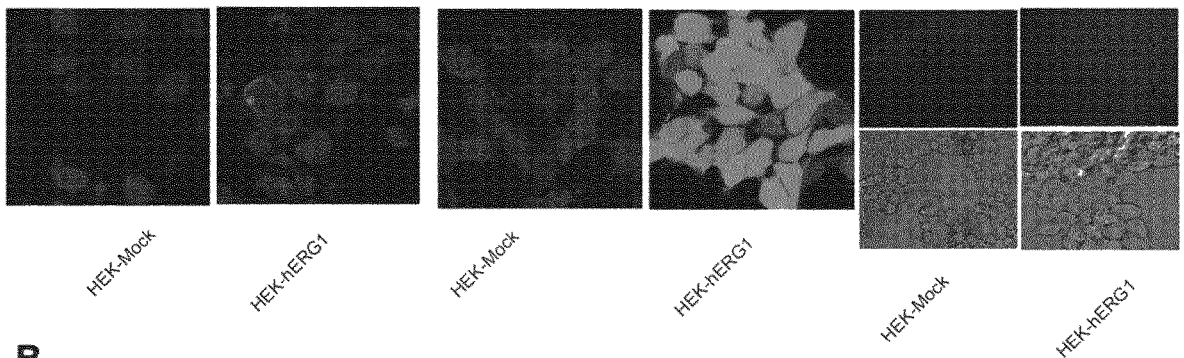
B
scFv-hERG1-D8Cys
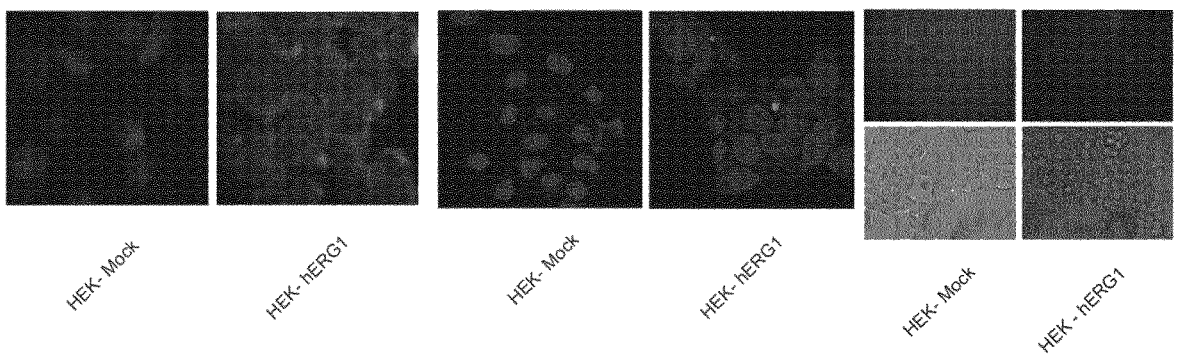
C
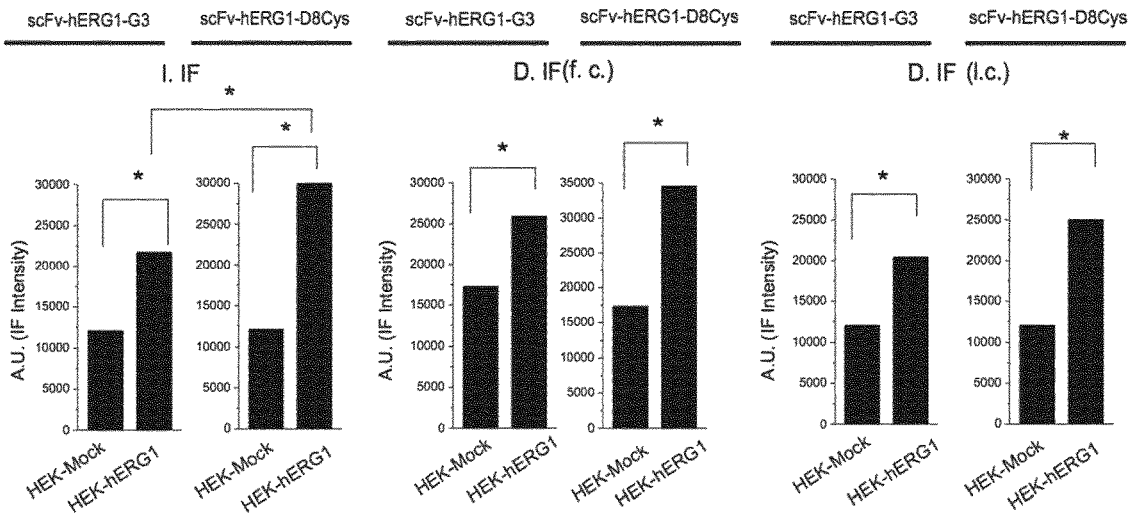

VL domain nucleotide sequence (SEQ ID No: 23):

GATATTGTGATGACACAGACTCCAACCACCATGGCTGCATCTCCCGGGGACAAGATCACTATC

ACCTGCAGTGTCAGTTCAATTATAAGTTCCAATTACCTGCATTGGTATAGTCAGAAGCCAGGAT

TCTCCCCTAAACTCTTGATTTATAGGACATCCAATCTGGCTTCTGGAGTCCCACCTCGCTTCAGT

GGCAGTGGGTCTGGGACCTCTTACTCTCTCACAATTGGCACCATGGAGGCTGAAGATGTTGCC

ACTTACTACTGCCAGCAGGGTTCTGATATTCCACTCACGTTCGGTGATGGGACCAAGCTGGAC

CTGAAACGGGCTGATGCTGCACCAACTGTATCC

VH domain nucleotide sequence (SEQ ID No: 25)

GAGGTGAAGGTGGTGGAATCTGGGGGAGGCTTAGTGAAGCCTGGAGGGTCCCTGAAACTCTC

CTGTGCAGCCTCTGGATTCACTTTCAGTAGCTATACCATGTCTTGGGTTCGCCAGACTCCGGAG

AAGAGGCTGGAGTGGGTCGCAACCATAAGTAGTGGTGGTTCTTACACCTACTATCCAGACAGT

GTGAAGGGCCGATTCACCATTTCCAGAGACAAAGCCAAGAACACCCTGTATTTGCAAATGGG

CAGTCTGAAGTCTGAGGACACAGCCATGTATTACTGTACAAGAATAGGTTACGACGAAGATTA

TGCTATGGACCACTGGGGTCAAGGAACCTCAGTCACCGTCTCCTCAGCCAAAACGACACCCC

CATCTGTCTAT

FIG. 8B

BV7 ANTIBODY V<sub>H</sub> AND V<sub>L</sub> SEQUENCES

V$_H$ nucleotide sequence (SEQ ID N: 45)
of BV7 antibody

GAGGTGAAGCTGGTGGAATCTGGGGGAGGCTTAGTGCAGCCTGGAGAGTCCCTGAAACTCTCCTG
TGAATCCAATGAATACGAATTCCCTTCCCATGATTTGTCTTGGGTCCGCAAGACTCCGGAGAAGA
GGCTGGAGTTGGTCGCAGCCATTAATAGTGATGGTGGTAGCACCTACTATCCAGACACCATGGAG
AGACGATTCATCATCTCCAGAGACAATACCAAGAAGACCCTGTACCTGCAAATGAGCAGTCTGAG
GTCTGAGGACACAGCCTTGTATTACTGTGCAAGNCGTCTATTCTAYGTACGACGGTTCTACTTTGA
CTTCTGGGGCCAAGGCACCACTCTCACAGTCTCCTCAGCCAAAACGACACCCCATCTGTCTAT

V$_L$ nucleotide sequence (SEQ ID N: 47)
of BV7 antibody

GATATTGTGATCACCCAGTCTCCATCCTCCCTGTCTGCCTCTCTGGGAGACAGAGTCACCATCAG
TTGCAGGGCAAGTCAGGACATTAGGAATTATTTAAACTGGTATCAGCAGAAACCAGATGGAACTG
TTAAACTCCTCATCTACTACACATCAAGATTACACTCAGGAGTCCCATCAAGGTTCAGTGGCAGT
GGGTCTGGAACAGATTATTCTCTCACCATTACCAACCTGGAGCAAGAAGATATTGCCACTTACTT
TTGCCAACAGGGTAATACTCTTCCATGGACGTTCGGTGGAGGCACCAAGCTGGGAATCAAGCGGG
CTGATGCTGCACCAACTGTATCC

A
HEK 293 hERG1
BSA
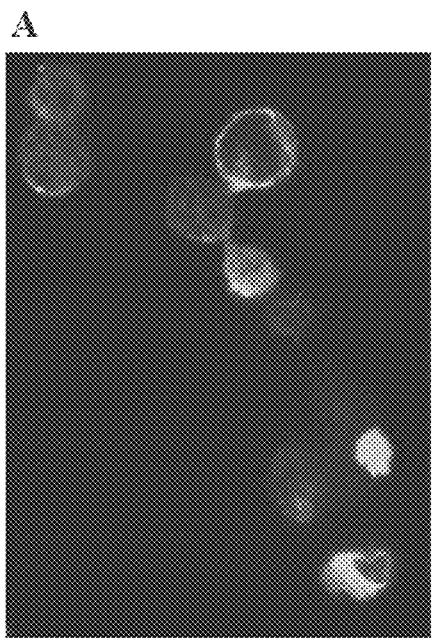
B
HEK 293 hERG1
BSA
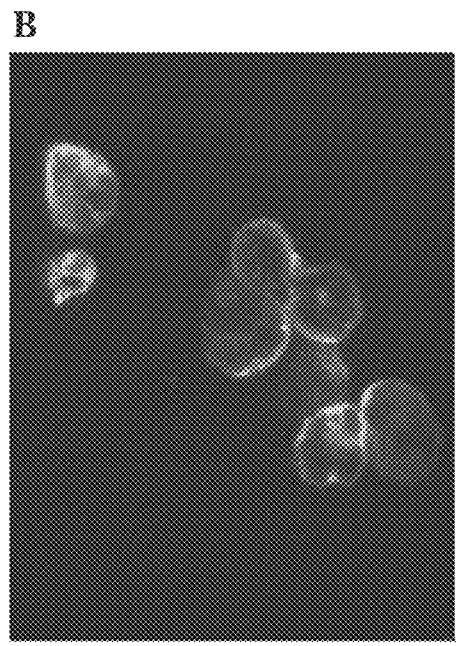
C
HEK 293 hERG1
FIBRONECTIN
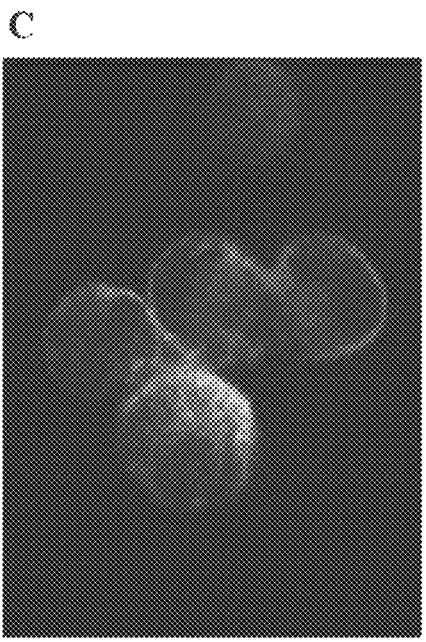
D
HEK 293 hERG1
FIBRONECTIN
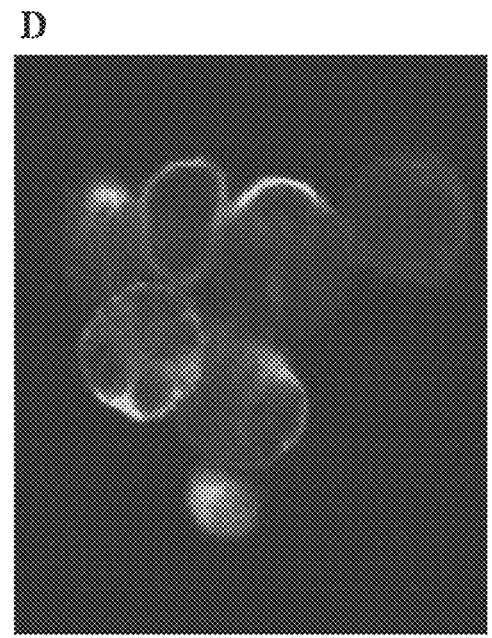
FIG. 13

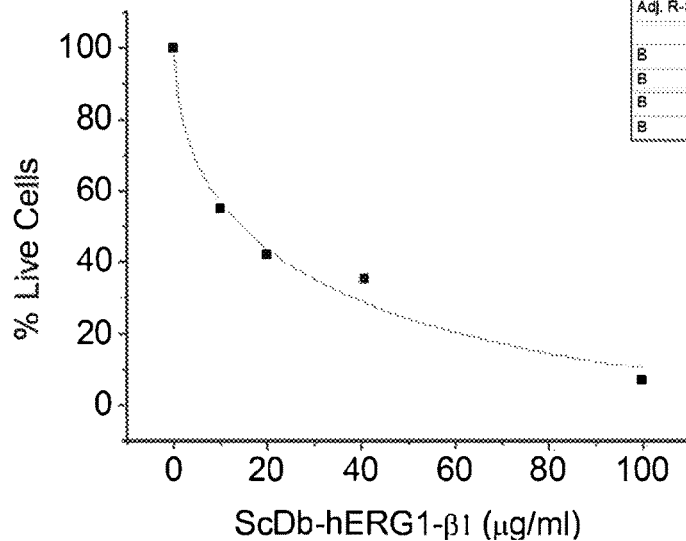
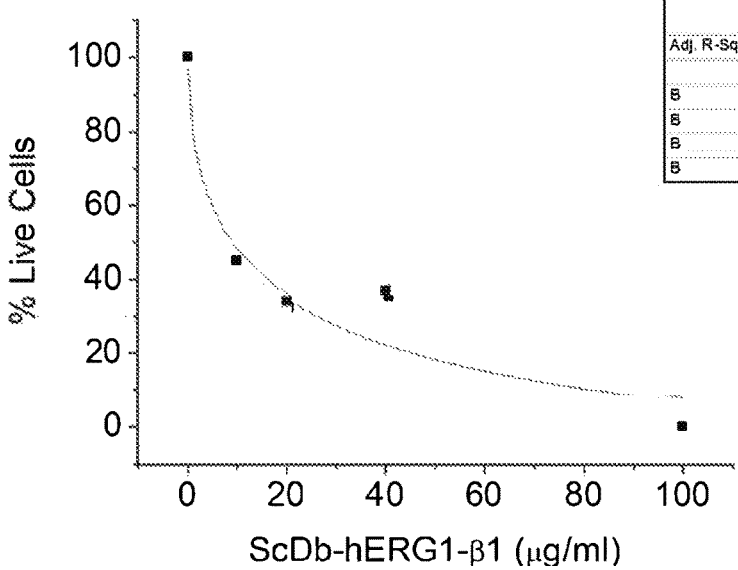
FIG. 17

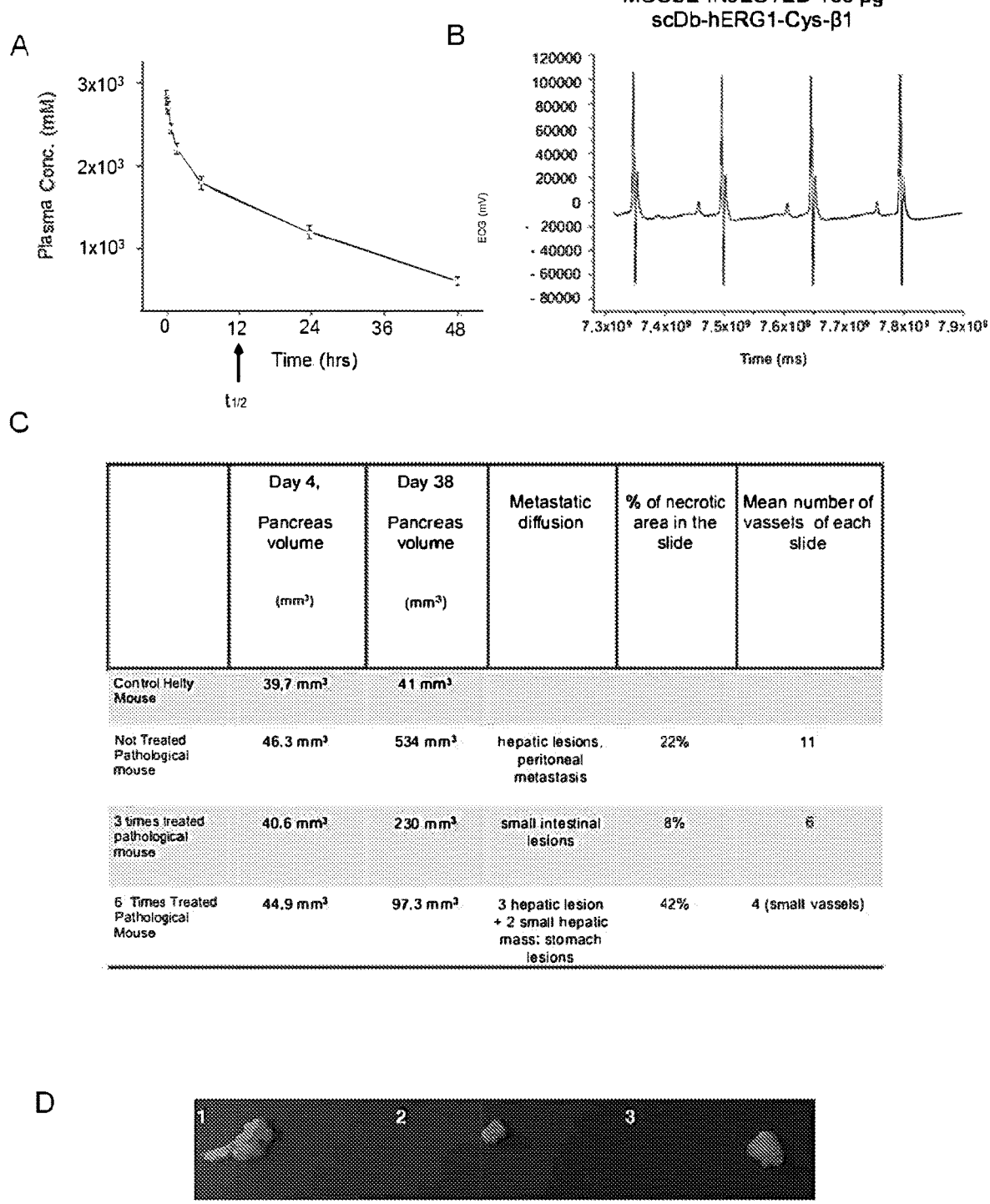

SEQUENCE LISTING

```
<160> NUMBER OF SEQ ID NOS: 48

<210> SEQ ID NO 1
<211> LENGTH: 381
<212> TYPE: DNA
<213> ORGANISM: Mus musculus
<220> FEATURE:
<221> NAME/KEY: CDS
<222> LOCATION: 1..381
<223> OTHER INFORMATION: /note="hERG1 VH domain"
      /transl_table=1
<300> PUBLICATION INFORMATION:
<310> PATENT DOCUMENT NUMBER: WO2016020483
<312> PUBLICATION DATE: 2016-02-11
<313> RELEVANT RESIDUES IN SEQ ID NO: (1)..(381)

<400> SEQUENCE: 1 gag gtc caa ctg caa cag tct gga cct gaa ctg gtg aag cct ggg gct      48
Glu Val Gln Leu Gln Gln Ser Gly Pro Glu Leu Val Lys Pro Gly Ala
1               5                   10                  15 tct gtg aag ata tcc tgc aag act tca gga tac aca ttc act gaa tac      96
Ser Val Lys Ile Ser Cys Lys Thr Ser Gly Tyr Thr Phe Thr Glu Tyr
            20                  25                  30 acc gtt cac tgg gtg aaa cag agc cat gga aag agc ctt gaa tgg att     144
Thr Val His Trp Val Lys Gln Ser His Gly Lys Ser Leu Glu Trp Ile
        35                  40                  45 gga ggc att aat cct aat ggt ggt act acc tat aat cag aag ttc aag     192
Gly Gly Ile Asn Pro Asn Gly Gly Thr Thr Tyr Asn Gln Lys Phe Lys
    50                  55                  60 ggc aag gcc aca ttg act att gac aag tcc tcc agc tca gcc ttc atg     240
Gly Lys Ala Thr Leu Thr Ile Asp Lys Ser Ser Ser Ser Ala Phe Met
65                  70                  75                  80 gag ctc cgc agc ctg aca tct gag gat tct gca gtc tat tac ttt gca     288
Glu Leu Arg Ser Leu Thr Ser Glu Asp Ser Ala Val Tyr Tyr Phe Ala
                85                  90                  95 aca ggt tgg gga cct gac tac tgg ggc caa ggc acc act ctc aca gtc     336
Thr Gly Trp Gly Pro Asp Tyr Trp Gly Gln Gly Thr Thr Leu Thr Val
            100                 105                 110 tcc tca gcc aaa aca aca ccc cca tca gtc tat cca ctg gcc cct         381
Ser Ser Ala Lys Thr Thr Pro Pro Ser Val Tyr Pro Leu Ala Pro
        115                 120                 125

<210> SEQ ID NO 2
<211> LENGTH: 127
<212> TYPE: PRT
<213> ORGANISM: Mus musculus
<220> FEATURE:
<223> OTHER INFORMATION: [CDS]:1..381 from SEQ ID NO 1

<400> SEQUENCE: 2

Glu Val Gln Leu Gln Gln Ser Gly Pro Glu Leu Val Lys Pro Gly Ala
1               5                   10                  15
```

```
Ser Val Lys Ile Ser Cys Lys Thr Ser Gly Tyr Thr Phe Thr Glu Tyr
        20                  25                  30

Thr Val His Trp Val Lys Gln Ser His Gly Lys Ser Leu Glu Trp Ile
        35                  40                  45

Gly Gly Ile Asn Pro Asn Gly Gly Thr Thr Tyr Asn Gln Lys Phe Lys
50                  55                  60

Gly Lys Ala Thr Leu Thr Ile Asp Lys Ser Ser Ser Ala Phe Met
65                  70                  75                  80

Glu Leu Arg Ser Leu Thr Ser Glu Asp Ser Ala Val Tyr Tyr Phe Ala
            85                  90                  95

Thr Gly Trp Gly Pro Asp Tyr Trp Gly Gln Gly Thr Thr Leu Thr Val
                100                 105                 110

Ser Ser Ala Lys Thr Thr Pro Pro Ser Val Tyr Pro Leu Ala Pro
        115                 120                 125
```

<210> SEQ ID NO 3
<211> LENGTH: 363
<212> TYPE: DNA
<213> ORGANISM: Mus musculus
<220> FEATURE:
<221> NAME/KEY: CDS
<222> LOCATION: 1..363
<223> OTHER INFORMATION: /note="hERG1 VL domain"
      /transl_table=1
<300> PUBLICATION INFORMATION:
<310> PATENT DOCUMENT NUMBER: WO2016020483
<312> PUBLICATION DATE: 2016-02-11
<313> RELEVANT RESIDUES IN SEQ ID NO: (1)..(363)

<400> SEQUENCE: 3

```
gat att gtg ctg aca caa tct cca ctc act ttg tcg gtt aac att ggt     48
Asp Ile Val Leu Thr Gln Ser Pro Leu Thr Leu Ser Val Asn Ile Gly
1               5                   10                  15 caa cca gcc tct atc tct tgc aag tca agt cag agc ctc tta tat act     96
Gln Pro Ala Ser Ile Ser Cys Lys Ser Ser Gln Ser Leu Leu Tyr Thr
            20                  25                  30 aat gga aaa acc tat ttt aat tgg tta tta cag agg cca ggc cag tct    144
Asn Gly Lys Thr Tyr Phe Asn Trp Leu Leu Gln Arg Pro Gly Gln Ser
        35                  40                  45 cca aag cgc cta atc tat ctg gtg tct aaa ctg gac tct gga gtc cct    192
Pro Lys Arg Leu Ile Tyr Leu Val Ser Lys Leu Asp Ser Gly Val Pro
    50                  55                  60 gac agg ttc act ggc agt gga tca gga aca gat ttt aca ctg aaa atc    240
Asp Arg Phe Thr Gly Ser Gly Ser Gly Thr Asp Phe Thr Leu Lys Ile
65                  70                  75                  80 agc aga gtg gag gct gaa gat ttg gga gtt tat tac tgc gcg caa ggt    288
Ser Arg Val Glu Ala Glu Asp Leu Gly Val Tyr Tyr Cys Ala Gln Gly
            85                  90                  95 aca cat ttt ccg tgg acg ttc ggt gga ggg acc aag ctg gaa atc aaa    336
Thr His Phe Pro Trp Thr Phe Gly Gly Gly Thr Lys Leu Glu Ile Lys
        100                 105                 110 cgg gct gat gct gca cca act gta tcc                                363
Arg Ala Asp Ala Ala Pro Thr Val Ser
    115                 120
```

<210> SEQ ID NO 4
<211> LENGTH: 121
<212> TYPE: PRT
<213> ORGANISM: Mus musculus
<220> FEATURE:
<223> OTHER INFORMATION: [CDS]:1..363 from SEQ ID NO 3

<400> SEQUENCE: 4

```
Asp Ile Val Leu Thr Gln Ser Pro Leu Thr Leu Ser Val Asn Ile Gly
1               5                   10                  15

Gln Pro Ala Ser Ile Ser Cys Lys Ser Ser Gln Ser Leu Leu Tyr Thr
            20                  25                  30

Asn Gly Lys Thr Tyr Phe Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Ala Gln Gly
                85                  90                  95

Thr His Phe Pro Trp Thr Phe Gly Gly Gly Thr Lys Leu Glu Ile Lys
            100                 105                 110

Arg Ala Asp Ala Ala Pro Thr Val Ser
            115                 120
```

<210> SEQ ID NO 5
<211> LENGTH: 879
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: 28..879
<223> OTHER INFORMATION: /note="hERG1 scFv"
/transl_table=1
<300> PUBLICATION INFORMATION:
<310> PATENT DOCUMENT NUMBER: WO2016020483
<312> PUBLICATION DATE: 2016-02-11
<313> RELEVANT RESIDUES IN SEQ ID NO: (1)..(798)

<400> SEQUENCE: 5

```
atggcccagg tgcagctgca ggtcgac gag gtc caa ctg caa cag tct gga cct        54
                            Glu Val Gln Leu Gln Gln Ser Gly Pro
                              1               5 gaa ctg gtg aag cct ggg gct tct gtg aag ata tcc tgc aag act tca         102
Glu Leu Val Lys Pro Gly Ala Ser Val Lys Ile Ser Cys Lys Thr Ser
 10              15                  20                  25 gga tac aca ttc act gaa tac acc gtt cac tgg gtg aaa cag agc cat         150
Gly Tyr Thr Phe Thr Glu Tyr Thr Val His Trp Val Lys Gln Ser His
                 30                  35                  40 gga aag agc ctt gaa tgg att gga ggc att aat cct aat ggt ggt act         198
Gly Lys Ser Leu Glu Trp Ile Gly Gly Ile Asn Pro Asn Gly Gly Thr
             45                  50                  55 acc tat aat cag aag ttc aag ggc aag gcc aca ttg act att gac aag         246
Thr Tyr Asn Gln Lys Phe Lys Gly Lys Ala Thr Leu Thr Ile Asp Lys
         60                  65                  70 tcc tcc agc tca gcc ttc atg gag ctc cgc agc ctg aca tct gag gat         294
Ser Ser Ser Ser Ala Phe Met Glu Leu Arg Ser Leu Thr Ser Glu Asp
     75                  80                  85 tct gca gtc tat tac ttt gca aca ggt tgg gga cct gac tac tgg ggc         342
Ser Ala Val Tyr Tyr Phe Ala Thr Gly Trp Gly Pro Asp Tyr Trp Gly
 90                  95                 100                 105 caa ggc acc act ctc aca gtc tcc tca gcc aaa aca aca ccc cca tca         390
Gln Gly Thr Thr Leu Thr Val Ser Ser Ala Lys Thr Thr Pro Pro Ser
                110                 115                 120
```

| | | | | | | | | | | | | | | |
|---|---|---|---|---|---|---|---|---|---|---|---|---|---|---|
| gtc | tat | cca | ctg | gcc | cct | ggc | tcg | agt | ggt | gga | ggc | ggt | tca ggc gga | 438 |
| Val | Tyr | Pro | Leu | Ala | Pro | Gly | Ser | Ser | Gly | Gly | Gly | Gly | Ser Gly Gly | |
| | | | 125 | | | | | 130 | | | | | 135 | |

```
gtc tat cca ctg gcc cct ggc tcg agt ggt gga ggc ggt tca ggc gga        438
Val Tyr Pro Leu Ala Pro Gly Ser Ser Gly Gly Gly Gly Ser Gly Gly
            125                 130                 135 ggt ggc tct ggc ggt agt gca ctg gat att gtg ctg aca caa tct cca        486
Gly Gly Ser Gly Gly Ser Ala Leu Asp Ile Val Leu Thr Gln Ser Pro
        140                 145                 150 ctc act ttg tcg gtt aac att ggt caa cca gcc tct atc tct tgc aag        534
Leu Thr Leu Ser Val Asn Ile Gly Gln Pro Ala Ser Ile Ser Cys Lys
    155                 160                 165 tca agt cag agc ctc tta tat act aat gga aaa acc tat ttt aat tgg        582
Ser Ser Gln Ser Leu Leu Tyr Thr Asn Gly Lys Thr Tyr Phe Asn Trp
170                 175                 180                 185 tta tta cag agg cca ggc cag tct cca aag cgc cta atc tat ctg gtg        630
Leu Leu Gln Arg Pro Gly Gln Ser Pro Lys Arg Leu Ile Tyr Leu Val
                190                 195                 200 tct aaa ctg gac tct gga gtc cct gac agg ttc act ggc agt gga tca        678
Ser Lys Leu Asp Ser Gly Val Pro Asp Arg Phe Thr Gly Ser Gly Ser
            205                 210                 215 gga aca gat ttt aca ctg aaa atc agc aga gtg gag gct gaa gat ttg        726
Gly Thr Asp Phe Thr Leu Lys Ile Ser Arg Val Glu Ala Glu Asp Leu
        220                 225                 230 gga gtt tat tac tgc gcg caa ggt aca cat ttt ccg tgg acg ttc ggt        774
Gly Val Tyr Tyr Cys Ala Gln Gly Thr His Phe Pro Trp Thr Phe Gly
    235                 240                 245 gga ggg acc aag ctg gaa atc aaa cgg gct gat gct gca cca act gta        822
Gly Gly Thr Lys Leu Glu Ile Lys Arg Ala Asp Ala Ala Pro Thr Val
250                 255                 260                 265 tcc gcg gcc gca gaa caa aaa ctc atc tca gaa gag gat ctg aat ggg        870
Ser Ala Ala Ala Glu Gln Lys Leu Ile Ser Glu Glu Asp Leu Asn Gly
                270                 275                 280 gcc gca tag                                                            879
Ala Ala <210> SEQ ID NO 6
<211> LENGTH: 283
<212> TYPE: PRT
<213> ORGANISM: Artificial Sequence
<220> FEATURE:
<223> OTHER INFORMATION: Synthetic Construct
    [CDS]:28..879 from SEQ ID NO 5

<400> SEQUENCE: 6

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Val His Trp Val Lys Gln Ser His Gly Lys Ser Leu Glu Trp Ile
        35                  40                  45

Gly Gly Ile Asn Pro Asn Gly Gly Thr Thr Tyr Asn Gln Lys Phe Lys
    50                  55                  60

Gly Lys Ala Thr Leu Thr Ile Asp Lys Ser Ser Ser Ala Phe Met
65                  70                  75                  80

Glu Leu Arg Ser Leu Thr Ser Glu Asp Ser Ala Val Tyr Tyr Phe Ala
            85                  90                  95

Thr Gly Trp Gly Pro Asp Tyr Trp Gly Gln Gly Thr Thr Leu Thr Val
        100                 105                 110

Ser Ser Ala Lys Thr Thr Pro Pro Ser Val Tyr Pro Leu Ala Pro Gly
    115                 120                 125
```

```
Ser Ser Gly Gly Gly Gly Ser Gly Gly Gly Ser Gly Gly Ser Ala
    130                 135                 140

Leu Asp Ile Val Leu Thr Gln Ser Pro Leu Thr Leu Ser Val Asn Ile
145                 150                 155                 160

Gly Gln Pro Ala Ser Ile Ser Cys Lys Ser Ser Gln Ser Leu Leu Tyr
                165                 170                 175

Thr Asn Gly Lys Thr Tyr Phe Asn Trp Leu Leu Gln Arg Pro Gly Gln
            180                 185                 190

Ser Pro Lys Arg Leu Ile Tyr Leu Val Ser Lys Leu Asp Ser Gly Val
        195                 200                 205

Pro Asp Arg Phe Thr Gly Ser Gly Ser Gly Thr Asp Phe Thr Leu Lys
    210                 215                 220

Ile Ser Arg Val Glu Ala Glu Asp Leu Gly Val Tyr Tyr Cys Ala Gln
225                 230                 235                 240

Gly Thr His Phe Pro Trp Thr Phe Gly Gly Gly Thr Lys Leu Glu Ile
                245                 250                 255

Lys Arg Ala Asp Ala Ala Pro Thr Val Ser Ala Ala Glu Gln Lys
            260                 265                 270

Leu Ile Ser Glu Glu Asp Leu Asn Gly Ala Ala
        275                 280
```

<210> SEQ ID NO 7
<211> LENGTH: 381
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: 1..381
<223> OTHER INFORMATION: /note="hERG1-Cys VH domain"
    /transl_table=1

<400> SEQUENCE: 7

```
gag gtc caa ctg caa cag tct gga cct gaa ctg gtg aag cct ggg gct      48
Glu Val Gln Leu Gln Gln Ser Gly Pro Glu Leu Val Lys Pro Gly Ala
1               5                   10                  15 tct gtg aag ata tcc tgc aag act tca gga tac aca ttc act gaa tac      96
Ser Val Lys Ile Ser Cys Lys Thr Ser Gly Tyr Thr Phe Thr Glu Tyr
            20                  25                  30 acc gtt cac tgg gtg aaa cag agc cat gga aag agc ctt gaa tgg att     144
Thr Val His Trp Val Lys Gln Ser His Gly Lys Ser Leu Glu Trp Ile
        35                  40                  45 gga ggc att aat cct aat ggt ggt act acc tat aat cag aag ttc aag     192
Gly Gly Ile Asn Pro Asn Gly Gly Thr Thr Tyr Asn Gln Lys Phe Lys
    50                  55                  60 ggc aag gcc aca ttg act att gac aag tcc tcc agc tca gcc ttc atg     240
Gly Lys Ala Thr Leu Thr Ile Asp Lys Ser Ser Ser Ser Ala Phe Met
65                  70                  75                  80 gag ctc cgc agc ctg aca tct gag gat tct gca gtc tat tac tgy gca     288
Glu Leu Arg Ser Leu Thr Ser Glu Asp Ser Ala Val Tyr Tyr Cys Ala
                85                  90                  95 aca ggt tgg gga cct gac tac tgg ggc caa ggc acc act ctc aca gtc     336
Thr Gly Trp Gly Pro Asp Tyr Trp Gly Gln Gly Thr Thr Leu Thr Val
            100                 105                 110 tcc tca gcc aaa aca aca ccc cca tca gtc tat cca ctg gcc cct         381
Ser Ser Ala Lys Thr Thr Pro Pro Ser Val Tyr Pro Leu Ala Pro
        115                 120                 125
```

<210> SEQ ID NO 8

```
<211> LENGTH: 127
<212> TYPE: PRT
<213> ORGANISM: Artificial Sequence
<220> FEATURE:
<223> OTHER INFORMATION: Synthetic Construct
      [CDS]:1..381 from SEQ ID NO 7

<400> SEQUENCE: 8

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Val His Trp Val Lys Gln Ser His Gly Lys Ser Leu Glu Trp Ile
        35                  40                  45

Gly Gly Ile Asn Pro Asn Gly Gly Thr Thr Tyr Asn Gln Lys Phe Lys
    50                  55                  60

Gly Lys Ala Thr Leu Thr Ile Asp Lys Ser Ser Ser Ser Ala Phe Met
65                  70                  75                  80

Glu Leu Arg Ser Leu Thr Ser Glu Asp Ser Ala Val Tyr Tyr Cys Ala
                85                  90                  95

Thr Gly Trp Gly Pro Asp Tyr Trp Gly Gln Gly Thr Thr Leu Thr Val
            100                 105                 110

Ser Ser Ala Lys Thr Thr Pro Pro Ser Val Tyr Pro Leu Ala Pro
        115                 120                 125

<210> SEQ ID NO 9
<211> LENGTH: 879
<212> TYPE: DNA
<213> ORGANISM: Artificial Sequence
<220> FEATURE:
<223> OTHER INFORMATION: anti-hERG1-Cys scFv
<220> FEATURE:
<221> NAME/KEY: CDS
<222> LOCATION: 28..879
<223> OTHER INFORMATION: /note="anti-hERG1-Cys scFv"
      /transl_table=1

<400> SEQUENCE: 9
atggcccagg tgcagctgca ggtcgac gag gtc caa ctg caa cag tct gga cct     54
                              Glu Val Gln Leu Gln Gln Ser Gly Pro
                              1               5 gaa ctg gtg aag cct ggg gct tct gtg aag ata tcc tgc aag act tca     102
Glu Leu Val Lys Pro Gly Ala Ser Val Lys Ile Ser Cys Lys Thr Ser
10                  15                  20                  25 gga tac aca ttc act gaa tac acc gtt cac tgg gtg aaa cag agc cat     150
Gly Tyr Thr Phe Thr Glu Tyr Thr Val His Trp Val Lys Gln Ser His
                30                  35                  40 gga aag agc ctt gaa tgg att gga ggc att aat cct aat ggt ggt act     198
Gly Lys Ser Leu Glu Trp Ile Gly Gly Ile Asn Pro Asn Gly Gly Thr
            45                  50                  55 acc tat aat cag aag ttc aag ggc aag gcc aca ttg act att gac aag     246
Thr Tyr Asn Gln Lys Phe Lys Gly Lys Ala Thr Leu Thr Ile Asp Lys
        60                  65                  70 tcc tcc agc tca gcc ttc atg gag ctc cgc agc ctg aca tct gag gat     294
Ser Ser Ser Ser Ala Phe Met Glu Leu Arg Ser Leu Thr Ser Glu Asp
    75                  80                  85 tct gca gtc tat tac tgy gca aca ggt tgg gga cct gac tac tgg ggc     342
Ser Ala Val Tyr Tyr Cys Ala Thr Gly Trp Gly Pro Asp Tyr Trp Gly
90                  95                  100                 105 caa ggc acc act ctc aca gtc tcc tca gcc aaa aca aca ccc cca tca     390
Gln Gly Thr Thr Leu Thr Val Ser Ser Ala Lys Thr Thr Pro Pro Ser
                110                 115                 120
```

| | | | | | | | | | | | | | | | | |
|---|---|---|---|---|---|---|---|---|---|---|---|---|---|---|---|---|
|gtc|tat|cca|ctg|gcc|cct|ggc|tcg|agt|ggt|gga|ggc|ggt|tca|ggc|gga|438|
|Val|Tyr|Pro|Leu|Ala|Pro|Gly|Ser|Ser|Gly|Gly|Gly|Gly|Ser|Gly|Gly| |
| | |125| | | |130| | | |135| | | | | | |

| | | | | | | | | | | | | | | | | |
|---|---|---|---|---|---|---|---|---|---|---|---|---|---|---|---|---|
|ggt|ggc|tct|ggc|ggt|agt|gca|ctg|gat|att|gtg|ctg|aca|caa|tct|cca|486|
|Gly|Gly|Ser|Gly|Gly|Ser|Ala|Leu|Asp|Ile|Val|Leu|Thr|Gln|Ser|Pro| |
| | |140| | | |145| | | |150| | | | | | |

| | | | | | | | | | | | | | | | | |
|---|---|---|---|---|---|---|---|---|---|---|---|---|---|---|---|---|
|ctc|act|ttg|tcg|gtt|aac|att|ggt|caa|cca|gcc|tct|atc|tct|tgc|aag|534|
|Leu|Thr|Leu|Ser|Val|Asn|Ile|Gly|Gln|Pro|Ala|Ser|Ile|Ser|Cys|Lys| |
| | |155| | | |160| | | |165| | | | | | |

| | | | | | | | | | | | | | | | | |
|---|---|---|---|---|---|---|---|---|---|---|---|---|---|---|---|---|
|tca|agt|cag|agc|ctc|tta|tat|act|aat|gga|aaa|acc|tat|ttt|aat|tgg|582|
|Ser|Ser|Gln|Ser|Leu|Leu|Tyr|Thr|Asn|Gly|Lys|Thr|Tyr|Phe|Asn|Trp| |
|170| | | | |175| | | | |180| | | | |185| |

| | | | | | | | | | | | | | | | | |
|---|---|---|---|---|---|---|---|---|---|---|---|---|---|---|---|---|
|tta|tta|cag|agg|cca|ggc|cag|tct|cca|aag|cgc|cta|atc|tat|ctg|gtg|630|
|Leu|Leu|Gln|Arg|Pro|Gly|Gln|Ser|Pro|Lys|Arg|Leu|Ile|Tyr|Leu|Val| |
| | | | |190| | | | |195| | | | |200| | |

| | | | | | | | | | | | | | | | | |
|---|---|---|---|---|---|---|---|---|---|---|---|---|---|---|---|---|
|tct|aaa|ctg|gac|tct|gga|gtc|cct|gac|agg|ttc|act|ggc|agt|gga|tca|678|
|Ser|Lys|Leu|Asp|Ser|Gly|Val|Pro|Asp|Arg|Phe|Thr|Gly|Ser|Gly|Ser| |
| | | |205| | | |210| | | |215| | | | | |

| | | | | | | | | | | | | | | | | |
|---|---|---|---|---|---|---|---|---|---|---|---|---|---|---|---|---|
|gga|aca|gat|ttt|aca|ctg|aaa|atc|agc|aga|gtg|gag|gct|gaa|gat|ttg|726|
|Gly|Thr|Asp|Phe|Thr|Leu|Lys|Ile|Ser|Arg|Val|Glu|Ala|Glu|Asp|Leu| |
| | |220| | | |225| | | |230| | | | | | |

| | | | | | | | | | | | | | | | | |
|---|---|---|---|---|---|---|---|---|---|---|---|---|---|---|---|---|
|gga|gtt|tat|tac|tgc|gcg|caa|ggt|aca|cat|ttt|ccg|tgg|acg|ttc|ggt|774|
|Gly|Val|Tyr|Tyr|Cys|Ala|Gln|Gly|Thr|His|Phe|Pro|Trp|Thr|Phe|Gly| |
| |235| | | |240| | | |245| | | | | | | |

| | | | | | | | | | | | | | | | | |
|---|---|---|---|---|---|---|---|---|---|---|---|---|---|---|---|---|
|gga|ggg|acc|aag|ctg|gaa|atc|aaa|cgg|gct|gat|gct|gca|cca|act|gta|822|
|Gly|Gly|Thr|Lys|Leu|Glu|Ile|Lys|Arg|Ala|Asp|Ala|Ala|Pro|Thr|Val| |
|250| | | |255| | | |260| | | |265| | | | |

| | | | | | | | | | | | | | | | | |
|---|---|---|---|---|---|---|---|---|---|---|---|---|---|---|---|---|
|tcc|gcg|gcc|gca|gaa|caa|aaa|ctc|atc|tca|gaa|gag|gat|ctg|aat|ggg|870|
|Ser|Ala|Ala|Ala|Glu|Gln|Lys|Leu|Ile|Ser|Glu|Glu|Asp|Leu|Asn|Gly| |
| | |270| | | |275| | | |280| | | | | | |

| | | |
|---|---|---|
|gcc|gca|tag|879|
|Ala|Ala| | |

```
<210> SEQ ID NO 10
<211> LENGTH: 283
<212> TYPE: PRT
<213> ORGANISM: Artificial Sequence
<220> FEATURE:
<223> OTHER INFORMATION: Synthetic Construct
      [CDS]:28..879 from SEQ ID NO 9

<400> SEQUENCE: 10
```

| | | | | | | | | | | | | | | |
|---|---|---|---|---|---|---|---|---|---|---|---|---|---|---|
|Glu|Val|Gln|Leu|Gln|Gln|Ser|Gly|Pro|Glu|Leu|Val|Lys|Pro|Gly|Ala|
|1| | | |5| | | | |10| | | | |15|

| | | | | | | | | | | | | | | |
|---|---|---|---|---|---|---|---|---|---|---|---|---|---|---|
|Ser|Val|Lys|Ile|Ser|Cys|Lys|Thr|Ser|Gly|Tyr|Thr|Phe|Thr|Glu|Tyr|
| | | |20| | | | |25| | | | |30| |

| | | | | | | | | | | | | | | |
|---|---|---|---|---|---|---|---|---|---|---|---|---|---|---|
|Thr|Val|His|Trp|Val|Lys|Gln|Ser|His|Gly|Lys|Ser|Leu|Glu|Trp|Ile|
| | |35| | | | |40| | | | |45| | |

| | | | | | | | | | | | | | | |
|---|---|---|---|---|---|---|---|---|---|---|---|---|---|---|
|Gly|Gly|Ile|Asn|Pro|Asn|Gly|Gly|Thr|Thr|Tyr|Asn|Gln|Lys|Phe|Lys|
| |50| | | | |55| | | | |60| | | |

| | | | | | | | | | | | | | | |
|---|---|---|---|---|---|---|---|---|---|---|---|---|---|---|
|Gly|Lys|Ala|Thr|Leu|Thr|Ile|Asp|Lys|Ser|Ser|Ser|Ala|Phe|Met|
|65| | | | |70| | | | |75| | | | |80|

| | | | | | | | | | | | | | | |
|---|---|---|---|---|---|---|---|---|---|---|---|---|---|---|
|Glu|Leu|Arg|Ser|Leu|Thr|Ser|Glu|Asp|Ser|Ala|Val|Tyr|Tyr|Cys|Ala|
| | | | |85| | | | |90| | | | |95|

| | | | | | | | | | | | | | | |
|---|---|---|---|---|---|---|---|---|---|---|---|---|---|---|
|Thr|Gly|Trp|Gly|Pro|Asp|Tyr|Trp|Gly|Gln|Gly|Thr|Thr|Leu|Thr|Val|
| | | |100| | | | |105| | | | |110| |

| | | | | | | | | | | | | | | |
|---|---|---|---|---|---|---|---|---|---|---|---|---|---|---|
|Ser|Ser|Ala|Lys|Thr|Thr|Pro|Pro|Ser|Val|Tyr|Pro|Leu|Ala|Pro|Gly|
| | |115| | | | |120| | | | |125| | |

```
Ser Ser Gly Gly Gly Gly Ser Gly Gly Gly Ser Gly Gly Ser Ala
    130                 135                 140

Leu Asp Ile Val Leu Thr Gln Ser Pro Leu Thr Leu Ser Val Asn Ile
145                 150                 155                 160

Gly Gln Pro Ala Ser Ile Ser Cys Lys Ser Gln Ser Leu Leu Tyr
                165                 170                 175

Thr Asn Gly Lys Thr Tyr Phe Asn Trp Leu Leu Gln Arg Pro Gly Gln
                180                 185                 190

Ser Pro Lys Arg Leu Ile Tyr Leu Val Ser Lys Leu Asp Ser Gly Val
        195                 200                 205

Pro Asp Arg Phe Thr Gly Ser Gly Ser Gly Thr Asp Phe Thr Leu Lys
    210                 215                 220

Ile Ser Arg Val Glu Ala Glu Asp Leu Gly Val Tyr Tyr Cys Ala Gln
225                 230                 235                 240

Gly Thr His Phe Pro Trp Thr Phe Gly Gly Gly Thr Lys Leu Glu Ile
                245                 250                 255

Lys Arg Ala Asp Ala Ala Pro Thr Val Ser Ala Ala Glu Gln Lys
            260                 265                 270

Leu Ile Ser Glu Glu Asp Leu Asn Gly Ala Ala
        275                 280
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..20
<223> OTHER INFORMATION: /note="primer degVH forward"

<400> SEQUENCE: 11
gaggtccarc tgcaacartc                                          20

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..24
<223> OTHER INFORMATION: /note="primer IgG2 reverse"

<400> SEQUENCE: 12
aggggccagt ggatagactg atgg                                     24

<210> SEQ ID NO 13
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..24
<223> OTHER INFORMATION: /note="primer degVL(K)"

<400> SEQUENCE: 13
gayattgtgm tsacmcarwc tmca                                     24
```

```
<210> SEQ ID NO 14
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..21
<223> OTHER INFORMATION: /note="primer K reverse"

<400> SEQUENCE: 14
ggatacagtt ggtgcagcat c                                        21

<210> SEQ ID NO 15
<211> LENGTH: 36
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..36
<223> OTHER INFORMATION: /note="primer forward VL-ApaLI"

<400> SEQUENCE: 15
acgcgtgcac tggatattgt gctgacacaa tctcca                        36

<210> SEQ ID NO 16
<211> LENGTH: 37
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..37
<223> OTHER INFORMATION: /note="primer reverse VL-NotI"

<400> SEQUENCE: 16
ataagaatgc ggccgcggat acagttggtg cagcatc                       37

<210> SEQ ID NO 17
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..30
<223> OTHER INFORMATION: /note="forward VH-SalI"

<400> SEQUENCE: 17
acgcgtcgac gaggtccaac tgcaacagtc                               30

<210> SEQ ID NO 18
<211> LENGTH: 35
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..35
<223> OTHER INFORMATION: /note="primer reverse VH-XhoI"

<400> SEQUENCE: 18
ccgctcgagc caggggccag tggatagact gatgg                         35
```

```
<210> SEQ ID NO 19
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..30
<223> OTHER INFORMATION: /note="primer forward VH-FspI"

<400> SEQUENCE: 19
aaaatgcgca gaggtccaac tgcaacagtc                                30

<210> SEQ ID NO 20
<211> LENGTH: 31
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..31
<223> OTHER INFORMATION: /note="primer reverse VL- AvrII"

<400> SEQUENCE: 20
ggggcctagg ggatacagtt ggtgcagcat c                              31

<210> SEQ ID NO 21
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..41
<223> OTHER INFORMATION: /note="Cys left primer"

<400> SEQUENCE: 21
ggattctgca gtctattact gtgcaacagg ttggggacct g                   41

<210> SEQ ID NO 22
<211> LENGTH: 41
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1..41
<223> OTHER INFORMATION: /note="Cys right primer"

<400> SEQUENCE: 22
caggtcccca acctgttgca cagtaataga ctgcagaatc c                   41

<210> SEQ ID NO 23
<211> LENGTH: 351
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: 1..351
<223> OTHER INFORMATION: /note="TS2/16 VL"
      /transl_table=1
```

<400> SEQUENCE: 23

```
gat att gtg atg aca cag act cca acc acc atg gct gca tct ccc ggg        48
Asp Ile Val Met Thr Gln Thr Pro Thr Thr Met Ala Ala Ser Pro Gly
1               5                   10                  15 gac aag atc act atc acc tgc agt gtc agt tca att ata agt tcc aat        96
Asp Lys Ile Thr Ile Thr Cys Ser Val Ser Ser Ile Ile Ser Ser Asn
            20                  25                  30 tac ctg cat tgg tat agt cag aag cca gga ttc tcc cct aaa ctc ttg       144
Tyr Leu His Trp Tyr Ser Gln Lys Pro Gly Phe Ser Pro Lys Leu Leu
        35                  40                  45 att tat agg aca tcc aat ctg gct tct gga gtc cca cct cgc ttc agt       192
Ile Tyr Arg Thr Ser Asn Leu Ala Ser Gly Val Pro Pro Arg Phe Ser
    50                  55                  60 ggc agt ggg tct ggg acc tct tac tct ctc aca att ggc acc atg gag       240
Gly Ser Gly Ser Gly Thr Ser Tyr Ser Leu Thr Ile Gly Thr Met Glu
65                  70                  75                  80 gct gaa gat gtt gcc act tac tac tgc cag cag ggt tct gat att cca       288
Ala Glu Asp Val Ala Thr Tyr Tyr Cys Gln Gln Gly Ser Asp Ile Pro
                85                  90                  95 ctc acg ttc ggt gat ggg acc aag ctg gac ctg aaa cgg gct gat gct       336
Leu Thr Phe Gly Asp Gly Thr Lys Leu Asp Leu Lys Arg Ala Asp Ala
            100                 105                 110 gca cca act gta tcc                                                   351
Ala Pro Thr Val Ser
        115
```

<210> SEQ ID NO 24
<211> LENGTH: 117
<212> TYPE: PRT
<213> ORGANISM: Artificial Sequence
<220> FEATURE:
<223> OTHER INFORMATION: Synthetic Construct
      [CDS]:1..351 from SEQ ID NO 23

<400> SEQUENCE: 24

```
Asp Ile Val Met Thr Gln Thr Pro Thr Thr Met Ala Ala Ser Pro Gly
1               5                   10                  15

Asp Lys Ile Thr Ile Thr Cys Ser Val Ser Ser Ile Ile Ser Ser Asn
            20                  25                  30

Tyr Leu His Trp Tyr Ser Gln Lys Pro Gly Phe Ser Pro Lys Leu Leu
        35                  40                  45

Ile Tyr Arg Thr Ser Asn Leu Ala Ser Gly Val Pro Pro Arg Phe Ser
    50                  55                  60

Gly Ser Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Ser Asp Ile Pro
                85                  90                  95

Leu Thr Phe Gly Asp Gly Thr Lys Leu Asp Leu Lys Arg Ala Asp Ala
            100                 105                 110

Ala Pro Thr Val Ser
        115
```

<210> SEQ ID NO 25
<211> LENGTH: 387
<212> TYPE: DNA
<213> ORGANISM: Artificial Sequence
<220> FEATURE:
<223> OTHER INFORMATION: Synthetic Construct
<220> FEATURE:
<221> NAME/KEY: CDS

```
<222> LOCATION: 1..387
<223> OTHER INFORMATION: /note="TS2/16 VH"
      /transl_table=1

<400> SEQUENCE: 25 gag gtg aag gtg gtg gaa tct ggg gga ggc tta gtg aag cct gga ggg      48
Glu Val Lys Val Val Glu Ser Gly Gly Gly Leu Val Lys Pro Gly Gly
1               5                   10                  15 tcc ctg aaa ctc tcc tgt gca gcc tct gga ttc act ttc agt agc tat      96
Ser Leu Lys Leu Ser Cys Ala Ala Ser Gly Phe Thr Phe Ser Ser Tyr
            20                  25                  30 acc atg tct tgg gtt cgc cag act ccg gag aag agg ctg gag tgg gtc     144
Thr Met Ser Trp Val Arg Gln Thr Pro Glu Lys Arg Leu Glu Trp Val
        35                  40                  45 gca acc ata agt agt ggt ggt tct tac acc tac tat cca gac agt gtg     192
Ala Thr Ile Ser Ser Gly Gly Ser Tyr Thr Tyr Tyr Pro Asp Ser Val
50                  55                  60 aag ggc cga ttc acc att tcc aga gac aaa gcc aag aac acc ctg tat     240
Lys Gly Arg Phe Thr Ile Ser Arg Asp Lys Ala Lys Asn Thr Leu Tyr
65                  70                  75                  80 ttg caa atg ggc agt ctg aag tct gag gac aca gcc atg tat tac tgt     288
Leu Gln Met Gly Ser Leu Lys Ser Glu Asp Thr Ala Met Tyr Tyr Cys
                85                  90                  95 aca aga ata ggt tac gac gaa gat tat gct atg gac cac tgg ggt caa     336
Thr Arg Ile Gly Tyr Asp Glu Asp Tyr Ala Met Asp His Trp Gly Gln
            100                 105                 110 gga acc tca gtc acc gtc tcc tca gcc aaa acg aca ccc cca tct gtc     384
Gly Thr Ser Val Thr Val Ser Ser Ala Lys Thr Thr Pro Pro Ser Val
        115                 120                 125 tat                                                                  387
Tyr

<210> SEQ ID NO 26
<211> LENGTH: 129
<212> TYPE: PRT
<213> ORGANISM: Artificial Sequence
<220> FEATURE:
<223> OTHER INFORMATION: Synthetic Construct
      [CDS]:1..387 from SEQ ID NO 25

<400> SEQUENCE: 26

Glu Val Lys Val Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Ser Tyr Thr Tyr Tyr Pro Asp Ser Val
50                  55                  60

Lys Gly Arg Phe Thr Ile Ser Arg Asp Lys Ala Lys Asn Thr Leu Tyr
65                  70                  75                  80

Leu Gln Met Gly Ser Leu Lys Ser Glu Asp Thr Ala Met Tyr Tyr Cys
                85                  90                  95

Thr Arg Ile Gly Tyr Asp Glu Asp Tyr Ala Met Asp His Trp Gly Gln
            100                 105                 110

Gly Thr Ser Val Thr Val Ser Ser Ala Lys Thr Thr Pro Pro Ser Val
        115                 120                 125

Tyr
```

-continued

```
<210> SEQ ID NO 27
<211> LENGTH: 39
<212> TYPE: DNA
<213> ORGANISM: Artificial Sequence
<220> FEATURE:
<223> OTHER INFORMATION: Synthetic Construct
<220> FEATURE:
<221> NAME/KEY: misc_signal
<222> LOCATION: 5..10
<223> OTHER INFORMATION: /note="restriction site VL FspI"

<400> SEQUENCE: 27
aaaatgcgca gactacaaag atattgtgat gacacagac                              39

<210> SEQ ID NO 28
<211> LENGTH: 50
<212> TYPE: DNA
<213> ORGANISM: Artificial Sequence
<220> FEATURE:
<223> OTHER INFORMATION: Synthetic Construct
<220> FEATURE:
<221> NAME/KEY: misc_signal
<222> LOCATION: 5..10
<223> OTHER INFORMATION: /note="restriction site AvrII"

<400> SEQUENCE: 28
ggggcctagg atagacagat gggggtgtcg cgacaccccc atctgtctat                  50

<210> SEQ ID NO 29
<211> LENGTH: 1662
<212> TYPE: DNA
<213> ORGANISM: Artificial Sequence
<220> FEATURE:
<223> OTHER INFORMATION: Synthetic Construct
<220> FEATURE:
<221> NAME/KEY: CDS
<222> LOCATION: 1..1662
<223> OTHER INFORMATION: /note="scDb-hERG1-beta1"
      /transl_table=1

<400> SEQUENCE: 29 gag gct gag tgc gca gac gag gtc caa ctg caa cag tct gga cct gaa        48
Glu Ala Glu Cys Ala Asp Glu Val Gln Leu Gln Gln Ser Gly Pro Glu
1               5                   10                  15 ctg gtg aag cct ggg gct tct gtg aag ata tcc tgc aag act tca gga        96
Leu Val Lys Pro Gly Ala Ser Val Lys Ile Ser Cys Lys Thr Ser Gly
            20                  25                  30 tac aca ttc act gaa tac acc gtt cac tgg gtg aaa cag agc cat gga       144
Tyr Thr Phe Thr Glu Tyr Thr Val His Trp Val Lys Gln Ser His Gly
        35                  40                  45 aag agc ctt gaa tgg att gga ggc att aat cct aat ggt ggt act acc       192
Lys Ser Leu Glu Trp Ile Gly Gly Ile Asn Pro Asn Gly Gly Thr Thr
    50                  55                  60 tat aat cag aag ttc aag ggc aag gcc aca ttg act att gac aag tcc       240
Tyr Asn Gln Lys Phe Lys Gly Lys Ala Thr Leu Thr Ile Asp Lys Ser
65                  70                  75                  80 tcc agc tca gcc ttc atg gag ctc cgc agc ctg aca tct gag gat tct       288
Ser Ser Ser Ala Phe Met Glu Leu Arg Ser Leu Thr Ser Glu Asp Ser
                85                  90                  95 gca gtc tat tac tgt gca aca ggt tgg gga cct gac tac tgg ggc caa       336
Ala Val Tyr Tyr Cys Ala Thr Gly Trp Gly Pro Asp Tyr Trp Gly Gln
            100                 105                 110 ggc acc act ctc aca gtc tcc tca gcc aaa aca aca ccc cca tca gtc       384
Gly Thr Thr Leu Thr Val Ser Ser Ala Lys Thr Thr Pro Pro Ser Val
        115                 120                 125
```

```
tat cca ctg gcc cct ggc tcg agt gat att gtg atg aca cag act cca    432
Tyr Pro Leu Ala Pro Gly Ser Ser Asp Ile Val Met Thr Gln Thr Pro
    130                 135                 140 acc acc atg gct gca tct ccc ggg gac aag atc act atc acc tgc agt    480
Thr Thr Met Ala Ala Ser Pro Gly Asp Lys Ile Thr Ile Thr Cys Ser
145                 150                 155                 160 gtc agt tca att ata agt tcc aat tac ctg cat tgg tat agt cag aag    528
Val Ser Ser Ile Ile Ser Ser Asn Tyr Leu His Trp Tyr Ser Gln Lys
                165                 170                 175 cca gga ttc tcc cct aaa ctc ttg att tat agg aca tcc aat ctg gct    576
Pro Gly Phe Ser Pro Lys Leu Leu Ile Tyr Arg Thr Ser Asn Leu Ala
            180                 185                 190 tct gga gtc cca cct cgc ttc agt ggc agt ggg tct ggg acc tct tac    624
Ser Gly Val Pro Pro Arg Phe Ser Gly Ser Gly Ser Gly Thr Ser Tyr
        195                 200                 205 tct ctc aca att ggc acc atg gag gct gaa gat gtt gcc act tac tac    672
Ser Leu Thr Ile Gly Thr Met Glu Ala Glu Asp Val Ala Thr Tyr Tyr
    210                 215                 220 tgc cag cag ggt tct gat att cca ctc acg ttc ggt gat ggg acc aag    720
Cys Gln Gln Gly Ser Asp Ile Pro Leu Thr Phe Gly Asp Gly Thr Lys
225                 230                 235                 240 ctg gac ctg aaa cgg gct gat gct gca cca act gta tcc ggt ggt ggt    768
Leu Asp Leu Lys Arg Ala Asp Ala Ala Pro Thr Val Ser Gly Gly Gly
                245                 250                 255 ggt tct ggt ggt ggt ggt tct ggc ggc ggc ggc tcc ggt ggt ggt gga    816
Gly Ser Gly Gly Gly Gly Ser Gly Gly Gly Gly Ser Gly Gly Gly Gly
            260                 265                 270 tcc gag gtg aag gtg gtg gaa tct ggg gga ggc tta gtg aag cct gga    864
Ser Glu Val Lys Val Val Glu Ser Gly Gly Gly Leu Val Lys Pro Gly
        275                 280                 285 ggg tcc ctg aaa ctc tcc tgt gca gcc tct gga ttc act ttc agt agc    912
Gly Ser Leu Lys Leu Ser Cys Ala Ala Ser Gly Phe Thr Phe Ser Ser
    290                 295                 300 tat acc atg tct tgg gtt cgc cag act ccg gag aag agg ctg gag tgg    960
Tyr Thr Met Ser Trp Val Arg Gln Thr Pro Glu Lys Arg Leu Glu Trp
305                 310                 315                 320 gtc gca acc ata agt agt ggt ggt tct tac acc tac tat cca gac agt   1008
Val Ala Thr Ile Ser Ser Gly Gly Ser Tyr Thr Tyr Tyr Pro Asp Ser
                325                 330                 335 gtg aag ggc cga ttc acc att tcc aga gac aaa gcc aag aac acc ctg   1056
Val Lys Gly Arg Phe Thr Ile Ser Arg Asp Lys Ala Lys Asn Thr Leu
            340                 345                 350 tat ttg caa atg ggc agt ctg aag tct gag gac aca gcc atg tat tac   1104
Tyr Leu Gln Met Gly Ser Leu Lys Ser Glu Asp Thr Ala Met Tyr Tyr
        355                 360                 365 tgt aca aga ata ggt tac gac gaa gat tat gct atg gac cac tgg ggt   1152
Cys Thr Arg Ile Gly Tyr Asp Glu Asp Tyr Ala Met Asp His Trp Gly
    370                 375                 380 caa gga acc tca gtc acc gtc tcc tca gcc aaa acg aca ccc cca tct   1200
Gln Gly Thr Ser Val Thr Val Ser Ser Ala Lys Thr Thr Pro Pro Ser
385                 390                 395                 400 gtc tat agt gca ctg gat att gtg ctg aca caa tct cca ctc act ttg   1248
Val Tyr Ser Ala Leu Asp Ile Val Leu Thr Gln Ser Pro Leu Thr Leu
                405                 410                 415 tcg gtt aac att ggt caa cca gcc tct atc tct tgc aag tca agt cag   1296
Ser Val Asn Ile Gly Gln Pro Ala Ser Ile Ser Cys Lys Ser Ser Gln
            420                 425                 430
```

|   |   |   |   |   |   |   |   |   |   |   |   |   |   |   |   |   |
|---|---|---|---|---|---|---|---|---|---|---|---|---|---|---|---|---|
| agc | ctc | tta | tat | act | aat | gga | aaa | acc | tat | ttt | aat | tgg | tta | tta | cag | 1344 |
| Ser | Leu | Leu | Tyr | Thr | Asn | Gly | Lys | Thr | Tyr | Phe | Asn | Trp | Leu | Leu | Gln | |
| | 435 | | | | | 440 | | | | | 445 | | | | | |
| agg | cca | ggc | cag | tct | cca | aag | cgc | cta | atc | tat | ctg | gtg | tct | aaa | ctg | 1392 |
| Arg | Pro | Gly | Gln | Ser | Pro | Lys | Arg | Leu | Ile | Tyr | Leu | Val | Ser | Lys | Leu | |
| 450 | | | | | 455 | | | | | 460 | | | | | | |
| gac | tct | gga | gtc | cct | gac | agg | ttc | act | ggc | agt | gga | tca | gga | aca | gat | 1440 |
| Asp | Ser | Gly | Val | Pro | Asp | Arg | Phe | Thr | Gly | Ser | Gly | Ser | Gly | Thr | Asp | |
| 465 | | | | 470 | | | | | 475 | | | | | 480 | | |
| ttt | aca | ctg | aaa | atc | agc | aga | gtg | gag | gct | gaa | gat | ttg | gga | gtt | tat | 1488 |
| Phe | Thr | Leu | Lys | Ile | Ser | Arg | Val | Glu | Ala | Glu | Asp | Leu | Gly | Val | Tyr | |
| | | | | 485 | | | | | 490 | | | | | 495 | | |
| tac | tgc | gcg | caa | ggt | aca | cat | ttt | ccg | tgg | acg | ttc | ggt | gga | ggg | acc | 1536 |
| Tyr | Cys | Ala | Gln | Gly | Thr | His | Phe | Pro | Trp | Thr | Phe | Gly | Gly | Gly | Thr | |
| | | 500 | | | | | 505 | | | | | 510 | | | | |
| aag | ctg | gaa | atc | aaa | cgg | gct | gat | gct | gca | cca | act | gta | tcc | gcg | gcc | 1584 |
| Lys | Leu | Glu | Ile | Lys | Arg | Ala | Asp | Ala | Ala | Pro | Thr | Val | Ser | Ala | Ala | |
| | | 515 | | | | | 520 | | | | | 525 | | | | |
| gca | gaa | caa | aaa | ctc | atc | tca | gaa | gag | gat | ctg | aat | ggg | gcc | cct | agg | 1632 |
| Ala | Glu | Gln | Lys | Leu | Ile | Ser | Glu | Glu | Asp | Leu | Asn | Gly | Ala | Pro | Arg | |
| 530 | | | | | 535 | | | | | 540 | | | | | | |
| cat | cat | cac | cat | cac | cat | cat | cac | taa | tag | | | | | | | 1662 |
| His | His | His | His | His | His | His | His | | | | | | | | | |
| 545 | | | | | 550 | | | | | | | | | | | |

```
<210> SEQ ID NO 30
<211> LENGTH: 552
<212> TYPE: PRT
<213> ORGANISM: Artificial Sequence
<220> FEATURE:
<223> OTHER INFORMATION: Synthetic Construct
      [CDS]:1..1662 from SEQ ID NO 29

<400> SEQUENCE: 30
```

| Glu | Ala | Glu | Cys | Ala | Asp | Glu | Val | Gln | Leu | Gln | Gln | Ser | Gly | Pro | Glu |
|-----|-----|-----|-----|-----|-----|-----|-----|-----|-----|-----|-----|-----|-----|-----|-----|
| 1 | | | | 5 | | | | | 10 | | | | | 15 | |
| Leu | Val | Lys | Pro | Gly | Ala | Ser | Val | Lys | Ile | Ser | Cys | Lys | Thr | Ser | Gly |
| | | | 20 | | | | | 25 | | | | | 30 | | |
| Tyr | Thr | Phe | Thr | Glu | Tyr | Thr | Val | His | Trp | Val | Lys | Gln | Ser | His | Gly |
| | | | 35 | | | | | 40 | | | | | 45 | | |
| Lys | Ser | Leu | Glu | Trp | Ile | Gly | Gly | Ile | Asn | Pro | Asn | Gly | Gly | Thr | Thr |
| | 50 | | | | | 55 | | | | | 60 | | | | |
| Tyr | Asn | Gln | Lys | Phe | Lys | Gly | Lys | Ala | Thr | Leu | Thr | Ile | Asp | Lys | Ser |
| 65 | | | | | 70 | | | | | 75 | | | | | 80 |
| Ser | Ser | Ser | Ala | Phe | Met | Glu | Leu | Arg | Ser | Leu | Thr | Ser | Glu | Asp | Ser |
| | | | | 85 | | | | | 90 | | | | | 95 | |
| Ala | Val | Tyr | Tyr | Cys | Ala | Thr | Gly | Trp | Gly | Pro | Asp | Tyr | Trp | Gly | Gln |
| | | | 100 | | | | | 105 | | | | | 110 | | |
| Gly | Thr | Thr | Leu | Thr | Val | Ser | Ser | Ala | Lys | Thr | Thr | Pro | Pro | Ser | Val |
| | | | 115 | | | | | 120 | | | | | 125 | | |
| Tyr | Pro | Leu | Ala | Pro | Gly | Ser | Ser | Asp | Ile | Val | Met | Thr | Gln | Thr | Pro |
| | | 130 | | | | | 135 | | | | | 140 | | | |
| Thr | Thr | Met | Ala | Ala | Ser | Pro | Gly | Asp | Lys | Ile | Thr | Ile | Thr | Cys | Ser |
| 145 | | | | | 150 | | | | | 155 | | | | | 160 |
| Val | Ser | Ser | Ile | Ile | Ser | Ser | Asn | Tyr | Leu | His | Trp | Tyr | Ser | Gln | Lys |
| | | | | 165 | | | | | 170 | | | | | 175 | |
| Pro | Gly | Phe | Ser | Pro | Lys | Leu | Leu | Ile | Tyr | Arg | Thr | Ser | Asn | Leu | Ala |
| | | | 180 | | | | | 185 | | | | | 190 | | |

Ser Gly Val Pro Pro Arg Phe Ser Gly Ser Gly Ser Gly Thr Ser Tyr
          195                 200                 205

Ser Leu Thr Ile Gly Thr Met Glu Ala Glu Asp Val Ala Thr Tyr Tyr
        210                 215                 220

Cys Gln Gln Gly Ser Asp Ile Pro Leu Thr Phe Gly Asp Gly Thr Lys
225                 230                 235                 240

Leu Asp Leu Lys Arg Ala Asp Ala Ala Pro Thr Val Ser Gly Gly Gly
                245                 250                 255

Gly Ser Gly Gly Gly Gly Ser Gly Gly Gly Gly Ser Gly Gly Gly Gly
            260                 265                 270

Ser Glu Val Lys Val Glu Ser Gly Gly Gly Leu Val Lys Pro Gly Gly
        275                 280                 285

Gly Ser Leu Lys Leu Ser Cys Ala Ala Ser Gly Phe Thr Phe Ser Ser
        290                 295                 300

Tyr Thr Met Ser Trp Val Arg Gln Thr Pro Glu Lys Arg Leu Glu Trp
305                 310                 315                 320

Val Ala Thr Ile Ser Ser Gly Gly Ser Tyr Thr Tyr Tyr Pro Asp Ser
                325                 330                 335

Val Lys Gly Arg Phe Thr Ile Ser Arg Asp Lys Ala Lys Asn Thr Leu
            340                 345                 350

Tyr Leu Gln Met Gly Ser Leu Lys Ser Glu Asp Thr Ala Met Tyr Tyr
        355                 360                 365

Cys Thr Arg Ile Gly Tyr Asp Glu Asp Tyr Ala Met Asp His Trp Gly
        370                 375                 380

Gln Gly Thr Ser Val Thr Val Ser Ser Ala Lys Thr Thr Pro Pro Ser
385                 390                 395                 400

Val Tyr Ser Ala Leu Asp Ile Val Leu Thr Gln Ser Pro Leu Thr Leu
                405                 410                 415

Ser Val Asn Ile Gly Gln Pro Ala Ser Ile Ser Cys Lys Ser Ser Gln
            420                 425                 430

Ser Leu Leu Tyr Thr Asn Gly Lys Thr Tyr Phe Asn Trp Leu Leu Gln
        435                 440                 445

Arg Pro Gly Gln Ser Pro Lys Arg Leu Ile Tyr Leu Val Ser Lys Leu
        450                 455                 460

Asp Ser Gly Val Pro Asp Arg Phe Thr Gly Ser Gly Ser Gly Thr Asp
465                 470                 475                 480

Phe Thr Leu Lys Ile Ser Arg Val Glu Ala Glu Asp Leu Gly Val Tyr
                485                 490                 495

Tyr Cys Ala Gln Gly Thr His Phe Pro Trp Thr Phe Gly Gly Gly Thr
            500                 505                 510

Lys Leu Glu Ile Lys Arg Ala Asp Ala Ala Pro Thr Val Ser Ala Ala
        515                 520                 525

Ala Glu Gln Lys Leu Ile Ser Glu Glu Asp Leu Asn Gly Ala Pro Arg
        530                 535                 540

His His His His His His His
545                 550

<210> SEQ ID NO 31
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: prim_transcript

```
<222> LOCATION: 1..24
<223> OTHER INFORMATION: /note="forward primer degKappadir"

<400> SEQUENCE: 31
gayattgtgm tsacmcarwc tmca                                          24

<210> SEQ ID NO 32
<211> LENGTH: 21
<212> TYPE: DNA
<213> ORGANISM: Artificial Sequence
<220> FEATURE:
<223> OTHER INFORMATION: Synthetic construct
<220> FEATURE:
<221> NAME/KEY: prim_transcript
<222> LOCATION: 1..21
<223> OTHER INFORMATION: /note="reverse primer Kapparev"

<400> SEQUENCE: 32
ggatacagtt ggtgcagcat c                                             21

<210> SEQ ID NO 33
<211> LENGTH: 22
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..22
<223> OTHER INFORMATION: /note="forward primer degH1dir"

<400> SEQUENCE: 33
caggttactc tgaaagwgts tg                                            22

<210> SEQ ID NO 34
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..20
<223> OTHER INFORMATION: /note="forward primer degH2dir"

<400> SEQUENCE: 34
gaggtccarc tgcaacartc                                               20

<210> SEQ ID NO 35
<211> LENGTH: 21
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..21
<223> OTHER INFORMATION: /note="forward primer degH3dir"

<400> SEQUENCE: 35
caggtccaaa ctucagcarc c                                             21

<210> SEQ ID NO 36
<211> LENGTH: 20
<212> TYPE: DNA
<213> ORGANISM: Artificial Sequence
<220> FEATURE:
<223> OTHER INFORMATION: synthetic construct
<220> FEATURE:
```

<221> NAME/KEY: prim_transcript
<222> LOCATION: 1..20
<223> OTHER INFORMATION: /note="forward primer degH4dir"

<400> SEQUENCE: 36
gaggtgaass tggtggaatc                                               20

<210> SEQ ID NO 37
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..20
<223> OTHER INFORMATION: /note="forward primer degH5dir"

<400> SEQUENCE: 37
gatgtgaact tggaagtgtc                                               20

<210> SEQ ID NO 38
<211> LENGTH: 36
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..36
<223> OTHER INFORMATION: /note="reverse primer IgG1rev"

<400> SEQUENCE: 38
ggaagatcta tagacagatg ggggtgtcgt tttggc                             36

<210> SEQ ID NO 39
<211> LENGTH: 48
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..48
<223> OTHER INFORMATION: /note="VLFORSFI"

<400> SEQUENCE: 39
cacgcggccc agccggccat ggccgatatt gtgatgacac agactcca                48

<210> SEQ ID NO 40
<211> LENGTH: 66
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..66
<223> OTHER INFORMATION: /note="VLREVSOE"

<400> SEQUENCE: 40
ggagccgccg ccgccagaac caccaccacc agaaccacca ccaccggata cagttggtgc   60
agcatc                                                              66

<210> SEQ ID NO 41
<211> LENGTH: 50
<212> TYPE: DNA
<213> ORGANISM: Artificial Sequence

```
<220> FEATURE:
<223> OTHER INFORMATION: synthetic construct
<220> FEATURE:
<221> NAME/KEY: prim_transcript
<222> LOCATION: 1..50
<223> OTHER INFORMATION: /note="VHFORSOE"

<400> SEQUENCE: 41
ggcggcggcg gctccggtgg tggtggatcc gaggtgaagg tggtggaatc         50

<210> SEQ ID NO 42
<211> LENGTH: 43
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..43
<223> OTHER INFORMATION: /note="VHREVNOT"

<400> SEQUENCE: 42
ataagaatgc ggccgcatag acagatgggg gtgtcgtttt ggc                43

<210> SEQ ID NO 43
<211> LENGTH: 36
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..36
<223> OTHER INFORMATION: /note="VLFORXHO"

<400> SEQUENCE: 43
cacgcctcga gtgatattgt gatgacacag actcca                        36

<210> SEQ ID NO 44
<211> LENGTH: 38
<212> TYPE: DNA
<213> ORGANISM: Artificial Sequence
<220> FEATURE:
<223> OTHER INFORMATION: synthetic construct
<220> FEATURE:
<221> NAME/KEY: prim_transcript
<222> LOCATION: 1..38
<223> OTHER INFORMATION: /note="VHREVAPALI"

<400> SEQUENCE: 44
acgcgtgcac tatagacaga tgggggtgtc gttttggc                      38

<210> SEQ ID NO 45
<211> LENGTH: 390
<212> TYPE: DNA
<213> ORGANISM: Artificial Sequence
<220> FEATURE:
<223> OTHER INFORMATION: synthetic construct
<220> FEATURE:
<221> NAME/KEY: primer_bind
<222> LOCATION: 1..20
<223> OTHER INFORMATION: /note="primer used to isolate the single
      domain"
<220> FEATURE:
<221> NAME/KEY: CDS
<222> LOCATION: 1..390
<223> OTHER INFORMATION: /transl_table=1
<220> FEATURE:
<221> NAME/KEY: misc_feature
<222> LOCATION: 294..294
<223> OTHER INFORMATION: /note="n is a, c, g, or t"
```

```
<220> FEATURE:
<221> NAME/KEY: primer_bind
<222> LOCATION: 363..390
<223> OTHER INFORMATION: /note="primer used to isolate the single
      domain"

<400> SEQUENCE: 45 gag gtg aag ctg gtg gaa tct ggg gga ggc tta gtg cag cct gga gag      48
Glu Val Lys Leu Val Glu Ser Gly Gly Gly Leu Val Gln Pro Gly Glu
1               5                   10                  15 tcc ctg aaa ctc tcc tgt gaa tcc aat gaa tac gaa ttc cct tcc cat      96
Ser Leu Lys Leu Ser Cys Glu Ser Asn Glu Tyr Glu Phe Pro Ser His
            20                  25                  30 gat ttg tct tgg gtc cgc aag act ccg gag aag agg ctg gag ttg gtc     144
Asp Leu Ser Trp Val Arg Lys Thr Pro Glu Lys Arg Leu Glu Leu Val
        35                  40                  45 gca gcc att aat agt gat ggt ggt agc acc tac tat cca gac acc atg     192
Ala Ala Ile Asn Ser Asp Gly Gly Ser Thr Tyr Tyr Pro Asp Thr Met
50                  55                  60 gag aga cga ttc atc atc tcc aga gac aat acc aag aag acc ctg tac     240
Glu Arg Arg Phe Ile Ile Ser Arg Asp Asn Thr Lys Lys Thr Leu Tyr
65                  70                  75                  80 ctg caa atg agc agt ctg agg tct gag gac aca gcc ttg tat tac tgt     288
Leu Gln Met Ser Ser Leu Arg Ser Glu Asp Thr Ala Leu Tyr Tyr Cys
                85                  90                  95 gca agn cgt cta ttc tay gta cga cgg ttc tac ttt gac ttc tgg ggc     336
Ala Xaa Arg Leu Phe Tyr Val Arg Arg Phe Tyr Phe Asp Phe Trp Gly
            100                 105                 110 caa ggc acc act ctc aca gtc tcc tca gcc aaa acg aca ccc cca tct     384
Gln Gly Thr Thr Leu Thr Val Ser Ser Ala Lys Thr Thr Pro Pro Ser
        115                 120                 125 gtc tat                                                             390
Val Tyr
    130

<210> SEQ ID NO 46
<211> LENGTH: 130
<212> TYPE: PRT
<213> ORGANISM: Artificial Sequence
<220> FEATURE:
<223> OTHER INFORMATION: Synthetic Construct
      [CDS]:1..390 from SEQ ID NO 45
<220> FEATURE:
<221> NAME/KEY: DOMAIN
<222> LOCATION: 98..98
<223> OTHER INFORMATION: ARG or SER

<400> SEQUENCE: 46

Glu Val Lys Leu Val Glu Ser Gly Gly Gly Leu Val Gln Pro Gly Glu
1               5                   10                  15

Ser Leu Lys Leu Ser Cys Glu Ser Asn Glu Tyr Glu Phe Pro Ser His
            20                  25                  30

Asp Leu Ser Trp Val Arg Lys Thr Pro Glu Lys Arg Leu Glu Leu Val
        35                  40                  45

Ala Ala Ile Asn Ser Asp Gly Gly Ser Thr Tyr Tyr Pro Asp Thr Met
50                  55                  60

Glu Arg Arg Phe Ile Ile Ser Arg Asp Asn Thr Lys Lys Thr Leu Tyr
65                  70                  75                  80

Leu Gln Met Ser Ser Leu Arg Ser Glu Asp Thr Ala Leu Tyr Tyr Cys
                85                  90                  95

Ala Xaa Arg Leu Phe Tyr Val Arg Arg Phe Tyr Phe Asp Phe Trp Gly
            100                 105                 110
```

```
Gln Gly Thr Thr Leu Thr Val Ser Ser Ala Lys Thr Thr Pro Pro Ser
        115                 120                 125
Val Tyr
    130

<210> SEQ ID NO 47
<211> LENGTH: 348
<212> TYPE: DNA
<213> ORGANISM: Artificial Sequence
<220> FEATURE:
<223> OTHER INFORMATION: synthetic construct
<220> FEATURE:
<221> NAME/KEY: primer_bind
<222> LOCATION: 1..20
<220> FEATURE:
<221> NAME/KEY: CDS
<222> LOCATION: 1..348
<223> OTHER INFORMATION: /transl_table=1
<220> FEATURE:
<221> NAME/KEY: primer_bind
<222> LOCATION: 328..348

<400> SEQUENCE: 47 gat att gtg atc acc cag tct cca tcc tcc ctg tct gcc tct ctg gga     48
Asp Ile Val Ile Thr Gln Ser Pro Ser Ser Leu Ser Ala Ser Leu Gly
1               5                   10                  15 gac aga gtc acc atc agt tgc agg gca agt cag gac att agg aat tat     96
Asp Arg Val Thr Ile Ser Cys Arg Ala Ser Gln Asp Ile Arg Asn Tyr
            20                  25                  30 tta aac tgg tat cag cag aaa cca gat gga act gtt aaa ctc ctc atc    144
Leu Asn Trp Tyr Gln Gln Lys Pro Asp Gly Thr Val Lys Leu Leu Ile
        35                  40                  45 tac tac aca tca aga tta cac tca gga gtc cca tca agg ttc agt ggc    192
Tyr Tyr Thr Ser Arg Leu His Ser Gly Val Pro Ser Arg Phe Ser Gly
    50                  55                  60 agt ggg tct gga aca gat tat tct ctc acc att acc aac ctg gag caa    240
Ser Gly Ser Gly Thr Asp Tyr Ser Leu Thr Ile Thr Asn Leu Glu Gln
65                  70                  75                  80 gaa gat att gcc act tac ttt tgc caa cag ggt aat act ctt cca tgg    288
Glu Asp Ile Ala Thr Tyr Phe Cys Gln Gln Gly Asn Thr Leu Pro Trp
                85                  90                  95 acg ttc ggt gga ggc acc aag ctg gga atc aag cgg gct gat gct gca    336
Thr Phe Gly Gly Gly Thr Lys Leu Gly Ile Lys Arg Ala Asp Ala Ala
            100                 105                 110 cca act gta tcc                                                    348
Pro Thr Val Ser
        115

<210> SEQ ID NO 48
<211> LENGTH: 116
<212> TYPE: PRT
<213> ORGANISM: Artificial Sequence
<220> FEATURE:
<223> OTHER INFORMATION: Synthetic Construct
       [CDS]:1..348 from SEQ ID NO 47

<400> SEQUENCE: 48

Asp Ile Val Ile Thr Gln Ser Pro Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45
```

-continued

```
Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Thr Asn Leu Glu Gln
65              70                  75                      80

Glu Asp Ile Ala Thr Tyr Phe Cys Gln Gln Gly Asn Thr Leu Pro Trp
                85              90                  95

Thr Phe Gly Gly Gly Thr Lys Leu Gly Ile Lys Arg Ala Asp Ala Ala
            100             105                 110

Pro Thr Val Ser
            115
```

MONO AND BISPECIFIC ANTIBODY BINDING TO HERG1 AND HERG1/INTEGRIN BETA 1

This application is a national stage application under 35 U.S.C. § 371 of PCT Application No. PCT/EP2018/067641, filed Jun. 29, 2018, which claims the priority benefit of Italian Patent Application No. 102017000083637, filed Jul. 21, 2017.

FIELD OF THE INVENTION

The present invention refers to the field of antibodies and their application for diagnostic and therapeutic purposes in oncology and other fields of medical sciences. In particular it relates to anti-hERG1 molecules and their engineered derivatives comprising bispecific antibodies targeting both hERG1 and β1 integrin.

STATE OF THE ART

Over the past two decades, the antibodies' production technology has been significantly improved through antibody engineering; the advent of new technologies in the field of molecular engineering, led to the production of a wide variety of genetically engineered antibodies, such as fragments of type Fab, Fv form of simple chain of scFv, diabodies, triabodies, bispecifics, minibodies, nanobodies, phage antibodies. In fact there is a range of applications, in which the Fc-mediated effects are not required and even undesirable, because of their associated toxic effects and their capacity to evoke an immune response able to neutralise the antibody efficacy, when its Fc derived from a non human source.

Among the engineered antibody fragments, the Single Chain Variable Fragment (scFv) is the most popular and one of the smallest recombinant format with an antigen-binding activity function and with the property to be easily manageable for immunological application.

A scFv consists of variable regions of heavy (VH) and light (VL) chains, which are joined together by a flexible peptide linker, without compromising the fidelity of the VH-VL paring and antigen-binding sites. The choice of a linker can affect the solubility, expression and correct folding of the scFv. Peptide linkers can vary from 10 to 25 amino acids in length and are typically composed of hydrophilic amino acids such as glycine (G) and serine (S). Hydrophilic sequences prevent intercalation of the peptide within or between the variable domains throughout the protein folding.

The most common linker used is the (Gly4Ser)3 motif, due to its flexibility, neutral charge and solubility. The use of scFv in diagnostics and therapy provides several advantages over whole antibodies, especially in solid tumours' therapy; in fact, the speed of penetration by a fragment versus an intact molecule is the most remarkable advantage. In 1988, it was established that an intact molecule of IgG took fifty-four hours to penetrate 1 mm into a solid tumour, while a Fab fragment managed the same distance in sixteen hours. Moreover, the scFv, as well as all the other antibody fragments format, can be mold into multivalent and multispecific reagents or easily linked to therapeutic tools as radionuclides, toxins or nanoparticles and engineered to improve their diagnostic and therapeutic efficacy.

These engineered molecules are easy to produce in bacterial or yeast systems, furthermore extravasate more efficiently and have a higher tissue penetration ability than full length Ig; the only limit of these molecules is the short half-life due to their small size. Many strategies has been developed to improve pharmacokinetic such as multimerization of scFv (shortening their linker sequence) to form triabodies (of about 90 kDa) and tetrabodies (of about 120 kDa), or conjugation of antibodies to big molecules such as polyethylene glycol (PEG) (Natarajan et al. 2005) or human serum albumin (HSA).

Bispecific antibodies (bsAbs) have recently raised a lot of attention as potential cancer therapeutic agents because they offer several advantages:
  bsAbs can redirect specific immune cells towards tumour cells, thereby enhancing tumor killing;
  bsAbs can simultaneously block two different targets in different pathways that carry out unique or overlapping functions in pathogenesis;
  bsAbs can potentially increase binding specificity by interacting with two different cell-surface antigens instead of one.

The development of bispecific antibodies (bsAbs) has experienced many difficulties, mainly due to the manufacturing problems, poor yields, instability and immunogenicity (Spiess C. et al, 2015).

Concerning the methodology for bsAbs production, they are primarily produced by three methods, which include:
  quadroma technology, based on the somatic fusion of two different hybridomas cell lines;
  chemical conjugation, through the use of chemical cross-linkers;
  genetic approaches utilizing recombinant DNA technology.

Bispecific antibodies can be roughly divided into two main subgroups: immunoglobulin G (IgG)-like molecules and non-IgG-like molecules and so far there are over 30 bsAbs in clinical development with two, Catumaxomab and Blinatumomab, already approved for the market.

Non-IgG-like include mainly scFv-based bsAbs and nanobodies. It is known that scFvs can become dimers, trimers, or tetramer depending on linker length, antibody sequence and other factors (Le Gall F. et al., 1999). Such format is favored and has many possible clinical applications. Among scFv-based bsAbs formats there are:
  Tandem scFvs, which consist of two scFvs connected by a flexible peptide linker, such as glycine-serine repeat motifs in a tandem orientation. The famous bispecific T cell engager (BiTE) technology is based on this format (Chames P. et al., 2009).
  Diabody format, in which the variable domains of two different antibodies are connected by two linkers. These have the function to increase the stability of the diabody.
  Single-chain diabodies (scDbs), the diabody format can be converted into a single-chain diabody by adding an additional connection linker between the chains
  Tandem diabodies (TandAbs) are formed by two pairs of VL and VH domains, connected in a single polypeptide chain, forming a tetravalent TandAb.
  Dual-affinity retargeting molecules (DARTs) DARTs are created by the association of the VH of a first variable region linked to the VL on a second chain, and the VH of the second variable region linked to the VL on the first chain in a VLA–VHB+VLB–VHA configuration. Due to their small size, DARTs are prone to elimination (Moore P. A. et al., 2011).

Diabodies and scDbs are also the most effective way to generate bispecific antibody fragments, able to bind two different antigens and thus useful to crosslink cells (e.g.

retargeting immune system effector cells); to recruit effector molecules (like toxins, drugs, cytokines, radioisotopes, or complement system), to retarget carrier system (such as viral vectors for gene therapy) (Kontermann 2005); to target and inhibit macromolecular complexes involved in tumour progression.

Antibody engineering provided also methods to increase avidity (e.g antibody fragments multimerisation); affinity (e.g. mutation in the variable regions of whole Ig or antibody fragments); and enhance effector functions (e.g. mutation in the constant regions of whole Ig or conjugation of antibody fragments with recombinant Fc, toxin, drugs, cytokines, death ligands, radioisotopes, nanoparticles or complement system molecules).

Over the past three decades, the human ether-à-go-go-related gene 1 (hERG1) potassium channel has become a target in oncology as well as in other human diseases. However, its exploitation for therapeutic purposes has been hindered by the fact that most drugs that cause hERG1 blockade as their primary or side effect, can cause cardiotoxicity (lengthening of the electrocardiographic QT interval and onset of ventricular arrhythmias). In search of biophysical and biomolecular features which distinguish hERG1 expressed in the heart from hERG1 expressed in cancer cells and other disease characteristic cells, it was found that hERG1 complexes with other plasma membrane proteins, in particular with the beta1 subunit of integrin receptors, on the plasma membrane of cancer cells. Such complex does not occur in cardiac myocytes (Becchetti A. et al., Sci. Signaling, 10(473). pii: eaaf3236. doi: 10.1126/scisignal.aaf3236. PMID: 28377405, 2017). Hence, the hERG1/beta1 integrin complex configures as an oncogenic unit, peculiar of transformed cells, a fact that differentiate hERG1 in tumor from the channel expressed in the heart. This finding implies that any molecule (a small molecule drug or otherwise a protein) targeting the hERG1/beta1 integrin complex can be used for diagnostic and therapeutic purposes, being devoid of cardiotoxicity. At the moment molecules able to target hERG1/beta1 integrin complex are not known.

In the Italian Patent IT1367861 is described a hybridoma cell line clone, named A7, able to secrete an anti-hERG1 monoclonal antibody (mAb) specific against the S5-pore extracellular portion of hERG1.

WO2016020483 (A1) describes the detailed structure of an intact murine monoclonal anti-hERG1 molecule and a corresponding anti-hERG1 scFv antibody production, obtained after the isolation of the mAb anti-hERG1 VH and VL. Such scFv has the same specificity of the correspondent whole antibody, and thus it is able to recognize the same anti-hERG1 protein, aberrantly expressed in tumours and other diseases. Nucleotide sequences SEQ ID NO:1 and SEQ ID NO:3 encoding respectively VH (SEQ ID NO:2) and VL (SEQ ID NO:4) were disclosed together with nucleotide sequence SEQ ID NO:5 encoding for a scFV having SEQ ID NO:6.

There are known in the art, for research purposes, anti-beta1 integrin mAb, for example are known among others TS2/16 (Arroyo et al. J. Cell Biol. 1992, 117(3), 659-670) and BV7 (Martin-Padura et al. J. Biol. Chem. 1994, 269(8), 6124-6132).

Aim of the present invention is to provide a bispecific antibody which targets simultaneously both the hERG1 and the beta1 integrin proteins which are complexed on the plasma membrane of cancer cells. Further aim of the present invention is to provide an improved, or at least alternative, antibody against hERG1.

SUMMARY OF THE INVENTION

Subject-matter of the present invention is a bispecfic antibody (bsAb) comprising the Heavy chain Variable (VH) domain and Light chain Variable (VL) domain of an anti-hERG1 Ab which binds the extracellular domain S5-P of hERG1 and the Heavy chain Variable (VH) domain and Light chain Variable (VL) domain of a anti-β1 integrin Ab which binds the extracellular domain of β1 integrin.

Surprisingly it was found that a bsAb according to the invention was able to bind selectively the complex hERG1+β1-integrin which is present only in tumor cells. In particular a bsAb according to the invention showed the capacity in vitro of inhibiting cell growth and migratory, pro-metastatic, activity on a panel of neoplastic cell lines.

For an aspect the present invention relates also to an anti-hERG1 molecule comprising a Heavy chain Variable (VH) domain having at least 85% identity with SEQ ID NO:8 wherein residue at position 95 is Cys, and a Light chain Variable (VL) domain having at least 85% identity with SEQ ID NO:4, said molecule having specificity against hERG1 S5-pore extracellular portion.

Surprisingly it was found that an anti-hERG1 molecule (anti-hERG1-Cys) according to the invention and having a Cys in position 95 of the VH domain (SEQ ID No: 8), showed a better affinity toward the immobilized antigen compared to a molecule, as known in the state of the art, having a Phe in position 95 of the VH domain (SEQ ID No: 2). In particular an scFv molecule according to the invention showed the capacity in vitro of inhibiting cell growth on a panel of neoplastic cell lines.

DETAILED DESCRIPTION OF THE INVENTION

Preferably the bsAb of the invention are those wherein the Heavy chain Variable (VH) domain of anti-hERG1 Ab has 85% identity with SEQ ID No: 8 or SEQ ID No: 2; and the Light chain Variable (VL) domain of anti-hERG1 Ab has 85% identity with SEQ ID No: 4; and the Heavy chain Variable (VH) domain and a Light chain Variable (VL) domain of a anti-β1 integrin Ab have at least 85% identity with VH and VL of TS2/16 (SEQ ID N: 26 and 24) or BV7 (SEQ ID N: 46 and 48).

Preferably the bsAb of the invention is a non-IgG-like bsAb, preferably a scFv-based bsAb. According to the invention the scFV-based bsAb has a format selected in the group consisting of Tandem scFvs, Diabody format, Single-chain diabodies, Tandem diabodies (TandAbs) and Dual-affinity retargeting molecules (DARTs), preferably scDb.

Preferably the VH domain of anti-β1 integrin Ab has an 90%, 95%, 99% or 100% identity with SEQ ID NO:26 or SEQ ID NO:46, more preferably SEQ ID NO:26.

Preferably the VL domain of anti-β1 integrin Ab has an 90%, 95%, 99% or 100% identity with SEQ ID NO:24 or SEQ ID NO:48, more preferably SEQ ID NO:24. Preferably the VH domain of anti-hERG1 Ab, still retaining the amino acid Cys at position 95, has an 90%, 95%, 99% or 100% identity with SEQ ID NO:8.

Preferably the VH domain of anti-hERG1 Ab has an 90%, 95%, 99% or 100% identity with SEQ ID NO:2.

Preferably the VL domain of anti-hERG1 Ab has an 90%, 95%, 99% or 100% identity with SEQ ID NO:4.

The VH domain of anti-hERG1-Cys Ab according to the present invention is preferably encoded by a sequence of nucleotides having at least 70%, 80%, 90%, 95%, 99% or 100% homology with SEQ ID No: 7 wherein the triplet from residue 283 to 285 can be TGT or TGC.

The VH domain of anti-hERG1 Ab according to the present invention is preferably encoded by a sequence of nucleotides having at least 70%, 80%, 90%, 95%, 99% or 100% homology with SEQ ID No: 1.

The VL domain of anti-hERG1 Ab according to the present invention is preferably encoded by a sequence of nucleotides having at least 70%, 80%, 90%, 95%, 99% or 100% homology with SEQ ID No: 3.

Molecule according to the invention can be a fully humanized recombinant Ab.

Molecule according to the invention can be a scFv or any other engineered antibody such as Fab, Fv form of simple chain of scFv, diabodies, triabodies, bispecifics, minibodies, phage antibodies; preferred are scFv and diabodies (scDb).

Preferred linkers are the (Gly4Ser)3 motifs.

Particularly preferred is an anti-hERG1-Cys scFv wherein VH and VL are linked by a peptide linker; more preferred is an anti-hERG1-Cys scFv having SEQ ID No: 10.

Particularly preferred is a bsAb which is a single chain diabody (scDb) comprising an anti-hERG1-Cys scFv and an anti-β1-integrin scFv, thus acting selectively against the complex hERG1+β1-integrin which is present only in tumor cells.

For a preferred aspect, therefore, the present invention relates to a bsAb single chain diabody (scDb) comprising a first Heavy chain Variable (VH) domain having at least 85% identity with SEQ ID NO:8 wherein residue at position 95 is Cys, and a first VL domain having at least 85% identity with SEQ ID NO:4, and a second VH domain having at least 85% identity with SEQ ID NO:26 or SEQ ID N: 46, and a second VL domain having at least 85% identity with SEQ ID NO:24 or SEQ ID N: 48, said bispecific Ab having specificity against hERG1 S5-pore extracellular portion and against β1-integrin.

A bsAb or an anti-hERG1 molecule according to the invention is useful as diagnostic or therapeutic tool.

A diagnostic tool according to the invention is for in vitro hERG1 detection (e.g. in surgical samples or biopsies) comprise the anti-hERG1-Cys scFv and/or, the bispecific Ab (preferably as scDb) according to the invention, either unlabeled or linked to a fluorophore, preferably fluorophoreAlexa 488.

Subject-matter of the present invention is therefore also an In Vitro Diagnostics (IVD) kit of parts for the simultaneous, separate or sequential use, said IVD kit comprising:
   a container containing the anti-hERG1-Cys scFv as above described; and/or
   a container containing the bispecific Ab as above described Preferably the IVD kit further comprises a container containing an Intact Monoclonal Antibody as described in WO2016020483, as a reference control.

The IVD kit can be used either on fixed tissue samples for ImmunoHisto Chemistry techniques (with results being available in 2-3 weeks) or on FRESH BIOPTIC TISSUE (obtained e.g. by Endoscopy or surgery), to be used with Immunofluorescence techniques, with results being available in 1 day.

The anti-hERG1-Cys scFv as above describes labelled with a fluorophore (for example and preferably Alex 750) or radionuclide (for example and preferably Tc$^{99}$) is a molecule for use in in vivo (humans) early diagnosis of hERG1 positive cancers are represented by the anti-hERG1-Cys scFv. The anti-hERG1-Cys sc-FV antibody according to the invention has a specific molecular structure allowing rapid penetration into the cancer tissue, rapid binding to the hERG1 biomarker and rapid elimination, rendering it, when linked to a radionuclide, an ideal molecule for obtaining early in vivo (humans) diagnosis of hERG1 positive cancers. The use in one single administration and the fast half-life, 3.5 hours of the molecule with no systemic toxicity when injected intravenously at 8 mg/kg, and no alterations at the ECG (see FIG. 19) allow to have no interaction with cardiac cells. Finally, the anti-hERG1-Cys scFv turned out to have a very good tumour/tissue ratio, when injected intravenously at 1 mg/kg in mice carrying a xenogafted pancreatic cancer in the pancreas.

Therapeutic tools: The bispecific antibody molecule according to the invention, specifically designed to inhibit cancer hERG1/beta1 integrin molecular complex for therapeutic purposes, is the single chain bispecific antibody (single chain Diabody, scDb) that is able to bind selectively hERG1 when expressed with the beta1 integrin on Cancer cells, with no interaction with the heart. The scDb according to the invention represents an ideal molecule to be used for repeated (chronic) administration in patients with hERG1 positive Cancers, with no cardiac safety concern, with a therapeutic potential both at an early as well as at an advanced/metastatic stage, both as Single Agent as well as Combination Therapy agent, to be added to Chemotherapy, Irradiation, Target Therapy and Immuno-Oncology Therapy. The rationale for the Combination Therapy is that the pathways constitutionally activated in cancer cells by overexpression of the hERG1/beta1 integrin molecular complex are complementary and integrative of the pathways currently targeted by the available drugs. Furthermore, hERG1/beta1 integrin cancer pathway can represent a mechanism of tumour escape in respect to current available Therapies. The anti-hERG1/beta1 integrin scDb turned out to have a half life of roughly 12 hours, with no systemic toxicity when injected intravenously at 8 mg/kg, and no alterations at the ECG (see FIG. 20). Finally, the anti-hERG1/beta1 integrin scDb turned out to have a very good therapeutic efficacy when injected at 1 mg/Kg, twice a week for six times in mice carrying xenografted pancreatic cancers in the pancreas.

Pathologies which can be diagnosed or treated using a bsAb or a molecule according to the invention are all those pathologies characterized by an over expression or misexpression of hERG1 protein. Among said pathologies can be listed tumours, neurological diseases, endocrine diseases and neuro-endocrine diseases.

A bsAb or a molecule according to the invention, in particular an anti-hERG1-Cys scFV or scDb, can also be used as a pharmaceutical delivery vector: so for example it can be covalently or not bonded to radionuclide, enzyme, drugs or toxin.

Further subject-matter of the present invention are therefore also a pharmaceutical composition comprising the bsAb or the molecule according to the invention and at least another pharmaceutically acceptable ingredient.

Further subject-matter of the present invention is also a sequence of nucleotides encoding the bispecific Ab or an anti-hERG1 molecule according to the invention.

Suitable grades of homology (e.g. at least 85%) with the encoding sequences which allows to obtain a molecule according to the invention are intended to be included.

A molecule according to the invention can be preferably prepared by employing nucleotide sequences SEQ ID NO:7 and SEQ ID NO:2 encoding respectively VH (SEQ ID NO:8) and VL (SEQ ID NO:4).

Particularly preferred according to the invention is a method for preparing an anti-hERG1-Cys scFv according to the invention, said method comprising the use of nucleotide sequence SEQ ID NO:9 encoding for an anti-hERG1-Cys scFV having SEQ ID NO:10.

A scDb-hERG1-β1 according to the invention is preferably prepared by employing nucleotide sequences SEQ ID NO:7, SEQ ID NO:2, SEQ ID NO:23 or SEQ ID N: 47 and SEQ ID NO:25 or SEQ ID N: 45 encoding respectively anti-hERG1-Cys VH (SEQ ID NO:8), anti-hERG1-Cys VL (SEQ ID NO:4), anti β1-integrin VL (SEQ ID No: 24 or SEQ ID N: 48) and anti β1-integrin VH (SEQ ID No: 26 or SEQ ID N: 46).

Preferably the domains are assembled in the following order: anti-hERG1-Cys VH (SEQ ID NO:8), anti β1-integrin VL (SEQ ID No: 24 or SEQ ID N:48), anti β1-integrin VH (SEQ ID No: 26 or SEQ ID N:46) and anti-hERG1-Cys VL (SEQ ID NO:4).

Particularly preferred, according to the invention, is a method for preparing a scDb-hERG1-β1 according to the invention, said method comprising the use of nucleotide sequence SEQ ID NO:29 encoding for an anti-hERG1-Cys scFV having SEQ ID NO:30.

The method according to the invention implies recombinant techniques.

Therefore subject-matter of the present invention are also an expression vector or a plasmid comprising the sequence of nucleotides encoding the bispecific Ab or the molecule according to the invention, preferably comprising SEQ ID NO:7 and SEQ ID NO:2 as well as genetically modified microorganisms or a cell comprising an expression vector according to the invention. The above expression vector or a plasmid can also comprise SEQ ID NO:23 or 47 and SEQ ID NO:25 or 45.

The present invention could be better understood in light of the experimental section below.

BRIEF DESCRIPTION OF THE FIGURES

FIG. 3—(A) SDS-PAGE of purified scFv-hERG1-G3 and scFv-hERG1-D8Cys elution fractions; (B) gel filtration chromatography of both purified antibodies, using Superdex 75 HR 10/30. (C) scFv-hERG1-D8Cys antibody stability test. SDS-Pages followed by Coomassie Brilliant blue staining are reported in the picture at different time points (0, 6, 12 and 18 months after protein purification).

FIG. 4—(A) Immunofluorescence performed on fixed and live HEK293Mock and HEK293-hERG1 cells, using both unlabeled (I. IF) and labelled scFv-hERG1-G3 antibody (D.IF). Representative images taken at 20× magnification, nuclei staining is represented by blue fluorescence, membranous staining is represented by the green staining (Alexa 488).

(B) Immunofluorescence performed on fixed and live HEK293-Mock and HEK293-hERG1 cells, using both unlabeled (I. IF) and labelled scFv-hERG1-D8-Cys antibody (D.IF). Representative images taken at 20× magnification, nuclei staining is represented by blue fluorescence, membranous staining is represented by the green staining (Alexa 488).

(C) Graphs showing the IF intensity (A.U.) calculated using Image J Software (ImageJ 1.38, U.S. National Institutes of Health). For each image, the mean of the fluorescence intensity of three different areas was calculated after the subctraction of the blue channels values (which refers to nuclei staining).

In all experiments results on HEK 293-hERG1 were significantly higher compared to those obtained on HEK 293-Mock. Statistical analysis was performed assessing data normality and homoskedasticity assumptions applying Shapiro-Wilk test, while variance was analyzed through Anova. Pairwaise significance was estimated applying t-test or Bonferroni test (* $p<0.05$).

Figure 5:
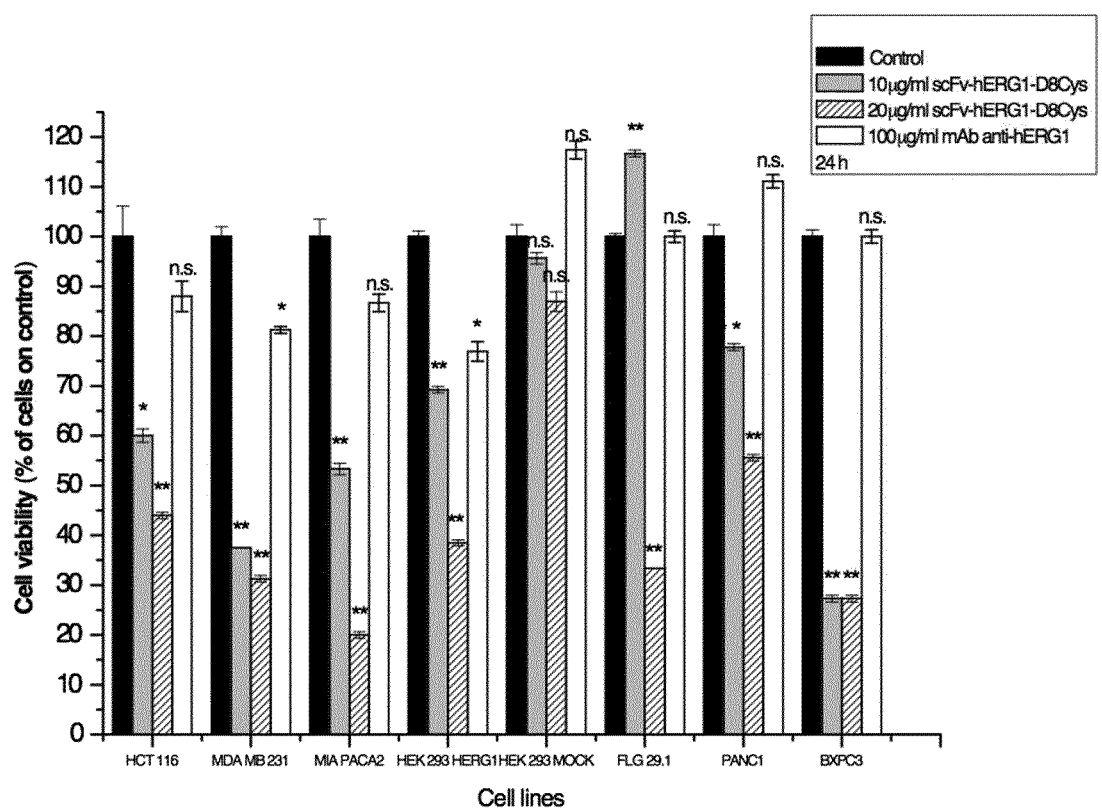

FIG. 5—Trypan blue viability assay performed on HCT-116, MDA MB-231, MIA PACA2, HEK 293 HERG1, HEK-MOCK, FLG 29.1, PANC-1, BxPC-3, using anti-hERG1 monoclonal antibody (100 μg/ml) and scFv-hERG1-D8Cys (10; 20 μg/ml).

All experiments were performed in triplicate.

Figure 6:
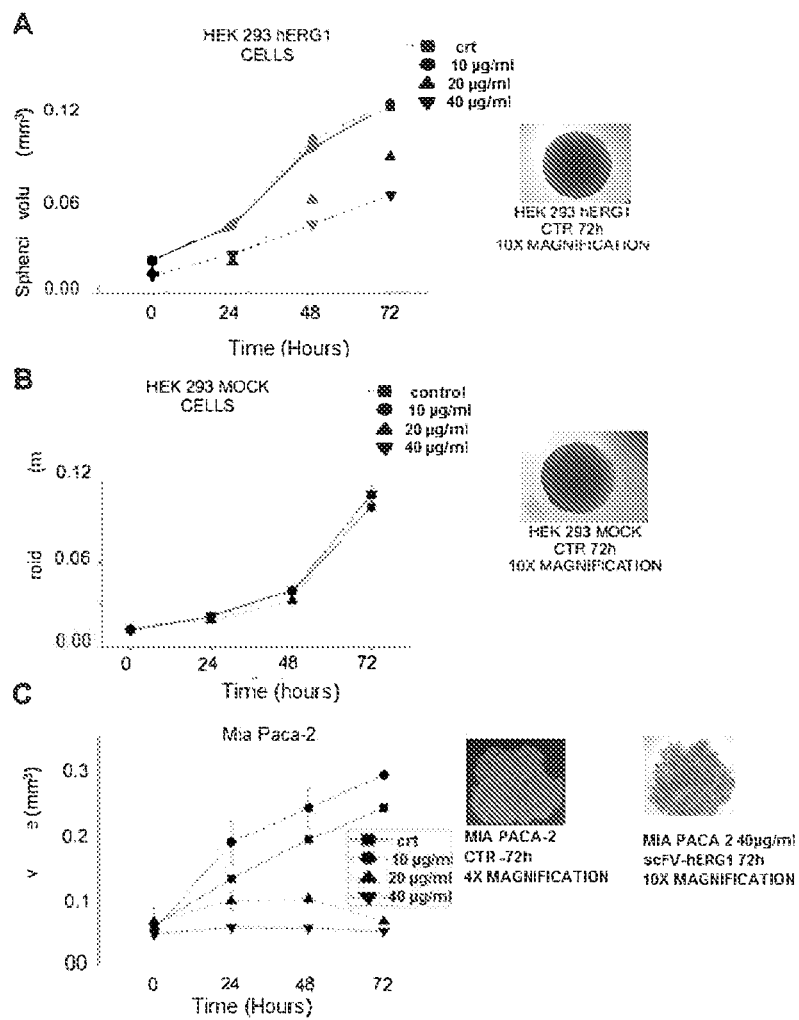
Figure 6D:
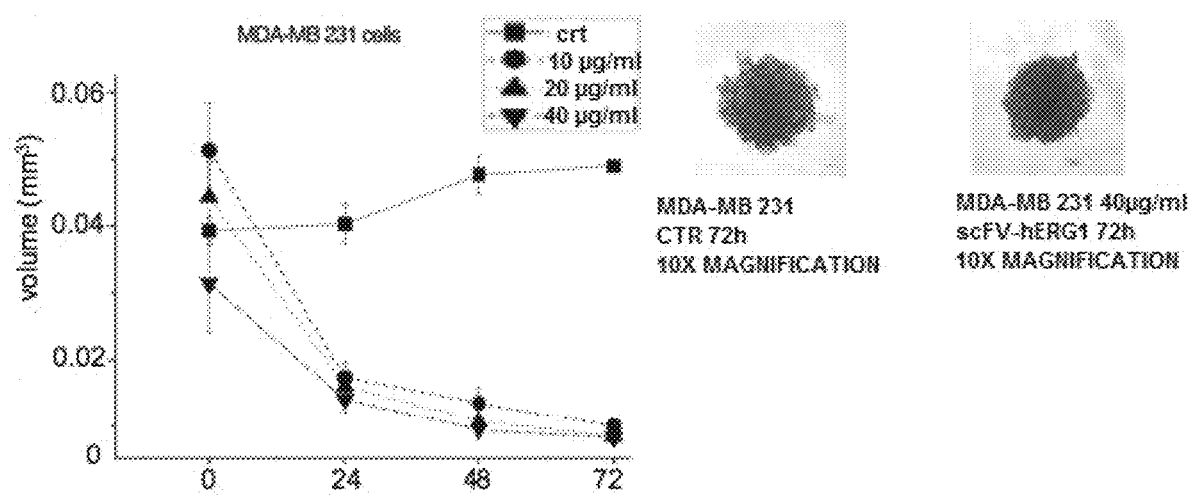

FIG. 6—Panel A: HEK 293 HERG1 spheroids 10, 20 and 40 μg/ml scFv-hERG1-D8Cys were tested. Volume of the spheroids treated with 20 μg/ml and 40 μg/ml scFv-hERG1-D8Cys is smaller (see dotted and dash-dot lines, respectively) compared to the control (solid line) at each timepoint. Panel B, instead, shows the growth curve of the HEK-MOCK (not expressing hERG1) spheroids, in which no difference was found for treated spheroids at all the three concentrations scFv-hERG1-D8Cys tested, compared to the control. Panel A and B also show a representative brightfield image of the control HEK293-hERG1 and HEK-MOCK spheroids, respectively, as they appeared after 72 h culture. Panel C. Pancreatic ductal adenocarcinoma spheroids. Panel C shows the effect obtained on pancreatic ductal adenocarcinoma Mia Paca 2 cells. A decrease in the volume of spheroids was observed both for cells treated with 20 μg/ml and 40 μg/ml scFv-hERG1-D8Cys, with a more pronounced effect obtained at the highest concentration tested (dash-dot line) compared to the controls, at each timepoint. Also. pictures taken after 72 h, reported on the right side of the panel, show a substantial decrease in the spheroid volume for cells treated with 40 μg/ml scFv-hERG1-D8Cys antibody (see right image), compared to the control (see left image). Panel D—Breast cancer cells, MDA-MB 231 spheroids: a marked effect of volume reduction is observed for all the three concentrations of scFv-hERG1-D8Cys tested (10, 20, 40 μg/ml) compared to the control. Volume reduction can be inferred also from the pictures of MDA-MB 231 spheroids reported on the right side of the figure.

Figure 7:
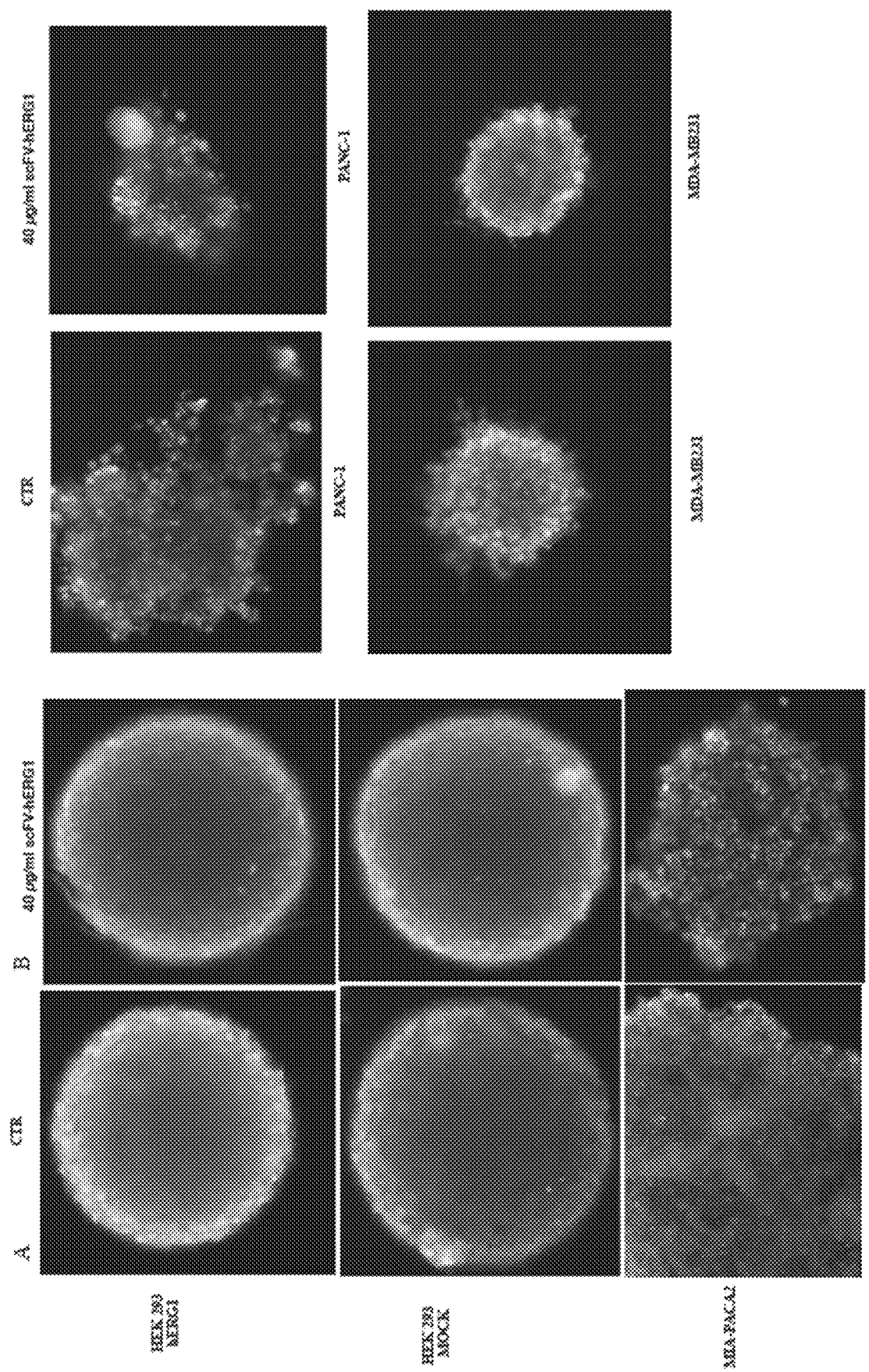

FIG. 7—Calcein AM cell viability assay performed on spheroids after 72 h. Green staining represent live cells, while red staining represent dead cells. Image on the left (panel A) are pictures of the control for each cell line, while on the right side (panel B) there are pictures of spheroids treated with 40 µg/ml scFv-hERG1-D8Cys. From the image it is possible to note the volume reduction for spheroids treated with the antibody, especially for Mia Paca 2, MDA MB-231 and PANC-1 spheroids and, moreover, an increased number of dead cells, especially for MDA MB-231 and PANC-1 spheroids treated with scFv-hERG1-D8Cys.

FIG. 8A—anti b1-integrin (TS2/16) VL and VH domains nucleotide sequence (SEQ ID No: 23 and 25) have been obtained by Automated DNA sequencing service (PRIMM). Underlined in italics is shown VL sequence, in italics VH sequence.

FIG. 8B—anti b1-integrin (BV7) VL and VH domains nucleotide sequence (SEQ ID No: 45 and 47). In bold primers used to isolate the single domains are reported, while highlighted in grey is reported the region of VH sequence which is unknown but it resulted necessary for the correct frame.

Figure 9:
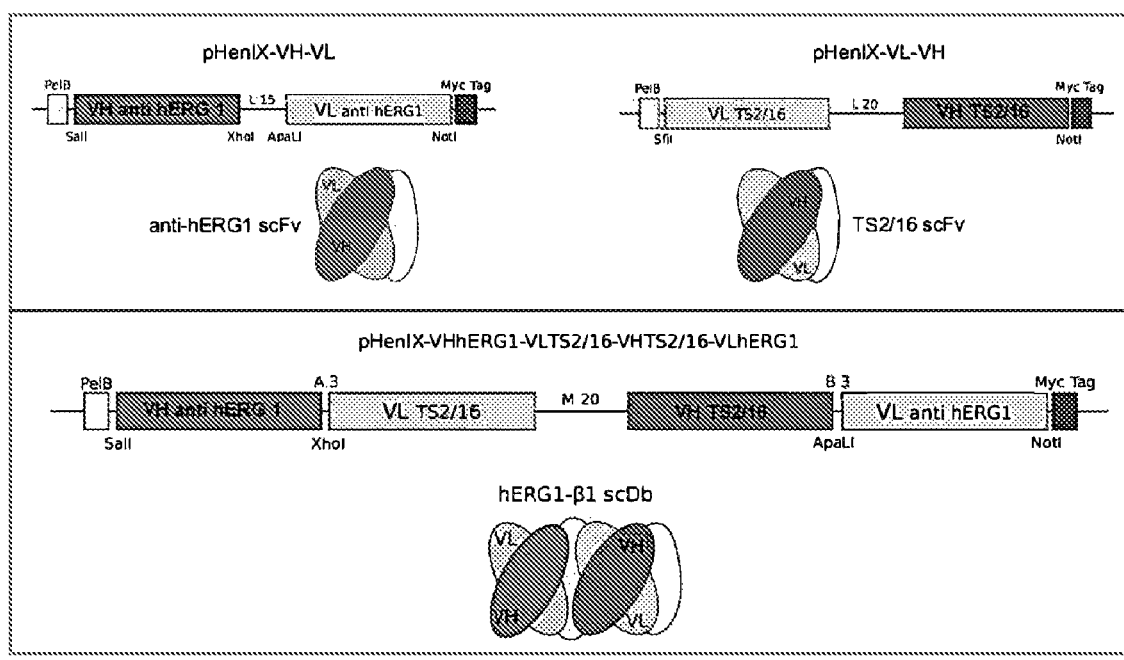

FIG. 9—Upper panels: schematic structure of the two single-chain antibody, anti-hERG1 and anti-TS2/16. Lower panels: schematic structure of the scDb-hERG1-β1.

Figure 10:
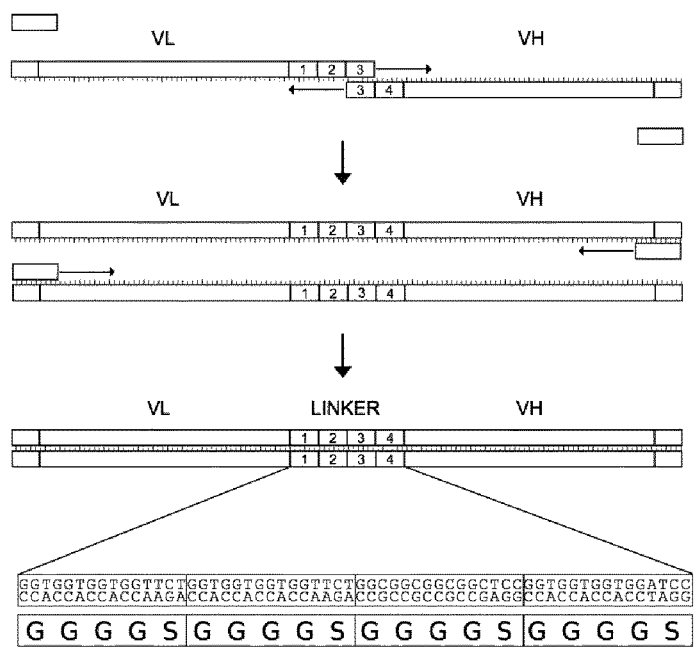

FIG. 10—Scheme representing SOE-PCR method for anti b1-integrin scFv assembly in the order VL-linker-VH.

Figure 11:
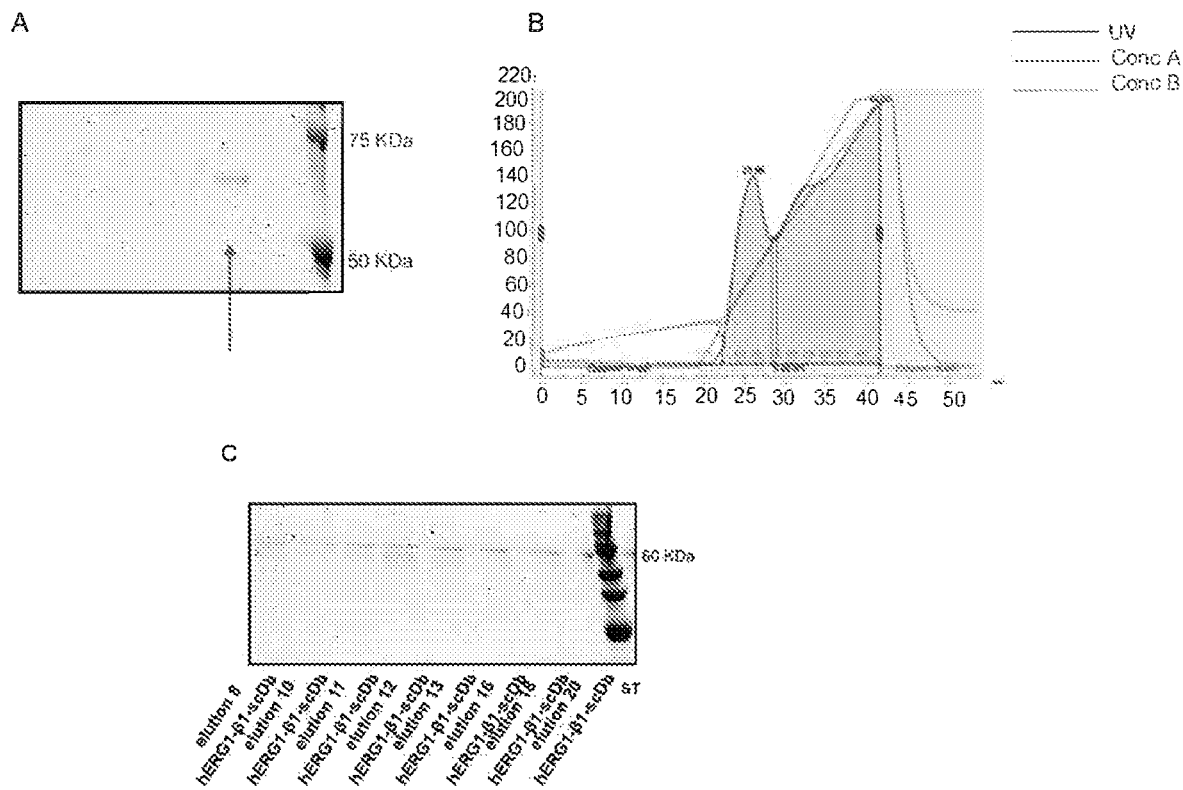

FIG. 11—Panel A shows Coomassie staining of purified supernatants deriving from small scale induction of six clones grown after transformation with anti-hERG1-Phe-β1-scDb construct. One band is detectable corresponding to clone G5 with a molecular weight around 60 KDa, consistent with the one expected.

Panel B shows chromatogram generated after purification of supernatant deriving from high-scale expression of G5 clone: one single peak is visible and elutions underlying the blue area have been analyzed and Coomassie staining is reported in panel C, showing bands with proper molecular weight in all the elutions tested.

Figure 12:
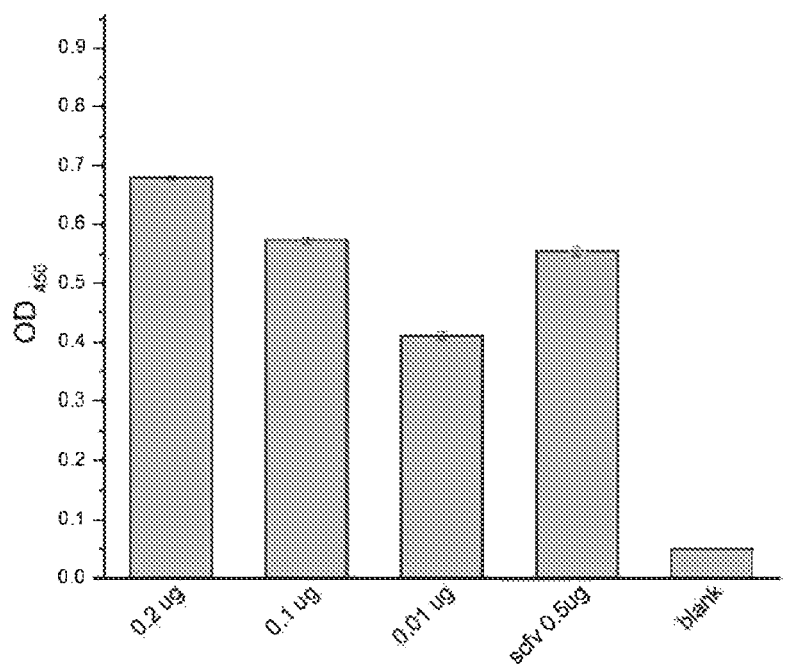

FIG. 12—Panel A. Results from cell-ELISA performed on HEK 293 HERG1 cells, using different amounts of anti-hERG1-Phe-β1-scDb bispecific antibody.

Figure 13:
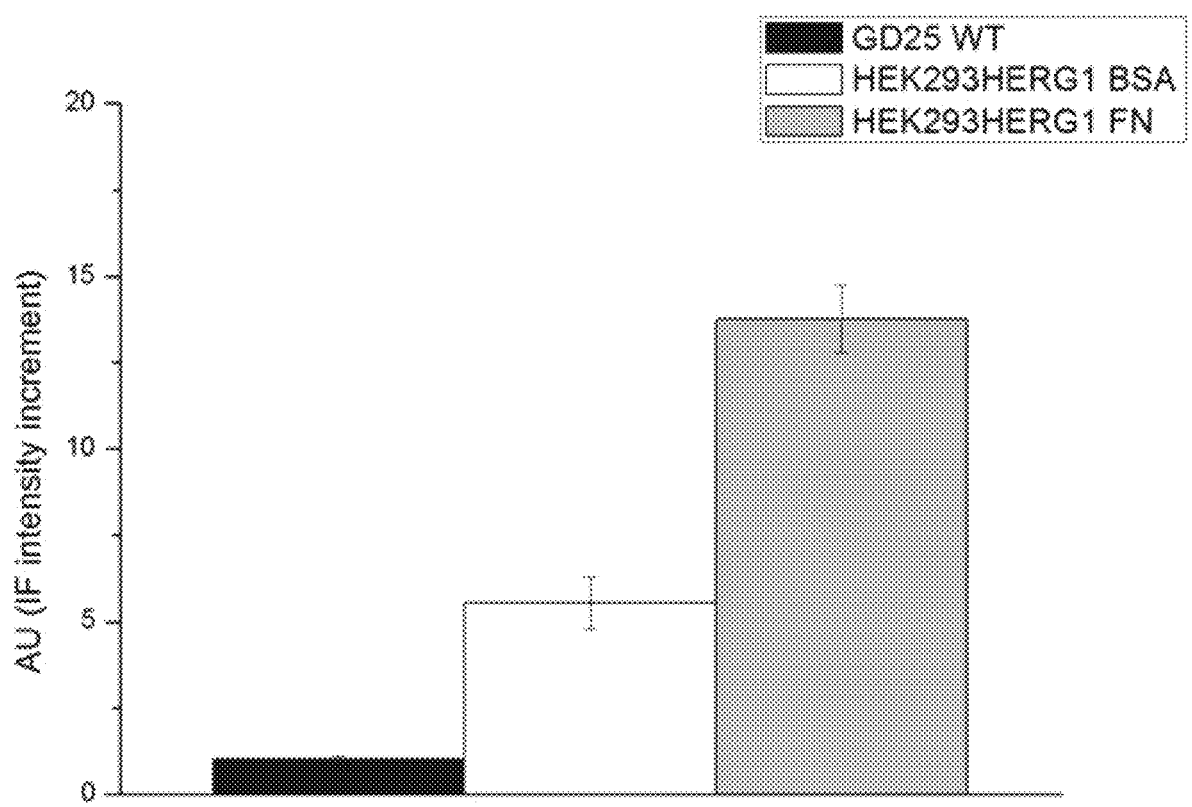

FIG. 13—Indirect IF performed on cells seeded on different substrates, BSA and Fibronectin (FB). IF shows a stronger signal for cells HEK 293 HERG1 coated on FB compared to that obtained for cells coated on BSA.

Figure 14:
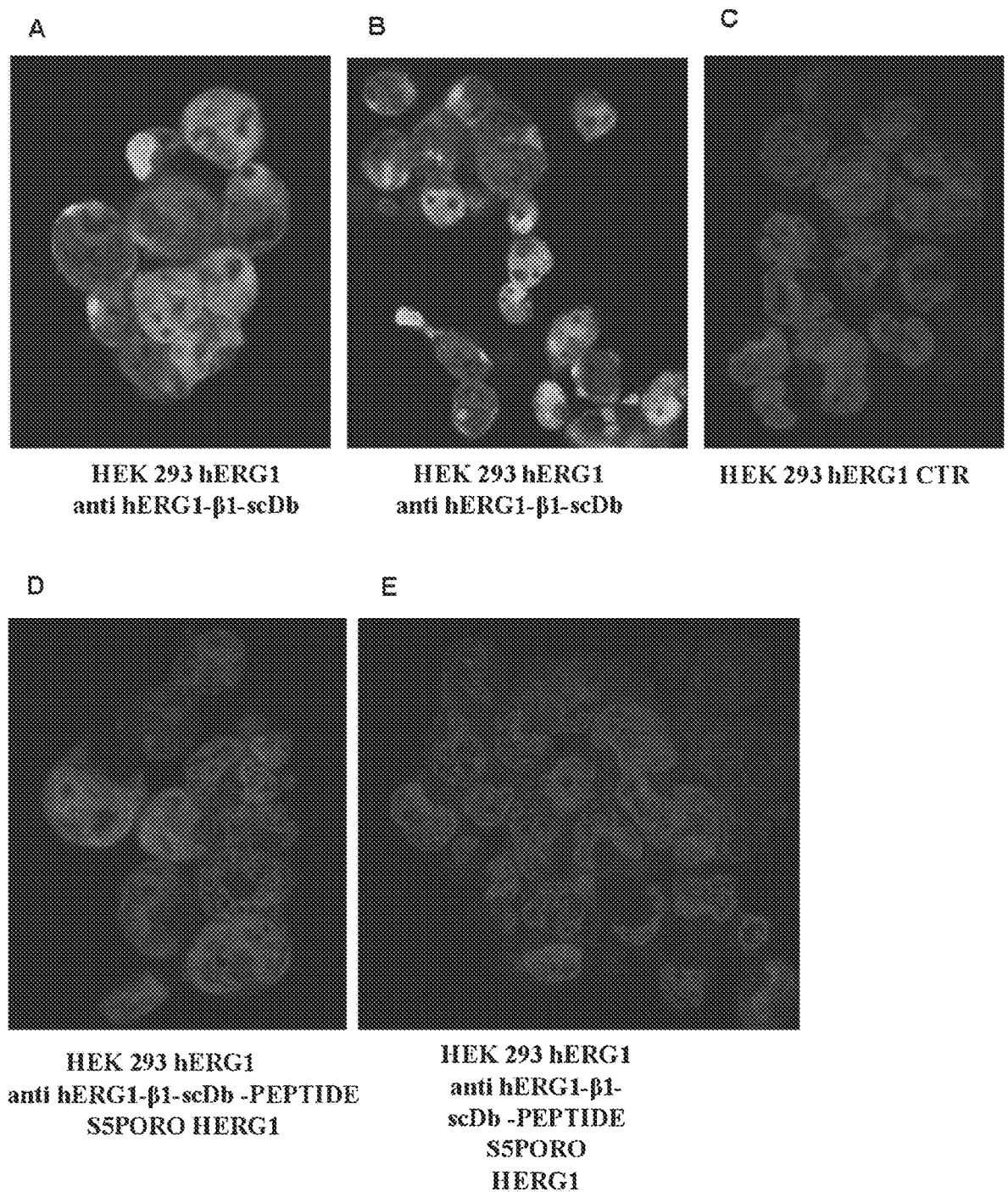
Figure 14:
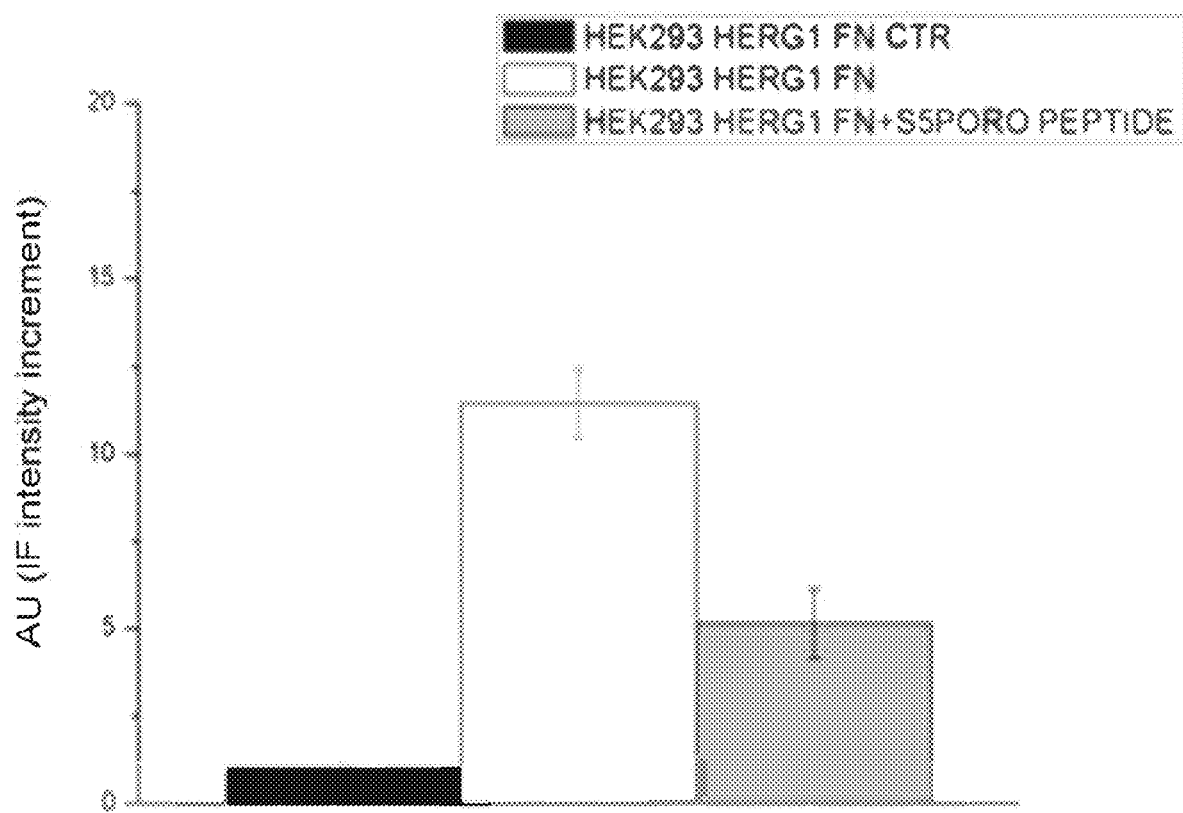

FIG. 14—Indirect IF performed on HEK 293 HERG1 cells (panels A and B). Staining of cells after administering of an excess of S5PORO peptide is shown in panels D and E. Panel C reports control cells stained only with secondary antibodies.

Figure 15A:
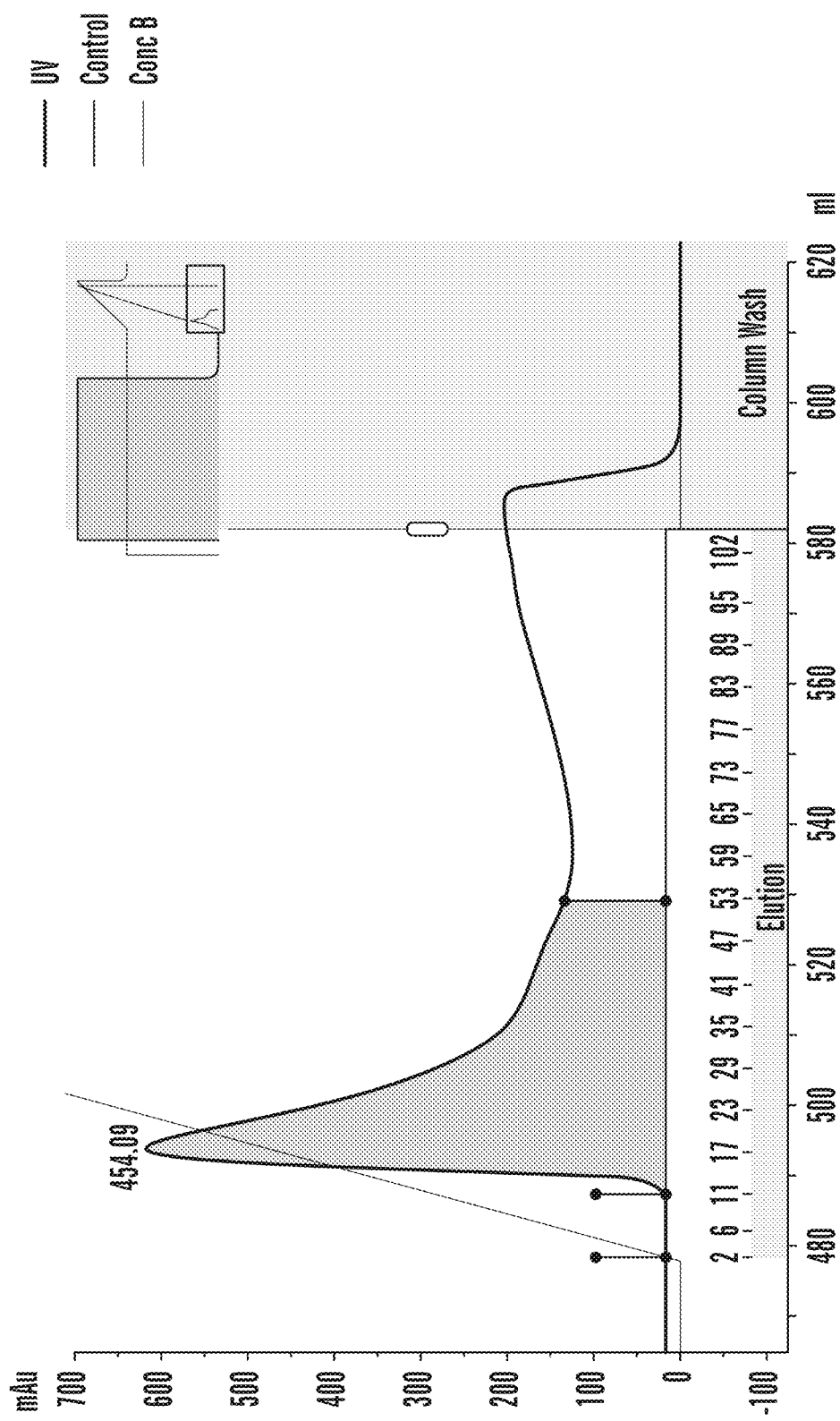
Figure 15B:
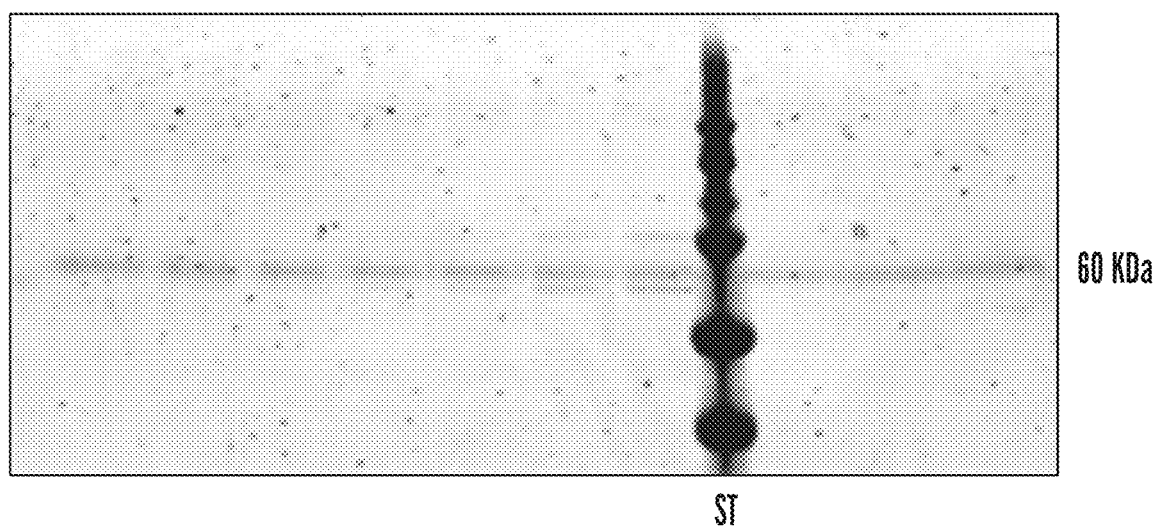

FIG. 15—Expression and purification of scDb-hERG1-Cys-β1. Panel A. Chromatogram resulting from the purification of *Pichia pastoris* supernatants. Panel B. Coomassie staining showing the analysis of the elutions from scDb-hERG1-Cys-β1 purification underlying the blue peak of the chromatogram.

Figure 16:
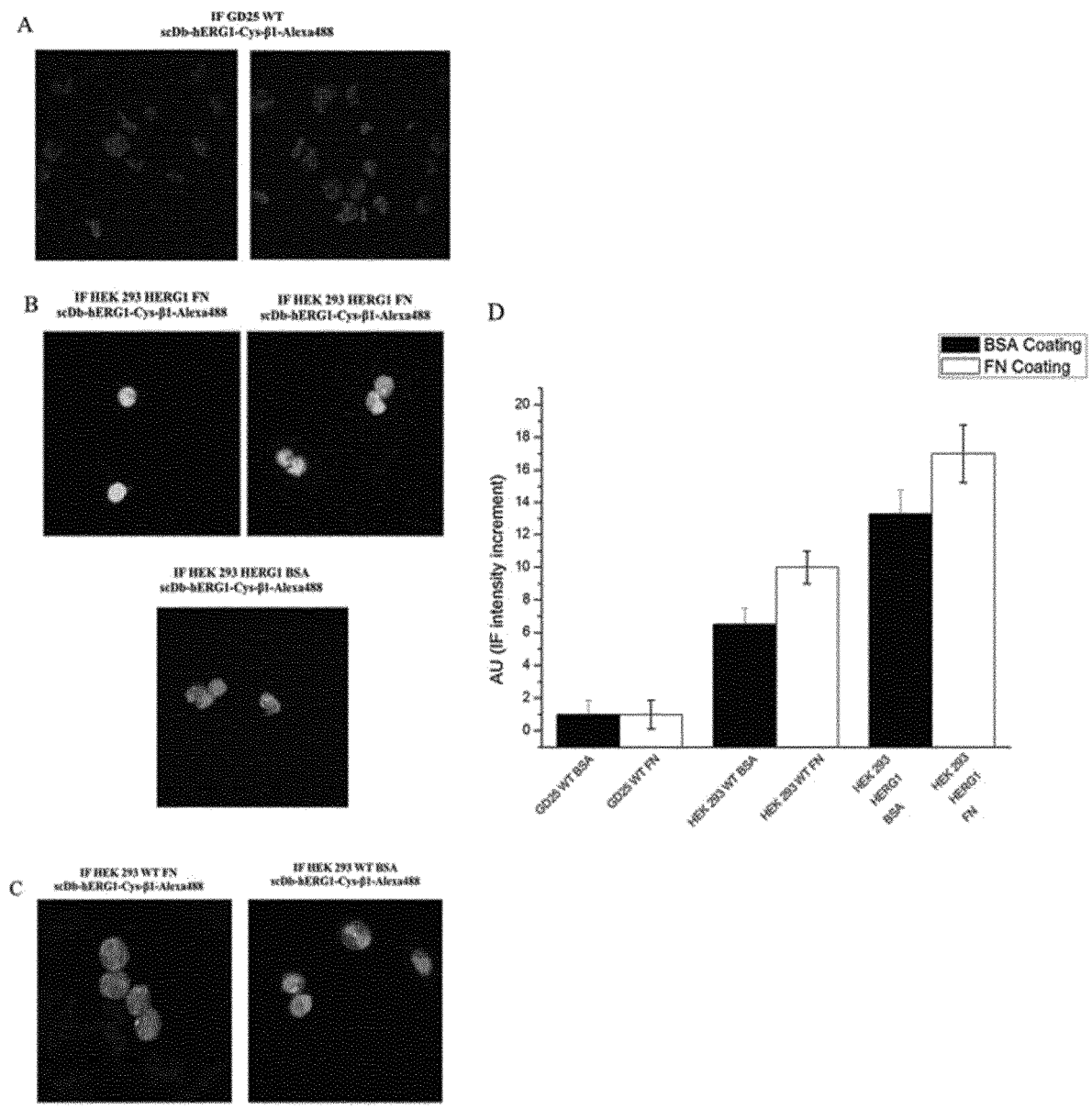

FIG. 16—Direct IF with scDb-hERG1-Cys-β1-Alexa488. In these particular experiments cells were incubated with scDb antibody directly conjugated with Alexa 488 fluorophore. GD25 WT cells (negative for both hERG1 and β1 integrin expression) incubated with scDb-hERG1-Cys-β1 antibody directly labelled with Alexa488 fluorophore. No signal is present. Panel B. HEK 293 HERG1 cells seeded on fibronectin (FN) and BSA and stained with scDb-hERG1-Cys-β1-Alexa488: as shown in the bar graph, signal is higher ($\cong$17 A.U) in cells seeded on FN compared to cells seeded on BSA ($\cong$10 A.U.). Panel C. HEK 293 WT cells seeded on FN and BSA and incubated with scDb-hERG1-Cys-β1-Alexa488: signal is lower for cells seeded on BSA ($\cong$7 A.U.), compared to cells seeded on FN ($\cong$12 A.U.). As it can be inferred from panels B and C, fluorescence values are lower for HEK 293 HERG1 cells on FN ($\cong$17 A.U), compared to HEK 293 WT cells seeded on FN ($\cong$12 A.U.).

FIG. 17—$IC_{50}$ determination on MDA-MB 231 and PANC-1 cells. An effect on cell viability was evident at 24 µg/ml for PANC-1 cells and 42 µg/ml for MDA-MB 231 cells.

Figure 18:
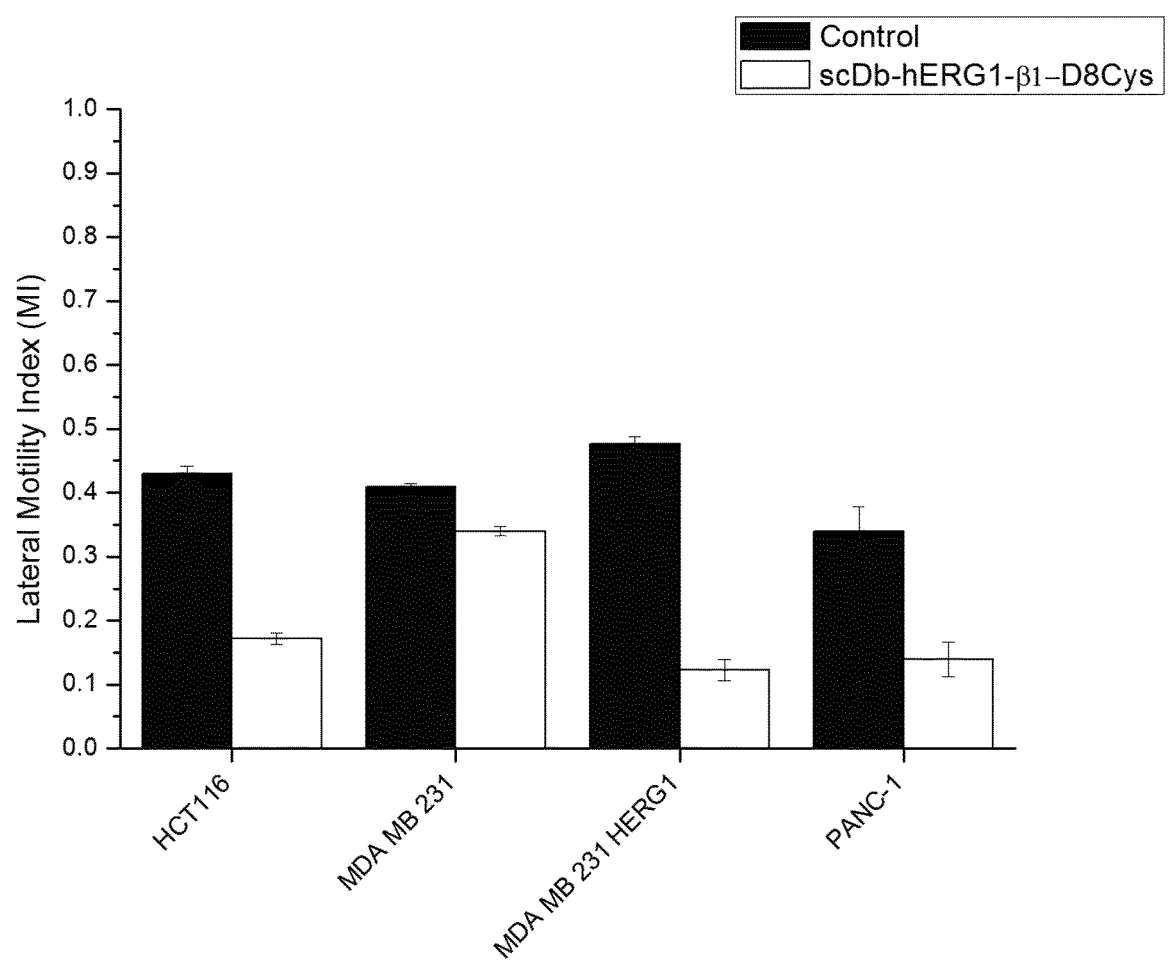

FIG. 18 Lateral motility experiments on HCT 116, MDA-MB 231 HERG1, MDA-MB 231 cells and PANC-1 cells. A clear reduction of the MI (Motility Index) is shown in cells treated with scDb-hERG1-Cys-β1, compared to control cells. A more pronounced effect is reported for MDA-MB 231 HERG1, compared to MDA-MB 231 cells, suggesting a hERG1 related effect on cell motility. Lateral motility experiments performed on PANC-1 cells, showing a lower MI on treated cells compared to the control. Lateral motility experiments performed on HCT116 cells, showing a lower MI on treated cells compared to the control.

Figure 19:
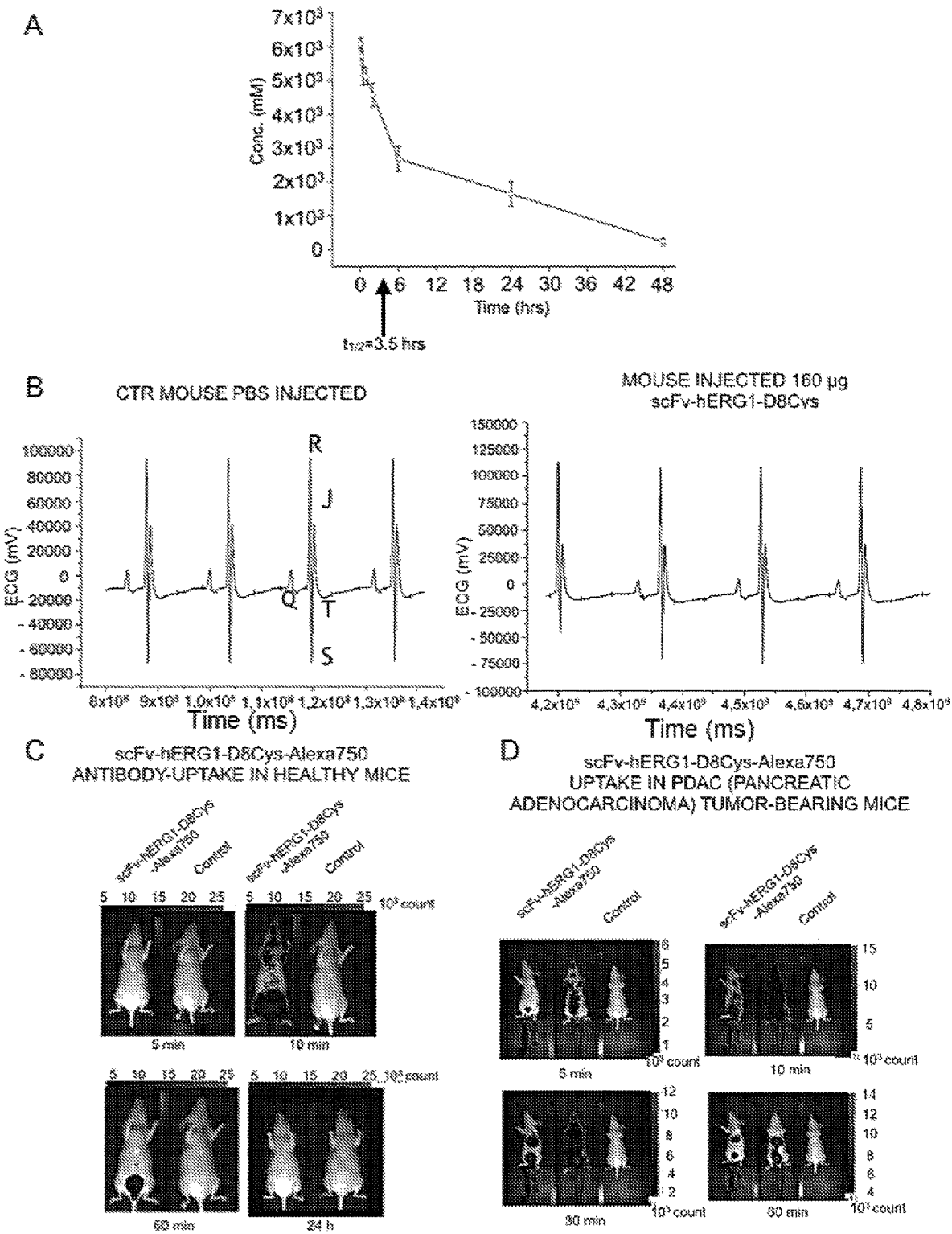

FIG. 19 (A) Pharmacokinetics of scFv-hERG1-D8Cys in mice by iv dosing (n=2). The antibody concentration has been determined by ELISA, dosing the plasma concentrations of mice blood samples collected 5, 15, 30 min and 1, 2, 6, 24 and 48 h after scFv injection. t1/2=3.5 h Values are means of two measurements±SD. (B) ECG, electrocardiogram registration. ECG measurements are reported in the left panel for the control mouse, injected with physiological solution, PBS, the adjusted value of the QT interval is 86 ms. The right panel shows the ECG graph obtained after the administering of scFv-hERG1-D8Cys, showing no significant changes compared to the control, with an adjusted value of the QT interval of 90 ms.

(C) In vivo analysis. Each panel reports the fluorescent signal in a representative mouse treated with scFv-hERG1-D8Cys antibody conjugated with Alexa750 compared to a control mouse treated with PBS solution. The maximum signal detected was at 10 minutes after the injection; and no fluorescence signal was detected after 24 hours from the intravenous administration.

(D) scFv-hERG1-D8Cys-Alexa750 uptake and retention of scFv-hERG1-D8Cys-Alexa750 in a MIAPaCa-2-nu/nu mice model of PDA. Mice were administered through tail vein injection with 6.5 µg of scFv-hERG1-D8Cys-Alexa750 antibody. Representative pictures of mice i.v. injected with the labelled antibody (left) have been compared with control mice (right). Fluorescence intensity in the abdominal area, the site proximal to tumor has been analyzed. Fluorescent emission spectra were measured using Photon imager (Biospace Lab), images have been acquired at different time-points, every 5 min, starting 5 min after injection until 60 min after injection.

FIG. 20. (A) Pharmacokinetics of scDb-hERG1-Cys-β in mice by iv dosing (n=2). The antibody concentration has been determined by ELISA, dosing the plasma concentrations of mice blood samples collected 5, 15, 30 min and 1, 2, 6, 24 and 48 h after scDb injection. t½$\cong$12 h Values are means of two measurements±SD.

(B) ECG, electrocardiogram registration. The ECG graph obtained after the administering of scDb-hERG1-Cys-β1 antibody shows no significant changes compared to the control graph reported in FIG. 20B, with an adjusted value of the QT interval of 83 ms, comparable to the Control.

(C) Table showing the pancreas volume (mm$^3$) of MIAPaCa-2-nu/nu tumor-bearing mice treated and untreated with the scDb-hERG1-Cys-β1 antibody. Metastatic diffusion, % of necrotic area in the slide and number of vessels are also reported.

(D) Images of pancreas after nescroscopy: 1, untreated; 2, treated with three doses of scDb-hERG1-Cys-β1 antibody; 3, treated with six doses of scDb-hERG1-Cys-β1 antibody.

EXPERIMENTAL SECTION

1. scFv-hERG1 Mutagenesis

Figure 1:
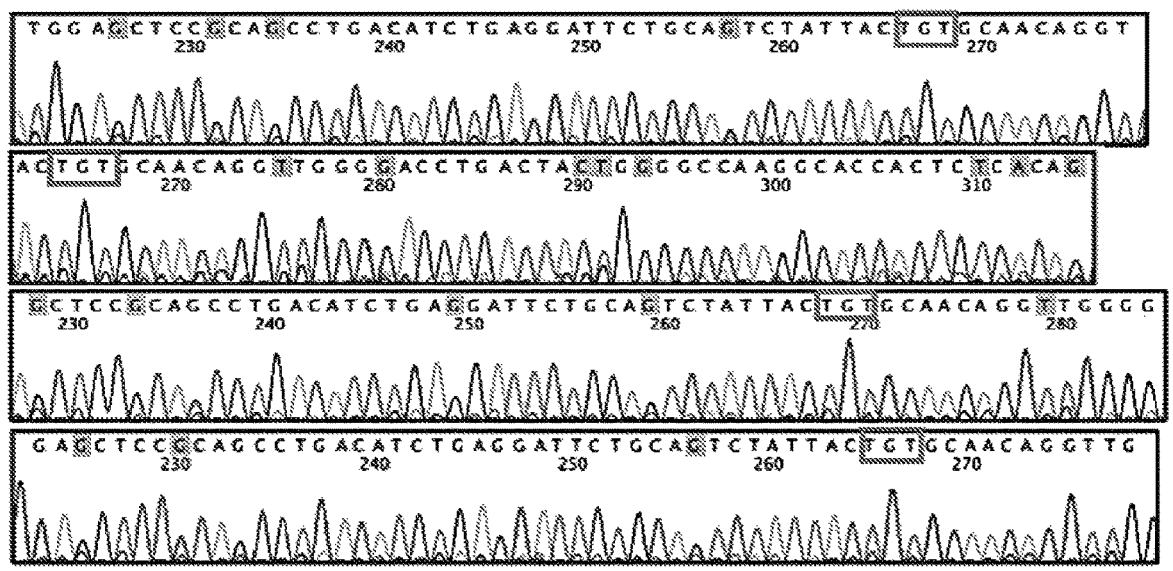
FIG. 1—Electropherograms obtained from the DNA sequencing of four colonies after the mutagenesis performed on scFv-hERG1 construct, showing the proper mutation from Phe to Cys.

The amino acid sequence of the scFv hERG1 molecule as described in WO2016020483 (A1) presents the amino acid Phe in position 95 of the VH domain. The nucleotide sequence SEQ ID No: 1 unraveled the presence of T in position 283 (c283T) of the VH domain. According to the present invention, the substitution of a G was introduced instead of the T in position 283 (c283T>G) of the VH domain leading to the switch of the Phe (TTT) in position 95 with a Cys (TGT). This mutation resulted in the introduction of one amino acid (Cys) in the position between Framework 3 and CDR3, which surprisingly resulted fundamental for the formation of the disulfide bond in the immunoglobulin variable domain. The Cys was introduced in the original construct, setting up a mutagenesis protocol (see Materials and Methods). The cDNA obtained from four mutagenized scFv-hERG1 colonies was sequenced and the sequencing results (FIG. 1) demonstrated the proper mutation from TTT to TGT in position c283T>G, indicative of the desired mutation from Phe to Cys.

2. Expression and Protein Purification

Figure 2:
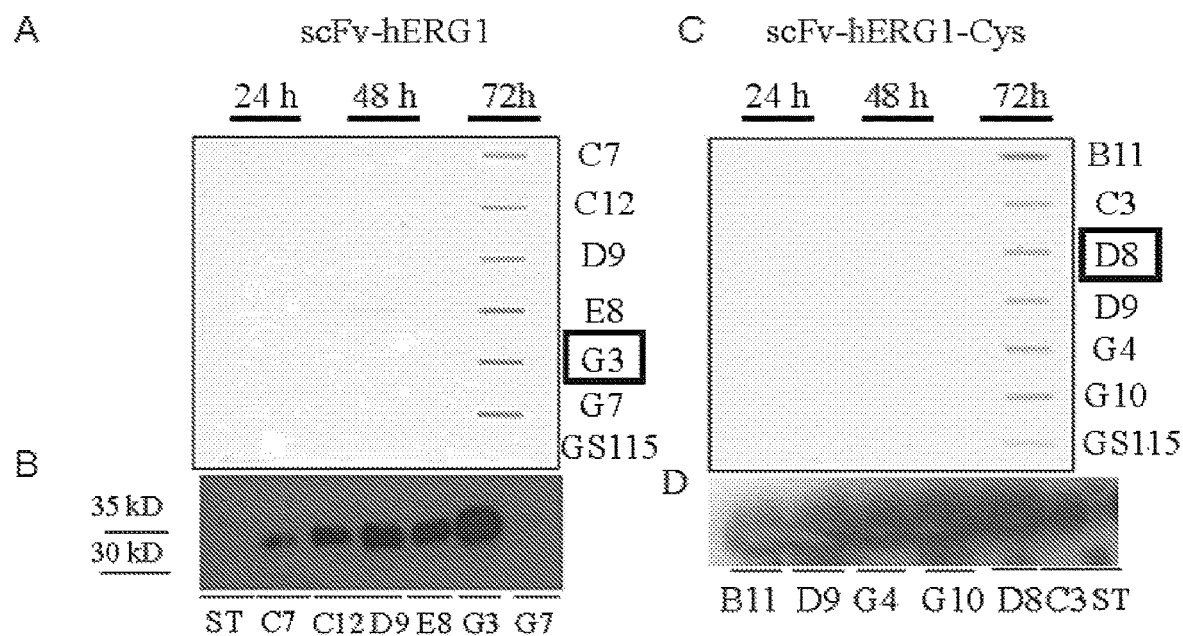
FIG. 2—(A): Yeast expression of scFv-hERG1. Slot blot on supernatants collected from induction of scFv-hERG1-G3 *Pichia pastoris* clones at 24 h, 48 h and 72 h. Clones C7, C12, D9, E8, G3, G7 and the negative control of non-transformed *Pichia* strain GS115 were all analyzed. Stained was performed using DAB chromogene. G3 is shown being the best expressing one. (B): Western-blot performed on purified samples of the six clones. G3 showed the highest expression level, while almost no expression was detected for the G7 clone. (C): Slot blot on supernatants collected from induction of scFv-hERG1-D8Cys *Pichia pastoris* clones at 24 h, 48 h and 72 h. Clones B11, C3, D8, D9, G4, G10 and the negative control of non-transformed *Pichia* strain GS115 were all analyzed. Stained was performed using DAB chromogene. D8 is shown being the best expressing one. (D): Western-blot performed on purified samples of the six clones. D8 was the one that showed the highest expression level, while lower expression was detected for the C3 clone.

Either plasmids, scFv-hERG1 and the mutagenized scFv-hERG1 (hence named scFv-hERG1-Cys), were transformed into GS115 *P. pastoris* host strain, using the spheroplasting technique. Six clones (C7, C12, D9, E8, G3, G7) among the scFv-hERG1 transformants and six (B11, C3, D8, D9, G4, G10) from the scFv-hERG1-Cys were analyzed. Results of the small-scale expression are shown in FIG. 2 panels A and B for scFv-hERG1 and panels C and D for scFv-hERG1-Cys, respectively.

All the clones revealed protein expression after 72 h induction (upper panels), as also shown in slot blot.

After purification, the presence of the protein was assessed through western-blot (panel B and D).

The two best expressing clones were chosen for the two antibodies: G3 for scFv-hERG1 (hereafter named scFv-hERG1-G3) and D8 for scFv-hERG1-Cys (named scFv-hERG1-D8-Cys).

Larger-scale expression analyses are shown in FIG. 3. The presence of the protein was assessed through SDS-PAGE and Coomassie Brilliant Blue staining. Fractions 11, 12, 13 (A, left panel) correspond to scFv-hERG1-G3; fractions 12, 13, 14 (B, right panel) correspond to scFv-hERG1-D8Cys. Bands corresponding to the molecular size of both antibodies (around 30KDa) are visible. Comparing the yields of the two proteins, scFv-hERG1-G3 and scFv-hERG1-D8Cys, significant differences were found: scFv-hERG1-G3 concentration is 0.050 µg/µl; scFv-hERG1-D8Cys concentration is 0.444 µg/µl.

| PROTEIN | YIELD (mg/l) |
| --- | --- |
| scFv-hERG1-G3 | 0.200 |
| scFv-hERG1-D8Cys | 1 |

*The yields were normalized to mg protein per liter of *Pichia Pastoris* yeast culture.

3. Comparison of Antigen Affinity Between scFv-hERG1-G3 and scFv-hERG1-D8Cys Chromatograms reported in FIG. 3 (panels B) show the results obtained from gel filtration. Size-exclusion chromatography (SEC) was performed in order to investigate the possible presence of aggregates which might affect the binding capacities of the two antibodies. Several aggregates are detectable from the analysis reported in B (left panel) that refers to scFv-hERG1-G3; instead scFv-hERG1-D8Cys (B, right panel) appears in a monomeric form.

4. scFv-hERG1-D8Cys Antibody Stability Test

The stability of the scFv-hERG1-D8Cys antibody was directly assessed analyzing the protein through SDS-Page Coomassie Brilliant blue staining at different time points (6, 12, 18 months) after purification. Data in FIG. 3C show that only one neat single band is visible at all time points, thus indicating that the protein maintains its stability without showing signs of degradation.

5. Evaluation of Immunoreactivity of scFv-hERG1-G3 and scFv-hERG1-D8Cys

Then an immunofluorescence analysis was performed using scFv-hERG1-G3 and scFv-hERG1-D8Cys on fixed cells, to determine the immunoreactivity of the two antibodies. Were used, as cellular model, HEK 293 transfected with the hERG1 cDNA (HEK-hERG1) and, as a control HEK-MOCK, that do not express the hERG1 protein. HEK-MOCK cells showed no or weak signal with both antibodies, while HEK 293 hERG1 showed a good labeling with the scFv-hERG1-G3 and, even better, with the scFv-hERG1-D8Cys (FIGS. 4, A and B). Data analysis obtained using ImageJ Software is reported in the graphs reported in panel C. Values obtained from scFv-hERG1-D8Cys staining are significantly higher in cells overexpressing hERG1, if compared to the values of the control obtained in HEK-MOCK cells.

It was also tested the immunoreactivity of the two antibodies after direct labelling with the fluorescent molecule Alexa 488. scFv-hERG1-G3-Alexa488 and scFv-hERG1-D8Cys-Aexa488 antibody was tested in IF on fixed cells (FIGS. 4, A and B) showing the maintaining of the capacity to recognize the antigen in the native conformation, even after the conjugation with the fluorophore. IF staining was measured using ImageJ software and results are reported in the graphs reported in panel C. Signal obtained on HEK 293 HERG1 cells is stronger compared to the control HEK-MOCK cells both for scFv-hERG1-G3-Alexa488 and scFv-hERG1-D8Cys-Alexa488.

In order to assess and compare the potential use in vivo of scFv-hERG1-G3-Alexa488 and scFv-hERG1-D8Cys-Alexa488 as molecular tools, both antibodies were used in IF on live cells (FIGS. 4 A and B).

The experiment confirmed the results obtained with the staining on fixed cells; HEK293 hERG1 cells appear to have a stronger signal, if compared with the negative control HEK293 MOCK cells. HEK 293 hERG1 cells appear to have a more specific spotty cellular labelling, while HEK-MOCK cells have a non-specific diffuse background. For this reason, it has been reported the bright-field image of the same section.

6. scFv-hERG1-D8Cys Antibody Viability Inhibition and Spheroids Test

At this stage, it has been further explored the potential capacity of scFv-hERG1-D8Cys of inhibiting cell growth on a panel of neoplastic cell lines. As reported in FIG. 5, a significant dose-dependent inhibition of cell proliferation was observed for HCT-116, MDA-MB 231, Mia Paca-2, HEK 293 HERG1, PANC-1 and BxPc3. Cells were treated using anti-hERG1 monoclonal antibody (100 µg/ml) and scFv-hERG1-D8Cys (10; 20 µg/ml). As expected, no significant decrease in cell viability was found in HEK-MOCK cells, which do not express hERG1.

In order to investigate the effect of scFv-hERG1-D8Cys on a 3D cellular model we have tested three different concentrations of scFv-hERG1-D8Cys (10; 20; 40 µg/ml) on spheroids.

FIG. 6 shows the graph reporting on the Y axis the volume of the spheroids (mm³), while on the X axis are reported the different timepoints (24 h, 48 h and 72 h).

In FIG. 6, panel A is reported the graph obtained for spheroids generated from HEK293-hERG1. The volume of the spheroids treated with 20 µg/ml and 40 µg/ml scFv-hERG1-D8Cys is smaller compared to the control at each timepoint. Panel B, instead, shows the growth curve of the HEK-MOCK spheroids, in which no difference was found for treated spheroids at all the three concentrations scFv-hERG1-D8Cys tested, compared to the control. Panel A and B also show a representative brightfield image of the control HEK293-hERG1 and HEK-MOCK spheroids, respectively, as they appeared after 72 h colture.

Panel C shows the effect obtained on pancreatic ductal adenocarcinoma Mia Paca 2 cells. A decrease in the volume of spheroids was observed both for cells treated with 20 µg/ml and 40 µg/ml scFv-hERG1-D8Cys, with a more pronounced effect obtained at the highest concentration tested compared to the controls, at each timepoint. Images taken at 72 h, reported on the right part of the figure, show a picture of a control spheroid of Mia Paca 2 taken at 4× magnification; while the right image shows a picture of a Mia Paca2 spheroid treated with 40 µg/ml scFv-hERG1-D8Cys, taken at 10× magnification. In fact, it wasn't possible to acquire pictures of control Mia Paca 2 spheroids after 72 h with 10× magnification, as the volume was too enlarged to allow a proper focusing; while Mia Paca 2 spheroids at 72 h treated with scFv-hERG1-D8Cys can be visualized using 10× magnification, as their volume, compared to control, was strongly reduced.

Panel D shows MDA-MB 231 spheroids: a marked effect of volume reduction is observed for all the three concentrations of scFv-hERG1-D8Cys tested (10, 20, 40 µg/ml) compared to the control. Volume reduction can be inferred also from the pictures of MDA-MB 231 spheroids reported on the right side of the figure.

FIG. 7 shows the results obtained from Calcein AM cell viability assay performed on spheroids after 72 h. Green staining represents live cells, while red staining represents dead cells. Image on the left (panel A) are pictures of the control for each cell line, while on the right side (panel B) there are pictures of spheroids treated with 40 µg/ml scFv-hERG1-D8Cys. From the image it is possible to note the volume reduction for spheroids treated with the antibody, especially for Mia Paca 2, MDA MB-231 and PANC-1 spheroids and, moreover, an increased number of dead cells, especially for MDA MB-231 and PANC-1 spheroids treated with scFv-hERG1-D8Cys.

7. ScDb-hERG1-β1 It has been developed a bispecific antibody (bsAb) comprising a single chain antibody directed against β1-integrin (scFv-TS2/16) and a scFv-hERG1-Cys or scFv-hERG1 (as above described).

Nucleotide sequence encoding VL domain of TS2/16 is SEQ ID No: 23; nucleotide sequence encoding VH domain of TS2/16 is SEQ ID No: 25 (see FIG. 8); respectively VL amino acid sequence of TS2/16 is SEQ ID No: 24 and VH amino acid sequence of TS2/16 is SEQ ID No: 26.

The bispecific antibody format is the single-chain diabody (scDb), which comprising the variable domains (VH and VL) of two antibodies, connected by peptide linkers, as showed in FIG. 9. The upper panel of the figure reports the two single-chain antibodies, anti-hERG1 scFv and anti-β1-integrin TS2/16, scFv antibody.

The lower panel schematizes the final structure of the bispecific antibody anti-hERG1-β1-integrin, which has been assembled using the variable domains of the two antibodies in the following order: VH scFv-hERG1 antibody (SEQ ID No: 8 or SEQ ID No: 2), VL scFv-TS2/16 antibody (SEQ ID No: 24), VH scFv-TS2/16 antibody (SEQ ID No: 26), VL scFv-hERG1 antibody (SEQ ID No: 4).

VL scFv-TS2/16 antibody (SEQ ID No: 24) and VH scFv-TS2/16 antibody (SEQ ID No: 26), are linked by peptide linker.

VH scFv-hERG1 antibody (SEQ ID No: 2 or 8) and VL scFv-TS2/16 antibody (SEQ ID No: 24) are linked by a peptide linker.

VH scFv-TS2/16 antibody (SEQ ID No: 26) and VL scFv-hERG1 antibody (SEQ ID No: 4) are linked by a peptide linker At 5' and 3' ends were inserted the FspI and AvrII restriction sites (reported underlined below)

VLFspI:
(SEQ ID No: 27)
AAAA<u>TGCGCA</u>GACTACAAAGATATTGTGATGACACAGAC

VHAvrII:
(SEQ ID No: 28)
GGGG<u>CCTAGG</u>ATAGACAGATGGGGGTGTCGCGACACCCCATCTGTCTAT.

The following sequence (SEQ ID No: 29) is the complete nucleotide sequence encoding for the scDb-hERG1-β1 (SEQ ID No: 30): scFv-hERG1-Cys VH sequence is reported highlighted in grey, VL sequence of scFv-TS2/16 is reported in underlined italics, in bold are reported A, M, B linker sequence, in underlined bold italics is reported VH sequence of scFv-TS2/16 antibody, in underlined highlighted in grey is reported VL sequence of scFv-hERG1-Cys.

Myc-tag is reported in italics bold, while His-tan is reported underlined in bold.

Restriction sites are reported underlined.

SEQ ID No 29:
GAGGCTGAGT<u>GCCCAG</u>ACGAGGTCCAACTGCAACAGTCTGGACCTGAACT

GGTGAAGCCTGGGGCTTCTGTGAAGATATCCTGCAAGACTTCAGGATACA

CATTCACTGAATACACCGTTCACTGGGTGAAACAGAGCCATGGAAAGAGC

CTTGAATGGATTGGAGGCATTAATCCTAATGGTGGTACTACCTATAATCA

GAAGTTCAAGGGCAAGGCCACATTGACTATTGACAAGTCCTCCAGCTCAG

CCTTCATGGAGCTCCGCAGCCTGACATCTGAGGATTCTGCAGTCTATTAC

TGTGCAACAGGTTGGGGACCTGACTACTGGGGCCAAGGCACCACTCTCAC

AGTCTCCTCAGCCAAAACAACACCCCCATCAGTCTATCCACTGGCCCCTG

GCTCGAGT<u>*GATATTGTGATGACACAGACTCCAACCACCATGGCTGCATCT*</u>

<u>*CCCGGGGACAAGATCACTATCACCTGCAGTGTCAGTTCAATTATAAGTTC*</u>

<u>*CAATTACCTGCATTGGTATAGTCAGAAGCCAGGATTCTCCCCTAAACTCT*</u>

<u>*TGATTTATAGGACATCCAATCTGGCTTCTGGAGTCCCACCTCGCTTCAGT*</u>

<u>*GGCAGTGGGTCTGGGACCTCTTACTCTCTCACAATTGGCACCATGGAGGC*</u>

<u>*TGAAGATGTTGCCACTTACTACTGCCAGCAGGGGTTCTGATATTCCACTCA*</u>

-continued

```
CGTTCGGTGATGGGACCAAGCTGGACCTGAAACGGGCTGATGCTGCACCA

ACTGTATCCGGTGGTGGTGGTTCTGGTGGTGGTGGTTCTGGCGGCGGCGG

CTCCGGTGGTGGTGGATCCGAGGTGAAGGTGGTGGAATCTGGGGGA

GGCTTAGTGAAGCCTGGAGGGTCCCTGAAACTCTCCTGTGCAGCCTCTGGA

TTCACTTTCAGTAGCTATACCATGTCTTGGGTTCGCCAGACTCCGGAGAA

GAGGCTGGAGTGGGTCGCAACCATAAGTAGTGGTGGTTCTTACA

CCTACTATCCAGACAGTGTGAAGGGCCGATTCACCATTTCCAGA

GACAAAGCCAAGAACACCCTGTATTTGCAAATGGGCAGTCTGAA

GTCTGAGGACACAGCCATGTATTACTGTACAAGAATAGG

TTACGACGAAGATTATGCTATGGACCACTGGGGTCAAGGAACC

TCAGTCACCGTCTCCTCAGCCAAAACGACACCCCATCT

GTCTATAGTGCACTGGATATTGTGCTGACACAATCTCCACTCACTTTG

TCGGTTAACATTGGTCAACCAGCCTCTATCTCTTGCAAGTCAAGTCAG

AGCCTCTTATATACTAATGGAAAAACCTATTTTAATTGGTTATTACAG

AGGCCAGGCCAGTCTCCAAAGCGCCTAATCTATCTGGTGTCTAAACTG

GACTCTGGAGTCCCTGACAGGTTCACTGGCAGTGGATCAGGAACAGAT

TTTACACTGAAAATCAGCAGATGGAGGCTGAAGATTTGGGAGTTTAT

TACTGCGCGCAAGGTACACATTTTCCGTGGACGTTCGGTGGAGGGACC

AAGCTGGAAATCAAACGGGCTGATGCTGCACCAACTGTATCCGCGGCC

GCAGAACAAAAACTCATCTCAGAAGAGGATCTGAATGGGCCCCTAGG

CATCATCACCATCACCATCATCACTAATAG
```

The sequence has been cloned, using the restriction sites indicated above, into the commercially available vector pPIC9K (Life Technologies).

8. scDb-hERG1-Phe-β1: Expression and Characterization

The construct expressing anti-hERG1-Phe-β1-scDb antibody has been cloned into pPIC9K expression vector, which is a vector suitable for expression in *Pichia pastoris* yeast cells.

GS115 *Pichia pastoris* strain was transformed, according to the spheroplasting protocol and 96 clones were screened on YPD-agar plates containing G418 for selection. Six clones were then induced on a small scale and purified using Sepharose Ni beads (GE Healthcare), exploiting the Histidine tag introduced with the pPIC9K vector. Coomassie staining is reported in FIG. 11, panel A, and it shows one band, highlighted by the arrow, with a molecular weight (around 60 KDa) consistent with the one expected for the anti-hERG1-Phe-β1-scDb antibody, corresponding to clone G5.

Then it was started large-scale expression of the G5 anti-hERG1-Phe-β1-scDb clone, adapting the induction protocol for bigger culture volumes.

Supernatant resulting from 1 L *Pichia pastoris* cells culture has been purified using AKTA Pure (GE Healthcare). Results are reported in FIG. 11, in which is shown both the chromatogram resulting from the antibody purification (panel B), as well as the Coomassie staining (panel C) in which elutions underlying the blue area have been analyzed. Consistently with what expected a single band, corresponding to the purified anti-hERG1-Phe-β1-scDb has been detected for each elution.

Anti-hERG1-β1-scDb fractions 8; 9; 10; 11; 12; 13; 14; 15; 16; 18; 20 were gathered together, and dialyzed against PBS 1×. Thus, a detailed characterization of the antibody was started.

One of the crucial steps was the choice of a proper model to test the anti-hERG1-Phe-β1-scDb antibody. The table below summarizes the expression profile related to hERG1 and β1 integrin of the cell lines, chosen for characterization experiments.

TABLE

HEK 293 HERG1, HEK 293 WT and GD25 expression profile related to hERG1 and β1 integrin

|  | hERG1 EXPRESSION | β1 integrin EXPRESSION |
|---|---|---|
| HEK 293 hERG1 | + | + |
| HEK 293 WILD TYPE | − | + |
| GD25 | − | − |

The bsAb was first analyzed on HEK 293 hERG1 cells which express both hERG1 and β1 antigens. Cell-ELISA was performed and results are reported on FIG. 12, cell-ELISA showed a certain dose-dependent proportionality for the binding with the native antigen, with higher $OD_{450}$, for cells expressing both hERG1 and β1 antigens, as expected.

Moreover, the anti-hERG1-β1-scDb bispecific antibody showed the capacity to bind the antigen in native conditions, as it is for the antigen endogenously expressed by cells. Binding specificity of anti-hERG1-Phe-β1-scDb bispecific antibody is also corroborated by the comparison between the same amount (0.5 μg) of anti-hERG1-Phe-β1-scDb and anti-scFv-hERG1-Phe, which is one of the two single-chain antibodies that form the bispecific antibody. In fact, the signal obtained after incubating with anti-hERG1-Phe-β1-scDb is higher than the one obtained using anti-scFv-hERG1-Phe. Such result is in line with what expected, since the signal obtained with anti-hERG1-Phe-β1-scDb results from the binding to both antigens, hERG1 and β1; while the signal obtained using scFv-hERG1 results from the binding to hERG1 antigen, only.

It has also been evaluated the immunoreactivity of the anti-hERG1-Phe-β1-scDb antibody through IF, on cells grown on BSA (FIG. 13, panel A and B) and fibronectin (FN) substrates (FIG. 13, panel C and D). In fact, it has been shown that β1 complex formation is enhanced by FN-dependent integrin activation. As it can be seen from FIG. 13, panels C and D, is displayed a strong membranous signal in cells HEK293-hERG1 seeded on Fibronectin, due to a strict complex formation. The signal has been analyzed using ImageJ software and results are reported in the graph.

To further confirm the evidences obtained from previous experiments, it has been evaluated the binding of anti-hERG1-Phe-β1-scDb, on HEK293-hERG1 cells administering, before antibody incubation, an excess of peptide S5PORO, which is the peptide towards which the scFv-hERG1 antibody is directed. As it can be inferred from FIG. 14, panels A and B, the signal on HEK293-hERG1 cells incubated with anti-hERG1-Phe-β1-scDb, due to the binding both to hERG1 and to β1 integrin, is confirmed. Panel C shows the negative control, while panels D and E show the results obtained after incubation with S5PORO peptide; it is clearly visible that there is a reduction in the signal which is consistent with what expected. In fact, HEK293-hERG1 cells that are positive for both antigens, after incubation with the peptide show a reduction in staining intensity probably due to the saturation of the hERG1 antigen binding sites; thus the signal that is visible is the one originated only from the binding to β1 antigen. Such results are summarized in the graph obtained from ImageJ fluorescence intensity quantification.

9. scDb-hERG1-Cys-β1: Expression and Characterization

The construct expressing scDb-hERG1-Cys-β1 antibody cloned into pPIC9K expression vector, which is a vector suitable for expression in *Pichia pastoris* yeast cells, has been transformed into GS115 yeast cells.

Clones derived from scDb-hERG1-Cys-β1 transformation have been screened according to the protocol previously described for scDb-hERG1-Phe-β1 antibody. Supernatant resulting from 1 L *Pichia pastoris* cells culture has been purified using AKTA Pure (GE Healthcare). Results are reported in FIG. 15, in which both the chromatogram resulting from the antibody purification (panel A), as well as the Coomassie staining (panel B) are shown. Elutions underlying the blue area have been analyzed and, consistently with what expected, a single band with a molecular weight of roughly 60 KDa, corresponding to the purified scDb-hERG1-Cys-β1, has been detected for each elution.

After the successful protein purification, the antibody has been tested in direct immunofluorescence (IF) after direct conjugation with Alexa488. Results are reported in FIG. 16 for GD25 WT, HEK 293 WT and HEK 293-hERG1 cells. Images show that GD25 WT cells, panel A, (negative for both hERG1 and β1 integrin expression) present no significant staining after incubation with scDb-hERG1-Cys-β1 antibody, while panel B shows a clear membranous staining for HEK 293-hERG1 cells (which express both antigens), seeded on fibronectin (FN) which has the action of enhancing the hERG1-β1 complex formation, with a higher fluorescence signal value ($\cong$17 A.U.) compared to cells seeded on BSA, used as control ($\cong$10 A.U.). Panel C shows the fluorescent staining obtained on HEK 293 WT cells (which express only β1 integrin), showing higher fluorescence signal values for cells seeded on FN ($\cong$12 A.U.), compared to cells seeded on BSA ($\cong$7 A.U.). The $IC_{50}$ has been determined for both cell lines as shown in FIG. 17, panels A and B. An effect on cell viability was evident at 24 μg/ml for PANC-1 cells and 42 μg/ml for MDA-MB 231 cells. Such findings are consistent with the pattern of hERG1 expression, whose expression is predominant in PANC-1 cells, compared to MDA-MB 231 cells.

It has been thus tested the effect of scDb-hERG1-Cys-β1 on cancer cell migratory behavior through lateral motility assay. Experiments have been performed on MDA-MB 231, MDA-MB 231-hERG1, PANC-1 and HCT116 cells. Results are reported in the graphs in FIG. 18. There is a clear reduction of the motility index (MI) in treated cells compared to control. Such effect is more pronounced on MDA MB 231-hERG1, compared to MDA-MB 231 cells, suggesting a hERG1-dependent effect of the antibody on cell migration.

Promising results have also been obtained on PANC-1 and HCT116 cells, with a reduction of motility behavior in treated cells compared to controls Materials and Methods 10. Cloning of the Heavy and Light Chain of the hERG1 Antibody.

The heavy and light chain of the monoclonal antibody against hERG1 (hERG1-mAb) were isolated from cDNA obtained from the mRNA purified from hybridomas secerning hERG1-mAb. For the amplification of VH and VL regions, a 5' primer that anneal to the framework 1 (FR1) of the variable domain of each chain (primer forward) and a primer that anneal to the constant region near the variable domain of each chain (primer reverse) were chosen. For VL was designed a degenerate primer that anneal to the kappa light chain, since this is the immunoglobulin phenotype more expressed in mice (Honjo and Alt, 1995). The heavy chain (VH) of antibody was amplified by PCR using the following set of primers: degVH forward, 5' GAGGTCCA-RCTGCAACARTC 3' (SEQ ID No: 11) and IgG2 reverse, 5' AGGGGCCAGTGGATAGACTGATGG 3' (SEQ ID No: 12) (Wang, 2000). The following set of primers was used to PCR amplify the light chain (VL) of antibody: degVL(K), 5' GAYATTGTGMTSACMCARWCTMCA 3' (SEQ ID No: 13) and K reverse, 5' GGATACAGTTGGTGCAGCATC 3' (SEQ ID No: 14) (Wang, 2000). The cDNA was amplified using Phusion® High-Fidelity DNA Polymerase (Finnzymes Reagents). Cycling conditions were: initial melt at 94° C. for 2 min followed by 25 cycles of a three-step program (94° C., 30 sec; 56° C. (VH); 48° C. (VL), 1 min; and 72° C., 1 min. The reactions were then held at 72° C. for 10 min and cooled to 4° C.

The antibody fragments (VH and VL) isolated from agarose gel elecrophoresis, were purified using QIAquick PCR Purification Kit (QIAGEN) and then inserted into pCR™-Blunt vector (Invitrogen) following the manufacturer's instructions. The recombinant plasmid were sequenced through Automated DNA sequencing service (PRIMM). VH and VL fragments were then cloned into pHENIX expression vector, which contain the linker sequence (Gly4Ser) 3between two different cloning sites. Primers with appropriate restriction sites to clone antibody fragments into pHenIX vector were designed. VL primers: forward VL-ApaLI, 5' acgcgtgcactgGATAT-TGTGCTGACACAATCTCCA 3'(SEQ ID No: 15); reverse VL-NotI, 5' ataagaatgcggccgcGGATACAGTTGGTGCAG-CATC 3'(SEQ ID No: 16). VH primers: forward VH-Salk, 5' acgcgtcgacGAGGTCCAACTGCAACAGTC 3'(SEQ ID No: 17); reverse VH-XhoI, 5' ccgctcgagccAGGGGCCAGTGGATAGACTGATGG 3'(SEQ ID No: 18). PCR products were digested either with ApaLI and NotI (for VH) or SalI and XhoI (for VL) restriction enzymes (New England BioLabs) and ligated into pHENIX vector in the compatible cloning sites. Digestion were performed 2 h at 37° C. To avoid re-ligation of compatible ends, the 5' phosphate group was removed from the 5' terminus of the vector using the calf intestine phosphatise (CIP) according to the following protocol: pHENIX vector (50 ng/μl), Buffer 3 (New England BioLabs) 1× and CIP (0.5 u/μg of vector). Dephosphorylation reaction was incubated for 1 hour at 37° C. Phosphorylated vector was purified with QIAquick PCR Purification Kit (QIAGEN).

Ligations between the scFv-hERG1 fragment and pHENIX were performed in a mixture of Buffer 2 (New England BioLabs) and T4 Ligase. Vector: scFv ratios of 1:3 and 1:10 were set up in the ligation mixture and incubation was done 15 min at 25° C.

2 μl of the ligation mixture were electroporated into *E. coli* TOP10F' and HB2151 cells (2500 mV pulse). The electroporated cells were recovered with 450 μl SOC medium (SOB medium supplemented with 1 mM $MgSO_4$, 1 mM $MgCl_2$) and incubated 1 hour at 37° C. on shaking. Bacteria were plated into pre-warming LB-Agar plates containing antibiotic and incubated lid-side down overnight at 37° C.

11. Cloning of scFv-hERG1-G3 in pPIC9K Expression Vector

The scFv-hERG1 expression cassette was cloned into a transformed pPIC9K vector (kindly gifted by Prof. Ermanno Gherardi, University of Pavia), which contain a 6×His tag. The scFv construct was isolated and amplified from pHENIX vector by PCR using primers which allow the addiction of FspI and AvrII restriction sites respectively at 3' and 5' ends of the sequence (forward VH-FspI, AAAATGCGCAGAGGTCCAACTGCAACAGTC (SEQ ID No: 19); reverse VL-AvrII, GGGGCCTAGGGGATA-CAGTTGGTGCAGCATC (SEQ ID No: 20)).

The vector pPIC9 is composed of the AOX1 promoter, 3'AOX1 transcriptional terminator (TT), and a multi-cloning site into which a foreign gene is inserted.

The expression cassette was cutted with FspI and AvrII and cloned into pPIC9K cut with Eco53KI and AvrII restriction enzymes (New England BioLabs).

12. scFv-hERG1 Mutagenesis

Mutagenesis was performed on the scFv-hERG1 expression cassette cloned into pPIC9K using the QuikChange® XL Site-Directed Mutagenesis Kit (Stratagene, Agilent Technologies). Suitable primers for the introduction of the Cys amminoacid were designed according to the manufacturer's indications and designed by Primm Biotech, left primer:

```
                                           (SEQ ID No: 21)
GGATTCTGCAGTCTATTACTGTGCAACAGGTTGGGGACCTG;

right primer:
                                          (SEQ ID No: 22))
CAGGTCCCCAACCTGTTGCACAGTAATAGACTGCAGAATCC.
```

The sample reaction was prepared as follows: 5 µl of 10× reaction buffer; 1 µl of scFv-hERG1 dsDNA template (13 ng/µl); 1.84 µl (125 ng) left primer; 1.84 µl (125 ng) right primer; 1 µl of dNTP mix; 3 µl of QuickSolution; 36, 32 µl ddH$_2$O. Then 1 µl of PfuTurbo DNA polymerase (2.5 U/µl) was added. Cycling conditions were adjusted: initial melt was performed at 95° C. for 1 min, followed by 18 cycles of a three-step program (95° C., 50 sec; 60° C. 50 sec and 68° C., 4 min). The reaction was then held at 68° C. for 7 min and cooled to 4° C.

After the amplification reaction, 1 µl of DnpI restriction enzyme (10 U/µl) was added directly to the reaction mixture, that was incubated right after at 37° C. for 1 h to digest the parental.

At this point, bacterial DH5α ultra competent cells were transformed through heat-shock. Cells were gently thaw on ice and 2 µl of the DpI-treated DNA was transferred in a separate aliquot of 200 µl of ultracompetent cells. The reaction was incubated on ice for 30 min. The tube was then heat-pulsed at 42° C. in a dry-bath for 45 sec. The tube was incubated on ice for 2 min. Cells were recovered with 450 µl SOC medium (SOB medium supplemented with 1 mM MgSO$_4$, 1 mM MgCl$_2$) and incubated 1 hour at 37° C. on shaking. Bacteria were plated into pre-warming LB-Agar plates containing Ampicillin antibiotic (50 µg/ml) and incubated lid-side down overnight at 37° C.

The following day, several colonies were grown and some of them were picked and DNA was extracted and sequenced to verify the presence of the desired mutation.

The construct obtained was labelled scFv-hERG1-Cys.

13. scFv-hERG1-G3 and scFv-hERG1-D8Cys Expression in *Pichia pastoris*

Linearised scFv-hERG1 and scFv-hERG1-Cys were both digested with SalI and transformed into the *Pichia pastoris* strain GS115 by spheroplasting, generating Mut$^+$ transformants. For the transformation we have referred to the *Pichia* Expression Kit (Invitrogen) indications.

After five days from transformation, single colonies were visible to the naked eye, 92 clones and 4 negative controls were picked and transferred in three different 96-well plates, with different concentration of G418: without G418, 5 mg/ml, 15 mg/ml. G418 selection was performed exploiting the characteristic that pPIC9K contains the bacterial kanamycin gene that confers resistance to Geneticin® in *Pichia*. The level of Geneticin® resistance approximately depends on the number of kanamycin genes integrated. A single copy of pPIC9K integrated into the *Pichia* genome confers resistance to Geneticin® to a level of ~0.25 mg/ml. Multiple integrated copies of pPIC9K can increase the Geneticin® resistance level from 0.5 mg/ml (1-2 copies) up to 4 mg/ml (7-12 copies). Due to the genetic linkage between the kanamycin gene and the expression cassette (both under the P$_{AOX1}$ promoter), we can infer that Geneticin® resistant clones contain multiple copies of the gene of interest. For this same reason, secreted protein expression may increase because of a gene dosage effect. Thus, the presence of pPIC9K was used as a tool to reveal pPIC9K transformants that harbor multiple copies of the genes of interest, scFv-hERG1 and scFv-hERG1-Cys.

After two days of growth at 30° C., six best grown clones from the 15 mg/ml G418 plates were picked up and evaluated for their capacity to expressed the protein of interest, setting up a small scale liquid culture, according to *Pichia* Expression Kit protocol (Invitrogen).

Samples from each clone's culture were collected at different timepoints: 24 h, 48 h, 72 h. After three days of induction with 0.5% final concentration of 100% methanol, supernatants were collected and tested through slot blot.

14. Slot Blot Analysis

Yeast supernatants were collected and tested for protein expression through slot blot; 200 µl of each supernatant were applied to a PVDF membrane (Amersham) assembled in a slot blot device between two squares of 3 mM Whatman paper. The samples were left in incubation for 15 min, then vacuum was applied to dry the samples. The membrane was recovered and wash with T-PBS. Blocking was performed with T-PBS 5% BSA for 45 min and then washed 10 min with T-PBS. The membrane was incubated for 1 hour with anti-6×His-HRP conjugated antibody (Sigma) diluted 1:2000 in 15 ml T-PBS 5% BSA.

15. Ni Sepharose Purification

Supernatants, obtained from the screening of the clones after yeast transformation, were incubated O/N in rolling with Ni Sepharose 6 Fast Flow (Ge Healthcare) according to manufacturer's instructions. After, two wash steps were carried out with 500 µl Wash Buffer (20 mM sodium phosphate, 500 mM NaCl, pH 7.3) and elution was performed using 250 µl Elution buffer (20 mM sodium phosphate, 500 mM imidazole, pH 7.3).

16. AKTA Purification

Purification of 1 liter yeast supernatant of scFv-hERG1-G3 and scFv-hERG1-D8Cys, respectively, was performed by Affinity Chromatography, using an ÄKTA Protein Purification System (Ge Healthcare Life Sciences) with HisTrap HP 1 ml columns. Wash steps and equilibration were performed according to the manufacturer's instructions, using Wash buffer (20 mM sodium phosphate, 500 mM NaCl, pH 7.3); elution was performed utilizing a linear gradient of Elution buffer (20 mM sodium phosphate, 500 mM NaCl, 500 mM imidazole, pH 7.3). Analysis was accomplished using UNICORN 7.0 software.

17. Gel Filtration

Samples obtained from purification of both antibodies were gel filtered, using Superdex 75 HR 10/30 (Ge Healthcare Life Sciences). Wash buffer composition (20 mM sodium phosphate, 150 mM NaCl, pH 7.3) was adjusted to optimize protocol conditions. Elutions were analyzed through SDS-Page.

18. Sodium Dodecyl Sulphate Polyacrylamide Gel Electrophoresis (SDS-PAGE)

Each sample was applied with the same volume of 15 µl to a stacking gel (400 µl acrylamid (40%)-bisacryamide (0.8%), 1 ml 0.5 M Tris-HCl, pH 6.8, 40 µl 10% SDS, 20 µl 10% ammonium persulfate, 4 µl TEMED, 2.54 ml $H_2O$). Stacking gel were added on the resolving gel (2.6 ml acrylamid (40%)-bisacryamide (0.8%), 1.75 ml 1.5 M Tris-HCl, pH 8.8, 70 µl 10% SDS, 35 µl 10% ammonium persulfate, 3.5 µl TEMED, 2.55 ml $H_2O$). Electrophoretic run were performed at 150 V. Gels were either stained with Coomassie Brilliant Blue or transferred to PVDF membranes for western blotting analysis to assess the presence of the protein (around 30 KDa).

19. Western Blotting

After SDS-PAGE gels were transferred to PVDF membrane (Amersham) in transfer buffer (14.4 g, 3.03 g TrisHCl, 200 ml methanol, 800 ml $H_2O$) at 100 V for one hour. Membranes were washed in T-PBS (PBS 0.1% Tween) and then blocked with T-PBS 5% BSA O/N. Membranes were exposed to primary antibody peroxidise-coupled (Sigma) diluted in T-PBS 5% BSA for one hour at room temperature. After washing the membranes three times for ten minutes, signals were visualized using ECL reagent (Amersham).

WB were performed by using the following antibodies: antimyc (1:1000) and anti-6×His-HRP conjugated antibody (Sigma).

20. scFv-hERG1-G3 and scFv-hERG1-D8Cys quantification, ELISA assay and Biacore analysis scFv-hERG1-G3 and scFv-hERG1-D8Cys were gathered together and dialyzed against PBS 1× using Slide-A-Lyzer™ Dialysis Cassettes (Thermo Fisher). Protein absorbance at 280 nm was measured and Lambert-Beer equation was applied.

To evaluate if the two engineered antibodies, scFv-hERG1-G3 and scFv-hERG1-D8Cys, have still the ability to bind the antigen and afterwards to investigate the different affinity of the two antibodies ELISA assays were performed using plates coated with S5-Pore peptide (sequence: EQPHMDSRIGWLHN), towards which the antibody is directed. This peptide is the same we used to screen anti-hERG1 A7 antibody.

21. Antibody Labeling with Alexa 488 scFv-hERG1-G3 and scFv-hERG1-D8Cys were conjugated with Alexa Fluor® 488 Microscale Protein Labeling Kit (Thermo Fisher Scientific), according to the protocol indications.

22. Immunofluorescence on Fixed Cells

HEK 293 hERG1 (HEK293 stably transfected with pcDNA3.1-hERG1 cDNA construct) and HEK-MOCK (HEK 293 stably transfected with pcDNA 3.1 cDNA) were grown in DMEM medium with 10% FBS EU serum in a 37° C. incubator with 5% $CO_2$. Cells were seeded O/N on glass coverslips and then washed once with PBS and fixed with 4% paraformaldeide for 20 min at room temperature. Blocking was performed with 10% BSA for 2 h at room temperature. Antibody incubation was performed using scFv-hERG1-G3, scFv-hERG1-D8Cys, diluted 1:20 in blocking solution and incubated for 2 and half hours, followed by anti-His (1:250; Abcam) O/N incubation in blocking solution. The following day, cells were washed three times with PBS and incubated with anti-mouse Alexa488 antibody (Invitrogen) for 1 h. Whereas, scFv-hERG1-G3-Alexa488 and scFv-hERG1-D8Cys-Alexa488, diluted 1:20 in blocking solution, were incubated O/N at 4° C.

For revelation cells were incubated with Hoechst (1:1000) for 30 min and then mounted with propyl gallate. Cells were visualized on a confocal microscope (Nikon, C1).

Immunofluorescence quantification was performed using ImageJ software: for each image, the measure of three different areas was performed and the mean was calculated.

23. Immunofluorescence on Live Cells

Cells were grown O/N on 60 mm plates (Sarstedt) using an agarose (15 g/L) ring in order to isolate cells and minimize the volumes of reagents needed for incubations. Cells were incubated with scFv-hERG1-G3-Alexa488 and scFv-hERG1-D8Cys-Alexa488 diluted 1:20 in complete culture medium in a 37° C. incubator with 5% C02 for 4 h. Rivelation was performed using Hoechst, as previously described. Cells were visualized on a inverted light microscopy (Nikon, Eclipse TE300).

24. Cell Viability

Cell viability was evaluated performing Trypan blue assay; briefly HCT-116, MDA-MB231, MIA PACA2, HEK293 hERG1, HEK-MOCK, FLG 29.1, PANC-1, BXPC3 cells at a density of $5 \times 10^3$ cells/well were seeded in a 96-well plate. After 24 h, the medium was replaced by 100 µl of fresh medium containing different concentrations of the scFv-hERG1-D8Cys antibody (10 µg/ml and 20 µg/ml). The complete immunoglobulin, anti-hERG1 monoclonal antibody was tested at a concentration of 100 µg/ml. Cells were cultured 24 h in a humidified incubator at 37° C. and 5% $CO_2$. After the treatment cells were detached and viable cells were counted. Experiments were performed in triplicate.

25. Spheroids 3D Culture and scFv-hERG1 Test on Spheroids

HEK-293 hERG1, HEK-MOCK, MDA-MB231, MIA PACA2 and PANC-1 were seeded in a 96-well plate at a density of $10^3$ cells/well for each well on a 1.5% agarose base-layer. 100 µL of fresh medium were added to each well and cells were left to grow for 72 h in a 37° C. incubator with 5% C02. After 72 h spheroids were visible and the medium was replaced by 100 µl of fresh medium containing different concentrations of the scFv-hERG1-D8Cys antibody (10 µg/ml and 20 µg/ml and 40 µg/ml).

Pictures were taken using Nikon, Eclipse TE300 every 24 h until 72 h when Calcein AM cell viability assay was performed.

The volume of spheroids was evaluated analyzing the pictures taken at 24 h, 48 h and 72 h using MATLAB Software.

Experiment was performed in triplicate.

26. β1Integrin mAb: RNA Reverse Transcription

TS2/16 and BV7 RNA was reverse transcribed into cDNA using oligo(dT) primers (Invitrogen) and SuperScript® II Reverse Transcriptase (Invitrogen) according to manufacturer's instructions in a total volume of 40 µl.

| Component | Stock concentration | Final concentration | Amount |
| --- | --- | --- | --- |
| RNA | | 100 ng/µl | 4 µg |
| Oligo(dT)12-18 | 500 µg/ml | 25 µg/ml | 2 µl |
| dNTPmix | 10 mM each | 0.5 mM | 2 µl |
| PCR grade H2O | — | — | 18 µl |

The mix was incubated in the thermocycler at 65° C. for 5 minutes, and then quickly chilled on ice and added with the following components:

| Component | Stock concentration | Final concentration | Amount |
|---|---|---|---|
| 5x First Strand Buffer | 5x | 1x | 8 µl |
| PCR grade H2O | — | — | 6 µl |

The mix was then heated at 42° C. for 2 minutes and then added with the enzyme

| Component | Stock concentration | Final concentration | Amount |
|---|---|---|---|
| Superscript ™ II RT | 200 U/µl | 5 U/µl | 2 µl |

The mix (40 µl) was then incubated at 42° C. for 50 minutes and then the reaction was inactivated at 70° C. for 15 minutes.

27. β1 Integrin mAb: Isolation of Variable Domains BY Polymerase Chain Reaction (PCR)

To isolate antibody variable domains (VL and VH) was performed a PCR with the primers reported in Wang et al. (2000) with modifications (Table 2).

Table 2. Primers used for the isolation of VL and VH variable domains, form Wang et al., (2000) with modifications

| Component | Stock concentration | Final concentration | Amount |
|---|---|---|---|
| 10x Buffer | 10x | 1x | 5 µl |
| MgSO4 | 25 mM | 1.5 mM | 3 µl |
| dNTPs | 2 mM each | 0.2 mM each | 5 µl |
| Forward primer | 10 µM | 0.3 µl | 1.5 µl |
| Reverse primer | 10 µM | 0.3 µl | 1.5 µl |
| DNA | — | — | 10 ng |
| KOD Hot Start DNA Polymerase | 1 U/µl | 0.02 U/µl | 1 µl |
| PCR grade H2O | — | — | to 50 µl |

The mix was incubated in the thermocycler with following protocol:

| Step | Temperature | Time |
|---|---|---|
| 1 | 95° C. | 2 min |
| 2 | 95° C. | 20 sec |
| 3 | 54° C. (VH) or 46° C. (VL) | 10 sec |
| 4 | 70° C. | 10 sec |
| 5 | 70° C. | 5 min |

| Kappa light chain | Primer name | Sequence |
|---|---|---|
| Forward primer | degKappadir | GAYATTGTGMTSACMCARWCTMCA (SEQ ID No 31) |
| Reverse primer | Kapparev | GGATACAGTTGGTGCAGCATC (SEQ ID No 32) |

| IgG1 heavy chain | Primer name | Sequence |
|---|---|---|
| Forward primer | degH1dir | CAGGTTACTCTGAAAGWGTSTG (SEQ ID No 33) |
| Forward primer | degH2dir | GAGGTCCARCTGCAACARTC (SEQ ID No 34) |
| Forward primer | degH3dir | CAGGTCCAAACTUCAGCARCC (SEQ ID No 35) |
| Forward primer | degH4dir | GAGGTGAASSTGGTGGAATC (SEQ ID No 36) |
| Forward primer | degH5dir | GATGTGAACTTGGAAGTGTC (SEQ ID No 37) |
| Reverse primer | IgG1rev | GGAAGATCTATAGACAGATGGGGGTGTCGTTTTGGC (SEQ ID No 38) |

There are two classes of light chain: kappa and lambda; but since the 95% of mouse antibodies have kappa light chain (Honjo and Alt, 1995) were chosen primers specific for kappa light chain ignoring the lambda type. Forward primers were designed using protein sequence alignment of Framework1 (FRW1) of each chain variable region. Reverse primers were designed on the constant region (CH1) next to the end of the variable domain of each chain (Kappa light chain or IgG1 heavy chain). For kappalight chain were used only one primer pair, while for heavy chain were used 5 primer pairs composed by IgG1rev in combination with the 5 forward primers.

For VH isolation of both TS2/16 and BV7 were chosen IgG1rev-degH4dir primer pair.

In order to prevent mutation due to DNA Polymerase, were used a high fidelity DNA polymerase with proof reading activity: KOD Hot Start DNA Polymerase (Novagen) using the following protocol:

Steps 2-4 were repeated 30 times.

28. β1 Integrin mAb: Cloning of Variable Domains without the Use of Restriction Enzymes In order to sequence VH and VL variable domains were cloned without the use of restriction enzymes in a vector suitable for DNA sequencing. We used TA-Cloning Kit or Zero-Blunt Cloning kit (Invitrogen) following manufacturer's instructions.

DNA Electrophoresis and Purification from Agarose Gel

DNA electrophoresis uses an electrical field to move the negatively charged DNA toward a positive electrode through an agarose gel matrix. PCR products and restriction enzyme digested DNA were run on agarose gel (1.5% agarose in TAE (Tris, Acetic acid, EDTA) buffer) stained with ethidium bromide, alongside 2 log DNA ladder (NEB) in order to separate different size fragments. Electrophoresis was run at 100 V. The band of interest was thus excised from gel with a clean scalpel and purified using QIAquick PCR Purification Kit (QIAGEN) following manufacturer's instructions. Purified DNA was eluted with 30 µl PCR grade H₂O.

Splicing by Overlap Extension PCR (SOE-PCR)

ScFv construct was assembled by Splicing by Overlap Extension PCR (SOE-PCR) in the order VL-linker-VH, using the primers described in (Wang et al 2000) with modifications (Table 3). The polypeptide linker joining the variable domains was designed as four GGGGS repeats.

Table 3. Primer designed to assemble the construct VL-linker-VH by SOE-PCR (VLREVSOE and VHFORSOE) and clone the sequence into pHenIX vector (VLFORSFI and VHREVNOT), or into scFv-hERG-pHenIX vector (VL-FORXHO and VHREVAPALI). In italics are the portions of the primers that anneal to the template, highlighted in grey are the sequences added to clone the construct in frame with the expression cassette in pHenIX or in scFv-hERG1-pHenIX vector, underlined are the restriction sites, grey are the sequences added to facilitate enzyme digestion, and bold are the sequenced that overlap in SOE-PCR.

| Name | Sequence |
| --- | --- |
| VLFORSFI | GGCCCAGCCGGCCATGGCCGATATTGTGATGACACA GACTCCA (SEQ ID No 39) |
| VLREVSOE | GGAGCCGCCGCCGCCAGAACCACCACCACCAGAACCACCAC CACCGGATACAGTTGGTGCAGCATC (SEQ ID No 40) |
| VHFORSOE | GGCGGCGGCGGCTCCGGTGGTGGTGGATCCGAGGTGAAGG TGGTGGAATC (SEQ ID No 41) |
| VHREVNOT | GCGGCCGCATAGACAGATGGGGGTGTCGTTTT GGC (SEQ ID No 42) |
| VLFORXHO | CTCGAGTGATATTGTGATGACACAGACTCCA (SEQ ID No: 43) |
| VHREVAPALI | GTGCACTATAGACAGATGGGGGTGTCGTTTTGGC (SEQ ID No 44) |

The protocol consists in two steps described in FIG. 10. The first step allows to add: at the 3' end of VL, a sequence that encode the first three GGGGS repeats of the linker, and at the 5' end of VH a sequence that encode the last two GGGGS repeats of the linker. During this step will be also attached at the 5' end of VL and at the 3' end of VH the restriction sites that will be used for the cloning of VL-linker-VH construct in the expression vector. The second step allows to join the two PCR products thanks to the overlapping sequences (15 bp) at the 3' end of VL and at the 5' end of VH.

In the first step were performed two parallel PCR: one with VLFORSFI-VLREVSOE primer pair and pCRII-VL template; and the other with VHFORSOE-VHREVNOT primer pair and pCRII-VH template. PCR protocol using KOD DNA Polymerase was performed as previously described.

In the second step, we settled up the SOE-PCR using as template 1 µl of each PCR reaction performed in the first step, and VLFORSFI-VHREVNOT primer pair, following the protocol below:

| Component | Stock concentration | Final concentration | Amount |
| --- | --- | --- | --- |
| 10x Buffer | 10x | 1x | 5 µl |
| MgSO4 | 25 mM | 1.5 mM | 3 µl |
| dNTPs | 2 mM each | 0.2 mM each | 5 µl |
| VLFORSFI primer | 10 µM | 0.3 µl | 1.5 µl |
| VHREVNOT primer | 10 µM | 0.3 µl | 1.5 µl |
| PCR VL (STEP 1) | — | — | 1 µl |
| PCR VH (STEP 1) | — | — | 1 µl |
| KOD Hot Start DNA Polymerase | 1 U/µl | 0.02 U/µl | 1 µl |
| PCR grade H2O | — | — | to 50 µl |

The mix (50 µl) was incubated in the thermocycler according to the protocol below:

| Step | Temperature | Time |
| --- | --- | --- |
| 1 | 95° C. | 2 min |
| 2 | 95° C. | 20 sec |
| 3 | 70° C. | 10 sec |
| 4 | 70° C. | 10 sec |
| 5 | 70° C. | 5 min |

Steps 2-4 were repeated 30 times

29. Production and Characterization of Anti-hERG1-β1 Single Chain Diabody (scDb)-scDb-hERG1-β1 Antibody The construct hERG1-β1-scDb was transformed into GS115 *Pichia pastoris* strain according to the spheroplasting technique previously described and the protein has been expressed and purified applying the expression and purification protocol previously described for the scFv-hERG1 and scFv-hERG1-Cys antibodies.

Cell ELISA

Cell ELISA on living cells was performed according to Sette et al., (2013). HEK 293 WT (hERG1−/β1+) and HEK 293-hERG1 (hERG1+/β1+) cells were seeded to semiconfluence in 96-well plate in DMEM plus 10% fetal bovine serum (FBS) and incubated overnight at 37° C. and 5% C02. After three washes with PBS, anti-hERG1-β1-scDb was diluted at different concentrations into culture medium and added to the cells for two 2 hours at room temperature. The following steps were the same as described above.

Immunofluorescence (IF)

IF was performed following the protocol which has been previously described. Coverslips were coated with BSA and Fibronectin for two hours. IF was performed on HEK 293 WT (hERG1−/β1+), HEK 293-hERG1 (hERG1+/β1+) and GD25 WT cells (hERG1−/β1−).

30. Production and Preliminary Characterization of Anti-hERG1-β1 Single Chain Diabody (scDb)-scDb-hERG1-Cys-β1-Antibody scDb-hERG1-β1 MUTAGENESIS Mutagenesis was performed on the scDb-hERG1-β1 expression cassette cloned into pPIC9K using the QuikChange®XL Site-Directed Mutagenesis Kit (Stratagene, Agilent Technologies). Suitable primers for the introduction of the Cys amminoacid were designed according to the manufacturer's indications and designed by Primm Biotech, left primer:

```
                                         (SEQ ID No: 21)
GGATTCTGCAGTCTATTACTGTGCAACAGGTTGGGGACCTG;

right primer:
                                        (SEQ ID No: 22))
CAGGTCCCCAACCTGTTGCACAGTAATAGACTGCAGAATCC.
```

The sample reaction was prepared as follows: 5 µl of 10× reaction buffer; 1 µl of scFv-hERG1 dsDNA template (13 ng/µl); 1.84 µl (125 ng) left primer; 1.84 µl (125 ng) right primer; 1 µl of dNTP mix; 3 µl of QuickSolution; 36, 32 µl ddH$_2$O. Then 1 µl of PfuTurbo DNA polymerase (2.5 U/µl) was added. Cycling conditions were adjusted: initial melt was performed at 95° C. for 1 min, followed by 18 cycles of a three-step program (95° C., 50 sec; 60° C. 50 sec and 68° C., 4 min). The reaction was then held at 68° C. for 7 min and cooled to 4° C.

After the amplification reaction, 1 µl of DnpI restriction enzyme (10 U/µl) was added directly to the reaction mixture, that was incubated right after at 37° C. for 1 h to digest the parental. At this point, bacterial DH5α ultra competent cells were transformed through heat-shock. Cells were gently thaw on ice and 2 µl of the DpI-treated DNA was transferred in a separate aliquot of 200 µl of ultracompetent cells. The reaction was incubated on ice for 30 min. The tube was then heat-pulsed at 42° C. in a dry-bath for 45 sec. The tube was incubated on ice for 2 min. Cells were recovered with 450 µl SOC medium (SOB medium supplemented with 1 mM MgSO$_4$, 1 mM MgCl$_2$) and incubated 1 hour at 37° C. on shaking. Bacteria were plated into pre-warming LB-Agar plates containing Ampicillin antibiotic (50 µg/ml) and incubated lid-side down overnight at 37° C.

The following day, several colonies were grown and some of them were picked and DNA was extracted and sequenced to verify the presence of the desired mutation.

The construct obtained was labelled scDb-hERG1-Cys-β1.

Expression and Purification of scDb-hERG1-Cys-β1 Antibody.

scDb-hERG1-Cys-β1 was transformed in GS115 *Pichia pastoris* yeast strain according to the spheroplasting technique previously described and the protein has been expressed and purified applying the expression and purification protocol previously described for the scFv-hERG1 and scFv-hERG1-Cys antibodies using AKTA Pure (Ge Healthcare). Chromatograms were analyzed using Unicorn 7.0 Software.

Immunofluorescence (IF)

IF was performed following the protocol which has been previously described. Coverslips were coated with BSA and Fibronectin for two hours. IF was performed on GD25 WT cells (hERG1−/β1−), HEK 293 WT (hERG1−/β1+), HEK 293-hERG1 (hERG1+/β1+), following the protocol previously described. IF was performed using scDb-hERG1-Cys-β1 conjugated with Alexa488 fluorophore.

Viability Assay

PANC-1 (pancreatic ductal adenocarcinoma) cells and MDA-MB 231 (breast cancer) cells were seeded at $5*10^5$ in 96 well-plates and let grown O/N. The following day cells were treated with scDb-hERG1-Cys-β1 at different dilutions (0, 10, 20, 40, 100 µg/ml) and incubate with the antibody 24 h. Each condition was performed in triplicate.

After incubation cells were detached and counted, for $IC_{50}$ determination Origin Software was applied.

3D Spheroid Culture $10^3$ PANC-1 and MDA-MB 231 cells were seeded on an agarose base layer (1.5 g/l) in 96 well plate and grown for 72 hours in a humidified incubator at 37° C. and 5% CO$_2$. Then scDb-hERG1-Cys-β1 was administered (40 µg/ml), diluted in culture medium, while fresh medium without antibody was added to wells containing cells treated as negative controls. Photos were taken at 24 hours to monitor cell growth using a Nikon, Eclipse TE300 microscope.

Lateral Motility Assay

Cells were plated in 35 mm Petri dishes at an initial density of $5*10^5$ and allowed to settle for 24 h.

Lateral motility was assessed by a monolayer wound assay (Silletti et al., 1995; Peck and Isacke, 1996). Wound widths were determined immediately afterwards (0 h) by measuring the width of the wound at 45 fixed points Cellular motility was quantified as the "motility index" (MI) defined as follows:

$$MI=1-(Wt/Wo)$$

MI=0 indicated no movement of cells whilst values of MI=1 indicated complete wound closure Biodistribution of scFv-hERG1-D8Cys and scDb-hERG1-Cys-β1 Antibodies.

160 µg of each antibody have been injected in two Balb/c mice i.v. Blood samples have been collected from each mouse at different timpanist following the i.v.: 5, 10, 30 min 1 h, 2 h, 6 h, 24 h after injection. Blood samples have been processed and plasma isolated. ELISA test on plasma samples was performed following the protocol previously described in this section. $t_{1/2}$ were calculated applying Precise PK Pharmacokinetic Software.

ECG Measurements.

ECG measurements were performed before antibody administration and continuously after i.v. injection of the antibody for 15 min.

In Vivo Experiments

In Vivo Analysis

Labeling of the scFv-hERG1-D8Cys with Alexa 750: 150 µg of scFv-hERG1-D8Cys at a concentration of 2 mg/ml in PBS solution and 0.1 M sodium bicarbonate buffer pH 8.3, were incubated 1 h at 22° C. in agitation with 12 µl of Alexa Fluor® 750 NHS Ester (Succinimidyl Ester) (Thermo Fisher Scientific), resuspended in DMSO at 10 mg/ml. The reaction was blocked for 5 min in ice and the labelled protein was purified by size exclusion chromatography on a Sephadex G25 (Sigma) column equilibrated with PBS.

In vivo imaging. Three six-week old, female immunodeficient Athymic Nude-Foxn1 nu/nu mice were injected intravenously with 50 μl (1 nm dye/mouse) of scFv-hERG1-D8Cys labeled with the fluorophore Alexa 750 and fluorescence was measured 5, 10, 60 min and 24 h after antibody injection. One control mouse was treated with sterile PBS solution. All the fluorescent emission spectra were measured using a Photon imager (Biospace Lab). The imager had a laser source for fluorescence excitation ($\lambda$=679 nm), an emission filter ($\lambda$=702 nm) for fluorescence detection, and a computer for data analysis.

Mouse Model: the MIAPaCa-2 cell line was used for tumor cell implantation, as described in Lastraioli et al., 2015. Cells were cultured in DMEM supplemented with L-glutamine (4 mM), 10% fetal bovine serum and Geneticin (G418) (2.4 mg/ml) (Gibco) at 37° C. in a humidified atmosphere of 5% CO2. MIAPaCa-2-luc cells were injected into the pancreas of nu/nu mice and the animals were monitored (as described in [17]) and 45 days after the cell inoculum, mice were administered with scFv-hERG1-D8Cys-Alexa750 antibody.

The invention claimed is:

1. A bispecific anti-hERG1 and anti-β1 integrin antibody (Ab) comprising the Heavy chain Variable (VH) domain and Light chain Variable (VL) domain of an anti-hERG1 Ab which binds the extracellular domain S5-P of hERG1 and the Heavy chain Variable (VH) domain and Light chain Variable (VL) domain of an anti-β1 integrin Ab which bind the extracellular domain of β1 integrin, wherein the Heavy chain Variable (VH) domain of anti-hERG1 Ab comprises SEQ ID No: 8 wherein the residue at position 95 of SEQ ID No: 8 is Cys; and the Light chain Variable (VL) domain of anti-hERG1 Ab comprises SEQ ID No: 4; and the Heavy chain Variable (VH) domain of anti-β1 integrin Ab comprises SEQ ID No: 26 or SEQ ID No: 46 and a Light chain Variable (VL) domain of anti-β1 integrin Ab comprises SEQ ID No: 24 or SEQ ID No: 48.

2. The bispecific Ab according to claim 1 has a format selected in the group consisting of Tandem scFvs, Diabody format, Single-chain diabodies, Tandem diabodies (Tand-Abs) and Dual-affinity retargeting molecules (DARTs).

3. The bispecific Ab according to claim 2 comprising a first Heavy chain Variable (VH) domain comprising with SEQ ID NO: 8 wherein the residue at position 95 of SEQ ID NO: 8 is Cys, and a first VL domain comprising SEQ ID NO:4, and a second VH domain comprising SEQ ID NO:26, and a second VL domain comprising SEQ ID NO:24.

4. The bispecific Ab according to claim 3 wherein domains are assembled in the following order: anti-hERG1-Cys VH domain linked by a first linker to anti-β1-integrin VL domain linked by a second linker to anti β1-integrin VH domain linked by a third linker to anti-hERG1-Cys VL domain.

5. The bispecific Ab according to claim 4 wherein the linkers comprise (Gly4Ser)3 motifs.

6. A pharmaceutical composition comprising a bispecific Ab according to claim 1 and a pharmaceutically acceptable ingredient.

7. A polynucleotide encoding the bispecific Ab according to claim 1.

8. An expression vector or a plasmid comprising the polynucleotide according to claim 7.

9. A genetically modified microorganism or a cell comprising the expression vector or plasmid according to claim 8.

10. A kit comprising a bispecific antibody according to claim 1.

11. The kit of claim 10, said kit further comprising an anti-hERG1-Cys scFv comprising a VH domain comprising SEQ ID NO: 8 wherein the residue at position 95 of SEQ ID NO: 8 is Cys, and a VL domain comprising SEQ ID NO: 4, said antibody specifically binds hERG1 S5-pore extracellular portion.

12. An anti-hERG1 antibody comprising a Heavy chain Variable (VH) domain comprising SEQ ID NO:8 wherein the residue at position 95 of SEQ ID No: 8 is Cys, and a Light chain Variable (VL) domain comprising SEQ ID NO:4, said antibody specifically binds hERGI S5-pore extracellular portion.

13. The anti-hERG1 antibody according to claim 12 which is a fully humanized recombinant Ab, a scFv, Fab, Fv form of simple chain of scFv, diabodies, triabodies, bispecifics, minibodies or phage antibodies.

14. The anti-hERG1 antibody according to claim 13, wherein said molecule is a scFv and wherein VH and VL are linked by a peptide linker.

15. The anti-hERG1 antibody according to claim 14, wherein the peptide linker comprises a (Gly4Ser)3 motif.

16. The anti-hERG1 antibody according to claim 12 having SEQ ID No: 10.

17. The anti-hERG1 antibody according to claim 12 which is labelled with a fluorophore or a radionuclide.

18. A pharmaceutical composition comprising the anti-hERG1 antibody according to claim 12 and a pharmaceutically acceptable ingredient.

19. A polynucleotide encoding the anti-hERG1 antibody according to claim 12.

20. An expression vector or a plasmid comprising the polynucleotide according to claim 19.

21. A genetically modified microorganism or a cell comprising the expression vector or plasmid according to claim 20.

22. A kit comprising an anti-hERG1-Cys scFv comprising a VH domain comprising SEQ ID NO: 8 wherein the residue at position 95 of SEQ ID NO: 8 is Cys, and a VL domain comprising SEQ ID NO: 4, said antibody specifically binds hERG1 S5-pore extracellular portion.

* * * * *